(12) United States Patent
Lim et al.

(10) Patent No.: US 10,054,599 B2
(45) Date of Patent: *Aug. 21, 2018

(54) PRE-ECLAMPSIA BIOMARKERS

(71) Applicants: **Agency for Science, Technology and Research (A*STAR), Singapore (SG); Singapore Health Service PTE LTD**, Singapore (SG)

(72) Inventors: Sai Kiang Lim, Singapore (SG); Kok Hian Tan, Singapore (SG)

(73) Assignees: **AGENCY FOR SCIENCE, TECHNOLOGY AND RESEARCH (A*STAR), Singapore (SG); SINGAPORE HEALTH SERVICES PTE, LTD.**, Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 14/773,677

(22) PCT Filed: Mar. 12, 2014

(86) PCT No.: PCT/SG2014/000120
§ 371 (c)(1),
(2) Date: Sep. 8, 2015

(87) PCT Pub. No.: WO2014/142752
PCT Pub. Date: Sep. 18, 2014

(65) Prior Publication Data
US 2016/0025739 A1    Jan. 28, 2016

(30) Foreign Application Priority Data

Mar. 12, 2013 (SG) .............................. 201301830-4
Aug. 14, 2013 (SG) .............................. 201306148-6

(51) Int. Cl.
| | | |
|---|---|---|
| G01N 33/68 | (2006.01) |
| A61K 31/166 | (2006.01) |
| A61K 31/4422 | (2006.01) |
| A61K 31/4439 | (2006.01) |
| A61K 31/502 | (2006.01) |
| A61K 33/06 | (2006.01) |

(52) U.S. Cl.
CPC ......... *G01N 33/689* (2013.01); *A61K 31/166* (2013.01); *A61K 31/4422* (2013.01); *A61K 31/4439* (2013.01); *A61K 31/502* (2013.01); *A61K 33/06* (2013.01); *G01N 33/6893* (2013.01); *G01N 2333/4727* (2013.01); *G01N 2333/495* (2013.01); *G01N 2333/5412* (2013.01); *G01N 2333/58* (2013.01); *G01N 2333/585* (2013.01); *G01N 2333/70596* (2013.01); *G01N 2333/71* (2013.01); *G01N 2333/8132* (2013.01); *G01N 2333/8146* (2013.01); *G01N 2333/9129* (2013.01); *G01N 2570/00* (2013.01); *G01N 2800/368* (2013.01); *G01N 2800/52* (2013.01); *G01N 2800/60* (2013.01)

(58) Field of Classification Search
None
See application file for complete search history.

(56) References Cited

U.S. PATENT DOCUMENTS

2009/0104649 A1   4/2009   Garovic

FOREIGN PATENT DOCUMENTS

WO   2013/081554 A1   6/2013

OTHER PUBLICATIONS

Thesis by Christianne Lok, downloaded the Institutional Repository of the University of Amsterdam (UvA) http://dare.uva.nl/document/107877; 2008; 218 pages total.*
Atkinson et al., J. Lipid Res, 2009; 50: 71-80.*
Orozco et al., "Membrane Protected Apoptotic Trophoblast Microparticles Contain Nucleic Acids", The American Journal of Pathology, 173(6): 1595-1608 (2008).
Baig et al., "Lipidomic analysis of human placental Syncytiotrophoblast microvesicles in adverse pregnancy outcomes", Placenta 34(5):436-442 (2013).
Boing et al., Microparticles: mediators of cellular and environmental homeostasis: Chapter 5—Circulating platelet-derived and placenta-derived microparticles expose Flt-1 in preeclampsia. "Materials and Methods: Flow Cytometry", Retrieved from the Internet http://dare.uva.nl/record/374408, (2011).
Bretelle et al., "Circulating microparticles: a marker of procoagulant state in normal pregnancy and pregnancy complicated by preeclampsia or intrauterine growth restriction", Thromb Haemost, 89(3): 486-492 (2003).
Guller et al., "Protein composition of microparticles shed from human placenta during placental perfusion: Potential role in angiogenesis and fibrinolysis in preeclampsia", Placenta 32(1): 63-69 (2011).
Marques et al., "Circulating microparticles in severe preeclampsia", Clin Chim Acta, 414: 253-258 (2012).
Petrozella et al., "Endothelial microparticles and the antiangiogenic state in preeclampsia and the postpartum period", Am J Obstet Gynecol 207(2): 140.e20-140.e26 (2012).
Smalley et al., "Plasma-Derived Microparticles for Biomarker Discovery", Clin Lab, 54(3-4): 67-69 (2008).

* cited by examiner

*Primary Examiner* — Christina M Borgeest
(74) *Attorney, Agent, or Firm* — Nixon Peabody LLP; Mark J. FitzGerald; Srividya Subramanian

(57) ABSTRACT

We describe a method of detecting pre-eclampsia in a cell, tissue, organ or organism, the method comprising detecting a modulated level of expression, activity or amount of a pre-eclampsia biomarker polypeptide selected from the group consisting of PlGF, FLT1, BNP, ANP, CD9, PAI-1, TGF β, PCT, SI 00b, TIMP1, CD 105 and IL6 in or of a microparticle type (selected from a CTB binding microparticle and an Annexin V binding microparticle) from the cell, tissue, organ or organism, as compared to level of expression, activity or amount of the pre-eclampsia biomarker polypeptide in the same microparticle type in a cell, tissue, organ or organism not sufferin from pre-eclampsia.

15 Claims, 6 Drawing Sheets a  CTB b  AV

PRE-ECLAMPSIA BIOMARKERS

CROSS-REFERENCE TO RELATED APPLICATIONS

This application is a National Phase Entry Application under 35 U.S.C. § 371 of International Application No. PCT/SG2014/000120 filed Mar. 12, 2014, and claims benefit under 35 U.S.C. § 119 of Singapore Provisional Application No. 201301830-4 filed Mar. 12, 2013 and Singapore Provisional Application No. 201306148-6 filed Aug. 14, 2013, the contents of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Sep. 21, 2017, is named 049595-085720-US_SL.txt and is 16,269 bytes in size.

FIELD

The present invention relates to the fields of medicine, cell biology, molecular biology and genetics. This invention relates to the field of medicine.

In particular, it relates to methods of monitoring the physiological or pathological state of a cell, tissue, organ or organism. The invention also relates to the diagnosis and treatment of diseases such as pre-eclampsia.

Reference is made, to U.S. Patent Application Nos. 60/713,992, Ser. Nos. 12/065,549, 12/065,551, 60/878,222, Ser. No. 12/377,398, 61/066,671, 61/227,865 and 61/257,121. Reference is also made to International Patent Application Numbers PCT/GB2005/003206, PCT/SG2006/000233, PCT/SG2006/000232, PCT/SG2007/000257, PCT/SG2009/000062 and PCT/SG2012/000451.

The foregoing applications, and each document cited or referenced in each of the present and foregoing applications, including during the prosecution of each of the foregoing applications ('application and article cited documents'), and any manufacturer's instructions or catalogues for any products cited or mentioned in each of the foregoing applications and articles and in any of the application and article cited documents, are hereby incorporated herein by reference. Furthermore, all documents cited in this text, and all documents cited or reference in documents cited in this text, and any manufacturer's instructions or catalogues for any products cited or mentioned in this text or in any document hereby incorporated into this text, are hereby incorporated herein by reference. Documents incorporated by reference into this text or any teachings therein may be used in the practice of this invention. Documents incorporated by reference into this text are not admitted to be prior art.

BACKGROUND

Pre-eclampsia (PE) remains one of the most common causes of adverse pregnancy outcome in developed and developing countries. The incidence of PE is substantial, about 3% to 8%[1,2]. PE places the obstetric patient and her baby at substantial risk of pre-term birth and perinatal mortality, and severe maternal hypertension and multi-systemic organ dysfunction and damage, including eclampsia and abruption placentae[3,4]. Predictive tests for pre-eclampsia early in the course of pregnancy would provide sufficient time to intervene and mitigate the risks of PE. There has been an intense interest in biomarkers for the identification of patients at risk for preeclampsia. Although clinical risk factors for pre-eclampsia are well known, these factors either singly or in combination have limited predictive values and this has led to intense search for predictive biomarkers for PE, particularly in plasma[5]. However, plasma-derived predictive biomarkers like the generic disease biomarkers are generally low abundance proteins and their discovery is confounded by the dominance of several high abundance proteins such as albumin and immunoglobulins. Despite much effort to eliminate or reduce these abundant proteins, circumventing these high abundance plasma proteins remains a challenge. However, the recent extraction of membrane vesicles from bodily fluids such as plasma or urine[6] for biomarker discovery inadvertently resolved this challenge as removal of the high abundance plasma proteins is inherent in the extraction of membrane vesicles.

The cell sources of these circulating vesicles are likely to be diverse as many cell types are known to secrete membrane vesicles. Since these vesicles are essentially fragments of the secreting cells, they and their cargo are microcosms of their cell sources and would reflect the physiological or diseased state of the cells, making them potential sources of biomarkers for disease diagnosis or prognosis. Indeed, pregnancy-associated exosomes were reported as early as 2006[7]. Circulating plasma vesicles are highly heterogeneous and several distinct classes of membrane vesicles have been described. They include microvesicles, ectosomes, membrane particles, exosome-like vesicles, apoptotic bodies, prostasomes, oncosomes, or exosomes, and are differentiated based on their biogenesis pathway, size, flotation density on a sucrose gradient, lipid composition, sedimentation force, and cargo content[6,8,9]. Presently, these vesicles are isolated by differential and/or density gradient centrifugation which rely primarily on the size or density of the vesicles. Since size and density distribution not discretely unique to each class of membrane vesicles, the present isolation techniques cannot differentiate between the different classes. Although immuno-isolation techniques using antibodies against specific membrane proteins could enhance the specificity of membrane vesicle isolation, no membrane protein has been reported to be unique to a class of membrane vesicles or to a particular cell type. For example, while tetraspanins such as CD9, CD81 have often been used as exosome-associated markers, their ubiquitous distribution over the surface membrane of many cell types suggests a generic association with membrane vesicles. Also, such immuno-isolation techniques cannot distinguish between membrane vesicles, protein complexes or soluble receptors. The lack of specific isolation technique for each class of these membrane vesicles is further exacerbated by a lack of nomenclature standard to unambiguously define each class of membrane vesicle[10]. It is also not clear if the present classification of vesicles describe unique entities.

SUMMARY

According to a 1$^{st}$ aspect of the present invention, we provide a method of detecting pre-eclampsia in an individual. The method may comprise providing a sample of or from the individual. The method may comprise detecting the level of expression, activity or amount of a pre-eclampsia biomarker polypeptide in a microparticle type of the sample.

The pre-eclampsia biomarker polypeptide may be selected from the group consisting of PlGF, FLT1, BNP, ANP, CD9, PAI-1, TGF β, PCT, S100b, TIMP1, CD105 and IL6.

The microparticle type may be selected from a CTB binding microparticle and an Annexin V binding microparticle.

The method may comprise comparing the level of expression, activity or amount of the selected pre-eclampsia biomarker in the same microparticle type of a sample of or from an individual known to be not suffering from pre-eclampsia.

A modulated level of expression, activity or amount of the selected pre-eclampsia biomarker polypeptide may indicate that the individual is suffering from, or is likely to be suffering from, pre-eclampsia.

The method may comprise detecting an elevated level of ANP, CD105, IL6, TIMP1, PlGF, FLT1, BNP, PAI-1, TGF β, PCT or S100b in a CTB binding microparticle. The elevated level may indicate that the individual is suffering from, or is likely to suffer from, pre-eclampsia.

The method may comprise detecting an elevated level of PlGF, FLT1, BNP, PAI-1, TGF β, PCT or S100b in an Annexin V binding microparticle. The elevated level may indicate that the individual is suffering from, or is likely to suffer from, pre-eclampsia.

The method may comprise detecting an elevated level of CD9 in an Annexin V binding microparticle. The elevated level may indicate that the individual is suffering from, or is likely to suffer from, pre-eclampsia.

The method may comprise detecting a lowered level of CD9 in an CTB binding microparticle. The lowered level may indicate that the individual is suffering from, or is likely to suffer from, pre-eclampsia.

The method may comprise detecting a modulated level of expression, activity or amount of one or more further pre-eclampsia biomarker polypeptides. The one or more further pre-eclampsia biomarker polypeptides may be selected from the polypeptides set out in Table 1A, Table 1B and Table 1C. The one or more further pre-eclampsia biomarker polypeptides may be selected from the polypeptides set out in Table 2A, Table 2B and Table 2C. The one or more further pre-eclampsia biomarker polypeptides may be selected from the polypeptides set out in Table 3A and Table 3B. The one or more further pre-eclampsia biomarker polypeptides may be selected from the polypeptides set out in Table 4A and Table 4B.

The method may comprise establishing a profile comprising the expression, activity or amount of a plurality of pre-eclampsia biomarker polypeptides of the individual. The profile may be compared against a profile of an individual known to be not suffering from pre-eclampsia.

The method may comprise a step of normalising the level, concentration or amount of the selected polypeptide between two or more samples. The normalisation may be conducted with reference to BNP, CD9 and/or TIMP-1 polypeptide.

The method may comprise a step of selecting microparticles by size, for example, by size exclusion chromatography. The method may be such that the microparticles comprise CD9+ microparticles. The method may be such that the sample is selected from the group consisting of: urine, blood, tears, saliva, bronchoaveolar fluid, tumoral effusions, epididymal fluid, amniotic fluid and milk. The method may be such that the microparticles comprise microvesicles, exosomes, ectosomes or apoptotic bodies.

There is provided, according to a $2^{nd}$ aspect of the present invention, a method of monitoring the progress of an individual suffering from pre-eclampsia. The method may comprise monitoring the modulation of expression of a pre-eclampsia biomarker polypeptide in a cell, tissue or organ of the individual by a method as described above.

We provide, according to a $3^{rd}$ aspect of the present invention, a method of prognosis of an individual suffering from pre-eclampsia. The method may comprise detecting modulation of expression of a pre-eclampsia biomarker polypeptide in a cell, tissue or organ of the individual by a method as described above.

As a $4^{th}$ aspect of the present invention, there is provided a method of choosing a therapy for an individual suffering from pre-eclampsia. The method may comprise detecting modulation of expression of pre-eclampsia biomarker polypeptide in a cell, tissue or organ of the individual by a method as described above. The method may comprise choosing an appropriate therapy based on the severity of the pre-eclampsia.

We provide, according to a $5^{th}$ aspect of the present invention, a method of determining the likelihood of success of a particular therapy in an individual suffering from pre-eclampsia. The method may comprise comparing the therapy with a therapy determined by a method as described above.

The present invention, in a $6^{th}$ aspect, provides a method of treatment or prevention of pre-eclampsia in a cell, tissue, organ or organism. The method may comprise detecting pre-eclampsia in a cell, tissue, organ or organism by a method according to a method described above. The method may comprise administering a treatment for pre-eclampsia to the cell, tissue, organ or organism. The treatment may comprise an antihypertensive, isradipine, Labetolol, Hydralazine, Nifedipine or magnesium sulfate.

In a $7^{th}$ aspect of the present invention, there is provided a kit for detecting pre-eclampsia in an individual or susceptibility of the individual to pre-eclampsia. The kit may comprise means for detection of pre-eclampsia biomarker polypeptide expression, activity or amount in a microparticle of or from the individual or a sample taken from him or her. The kit may comprise a therapeutic drug for treatment, prophylaxis or alleviation of pre-eclampsia. The therapeutic drug may comprise an antihypertensive, isradipine, Labetolol, Hydralazine, Nifedipine or magnesium sulfate.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; D. M. J. Lilley and J. E. Dahlberg, 1992, *Methods of Enzymology: DNA Structure Part A: Synthesis and Physical Analysis of DNA Methods in Enzymology*, Academic Press; *Using Antibodies: A Laboratory Manual: Portable Protocol NO. I* by Edward Harlow, David Lane, Ed Harlow (1999, Cold Spring Harbor Laboratory Press, ISBN 0-87969-544-7); *Antibodies: A Laboratory Manual* by Ed Harlow (Editor), David Lane (Editor) (1988, Cold Spring Harbor Laboratory Press, ISBN 0-87969-314-2), 1855.

*Handbook of Drug Screening*, edited by Ramakrishna Seethala, Prabhavathi B. Fernandes (2001, New York, N.Y., Marcel Dekker, ISBN 0-8247-0562-9); and *Lab Ref A Handbook of Recipes, Reagents, and Other Reference Tools for Use at the Bench*, Edited Jane Roskams and Linda Rodgers, 2002, Cold Spring Harbor Laboratory, ISBN 0-87969-630-3. Each of these general texts is herein incorporated by reference.

Bound vesicles were extracted with Dynabeads® MyOne Streptavidin T1 magnetic beads. The beads were boiled in standard SDS-PAGE loading buffer and loaded on 4-12% gradient gel and the gel was then silver stained.

Lane 1 was MW marker; lane 2 and 3 were controls without plasma; lane 4 and 5 were CTB- or AV-bound vesicles from plasma; lane 6 and 7 were plasma.

Arrows Indicated Protein Bands Unique to Either CTB- or AV-Bound Vesicles.

Figure 2:
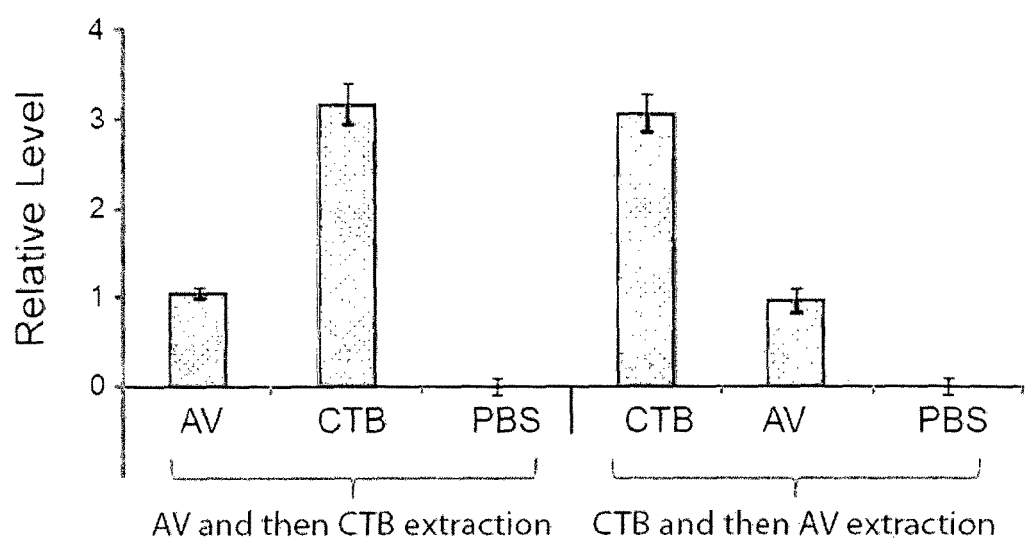

FIG. 2. CTB and AV bind unique vesicles. Plasma from a healthy donor was incubated with biotinylated Cholera Toxin subunit B (CTB) or with biotinylated Annexin V (AV).

Bound vesicles were extracted with Dynabeads® MyOne Streptavidin T1 and then assayed for CD9 by ELISA. The CTB- and AV-depleted plasma were then extracted with AV and CTB, respectively. These second extractions were also assayed for CD9 by ELISA.

The relative level of CD9 in CTB-vesicles before and after extraction with AV, and that in AV-vesicles before and after extraction with CTB were normalized to that in AV-vesicles before CTB extraction.

Figure 3:
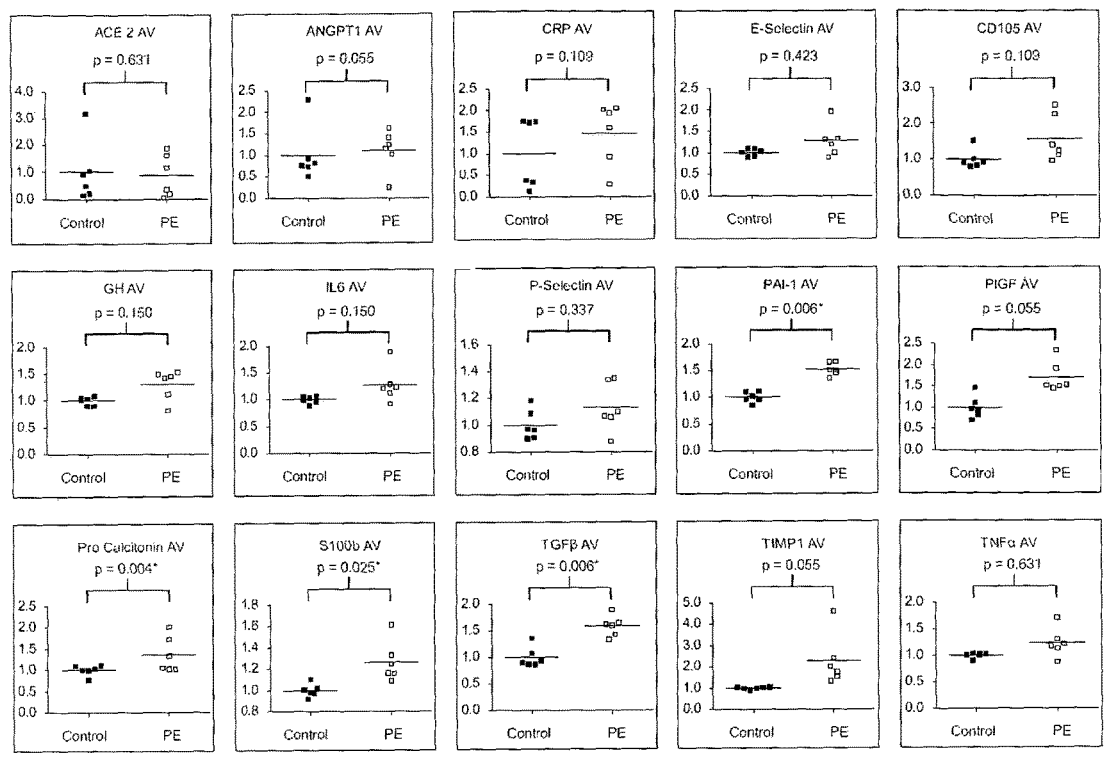

FIG. 3. Assay for candidate PE biomarkers in AV-vesicles by antibody array.

AV-vesicles were isolated from plasma of pre-eclampsia (n=6) and matched healthy pregnant women (n=6). They were then assayed for previously reported pre-eclampsia biomarkers using commercially available antibody arrays. The relative level of each marker was normalized to that in the AV-vesicles of healthy pregnant women.

Figure 4:
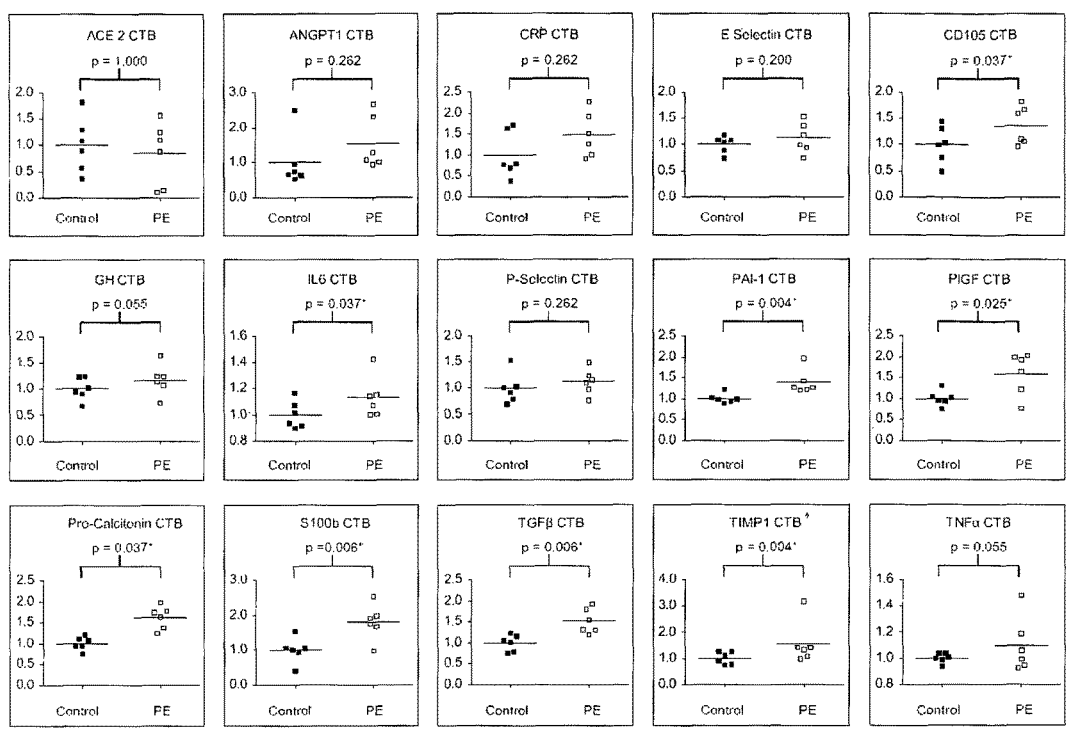

FIG. 4. Assay for candidate PE biomarkers in CTB-vesicles by antibody array.

CTB-vesicles were isolated from plasma of pre-eclampsia (n=6) and matched healthy pregnant women (n=6). They were then assayed for previously reported pre-eclampsia biomarkers using commercially available antibody arrays. The relative level of each marker was normalized to that in the CTB-vesicles of healthy pregnant women.

Figure 5:
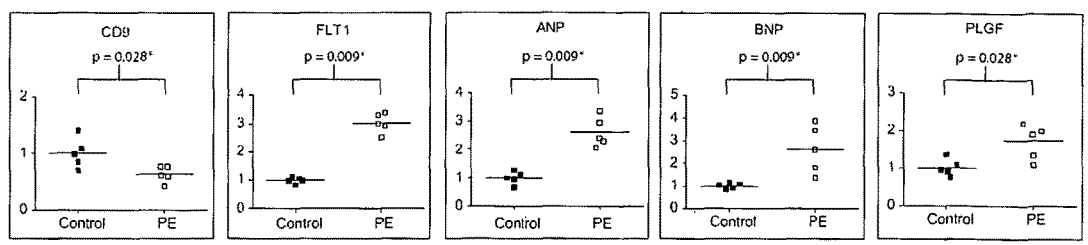
Figure 5:
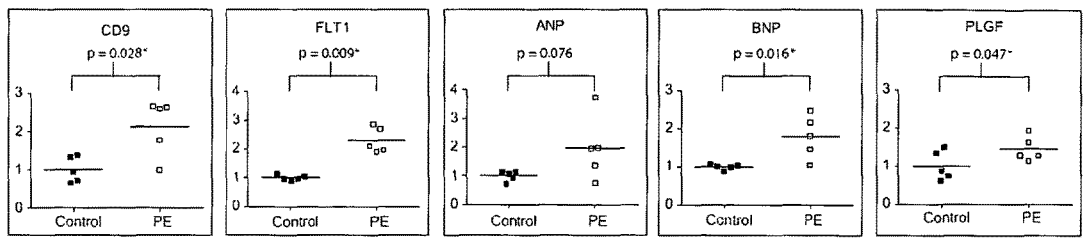

FIG. 5. Assay for candidate PE biomarkers in AV-vesicles by ELISA.

CTB- and AV-vesicles were isolated from plasma of pre-eclampsia (n=5) and matched healthy pregnant women (n=5). They were then assayed for previously reported pre-eclampsia biomarkers by ELISA. The relative level of each marker in CTB- or AV-vesicles was normalized to that in the corresponding vesicles of healthy pregnant women.

Figure 6:
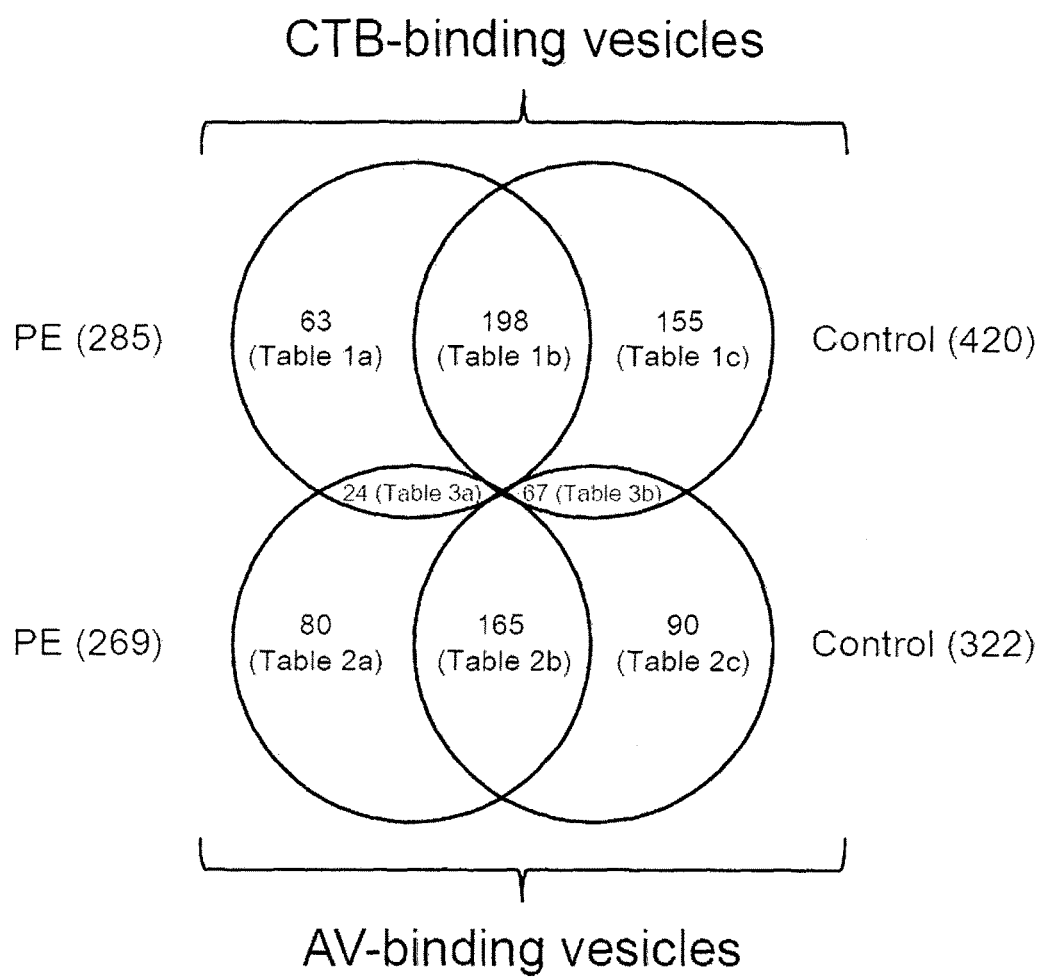

FIG. 6. Relative distribution of proteins in the CTB- and AV-vesicles of PE patients and healthy pregnant women.

The proteome of CTB- and AV-vesicles of PE patients (n=6) and healthy pregnant women (n=6) was analysed by mass spectrometry. The proteins in each of the vesicles were compared and their distribution represented by Venn diagram.

DETAILED DESCRIPTION

In order to circumvent the complex protein milieu of plasma and discover robust predictive biomarkers for pre-eclampsia (PE), we investigate if phospholipid-binding ligands can reduce the milieu complexity by extracting plasma extracellular vesicles for biomarker discovery.

We used Cholera toxin B chain (CTB) and annexin V (AV) which respectively binds GM1 ganglioside and phosphatidylserine to isolate extracellular vesicles from plasma of PE patients and healthy pregnant women. The proteins in the vesicles are identified using ELISA, antibody array and mass spectrometry.

Antibody array and ELISA reveals that that CTB and AV bind two distinct groups of extracellular vesicles.

Surprisingly, we find that that pre-eclampsia patients have elevated levels of CD105, IL6, PlGF, TIMP1 and ANP in CTB- but not AV-vesicles.

We also find that pre-eclampsia patients have elevated levels of PAI-1, PCT, S100b, TGF β FLT1, BNP and PlGF in both CTB- and AV-vesicles.

We find that pre-eclampsia patients have an elevated level of CD9 level in CTB-vesicles but a reduced level of CD9 reduced in AV vesicles.

As shown in Tables 1 to 4 (below), proteome analysis reveals that in CTB-vesicles, 87 and 222 proteins are present only in pre-eclampsia patients and healthy pregnant women respectively. We find that, in AV-vesicles, 104 and 157 proteins are present only in pre-eclampsia and healthy pregnant women respectively.

We therefore demonstrate that the relative levels of proteins or combinations of proteins in annexin V- and CTB-binding sub-fractions in plasma are dependent on the pre-eclampsia status of the individuals. We demonstrate that the relative levels of these proteins can be used to detect pre-eclampsia in an individual, determine whether an individual suffered from pre-eclampsia, predict whether an individual is suffering from, or is likely to suffer from pre-eclampsia, or determine the likelihood that an individual will suffer from pre-eclampsia in the future.

We therefore demonstrate for the first time that the protein cargo of CTB and AV binding extracellular vesicles reflects the disease state of the patient, in particular the pre-eclampsia. We demonstrate the successful use of these two ligands to isolate circulating plasma extracellular vesicles for isolation of biomarkers for diagnosing pre-eclampsia.

Measurement of the relative levels of proteins in annexin V- and CTB-binding subfractions in plasma may therefore be used to assess the health or pathological status (i.e., pre-eclampsia) of individuals.

Detection of Pre-Eclampsia State

We show in the Examples that the expression of pre-eclampsia biomarker polypeptides in microparticle subfractions in individuals suffering from pre-eclampsia is modulated as compared to normal individuals.

We show in the Examples that the levels of ANP, CD105, IL6 and TIMP1 are elevated in CTB binding microparticles of pre-eclampsia patients compared to normal individuals. We also show that, for these biomarkers, their levels in Annexin V binding microparticles do not change between pre-eclampsia patients and normal individuals.

We also show in the Examples that the levels of PlGF, FLT1, BNP, PAI-1, TGF β, PCT and S100b are elevated in CTB binding microparticles of pre-eclampsia patients compared to normal individuals. We also show that, for these biomarkers, their levels in Annexin V binding microparticles are elevated in pre-eclampsia patients compared to normal individuals.

We further show in the Examples that the level of CD9 is lowered in CTB binding microparticles of pre-eclampsia patients compared to normal individuals. We also show that, for this biomarker, its level in Annexin V binding microparticles of pre-eclampsia patients is elevated compared to normal individuals.

Accordingly, we provide for a method of diagnosis of pre-eclampsia in an individual, comprising detecting modulation of expression of a pre-eclampsia biomarker polypeptide, such as up-regulation or down-regulation of expression of pre-eclampsia biomarker polypeptide, in a CTB binding microparticle, or an Annexin V binding microparticle, or both, in or of the individual.

Detection of pre-eclampsia biomarker polypeptide expression, activity or amount may be used to provide a method of determining the pre-eclampsia state of a cell, tissue, organ or organism.

Elevated Levels of ANP, CD105, IL6, TIMP1, PlGF, FLT1, BNP, PAI-1, TGF β, PCT or S100 b in CTB Binding Microparticles A pre-eclampsia cell, tissue, organ or organism may be one with higher levels of ANP, CD105, IL6, TIMP1, PlGF, FLT1, BNP, PAI-1, TGF β, PCT or S100b polypeptide expression, activity or amount in a CTB binding microparticle, compared to a normal cell, tissue, organ or organism.

We therefore provide a method comprising establishing the level of expression, activity or amount of a pre-eclampsia biomarker polypeptide selected from the group consisting of: ANP, CD105, IL6, TIMP1, PlGF, FLT1, BNP, PAI-1, TGF β, PCT or S100b in a CTB binding microparticle of an individual. This level of expression, activity or amount is then compared to the expression, activity or amount of the pre-eclampsia biomarker polypeptide in a CTB binding microparticle of a normal individual or an individual known not to be suffering from pre-eclampsia.

We provide a method of detecting pre-eclampsia in a cell, tissue, organ or organism, the method comprising detecting an elevated level of expression, activity or amount of a pre-eclampsia biomarker polypeptide selected from the group consisting of: ANP, CD105, IL6, TIMP1, PlGF, FLT1, BNP, PAI-1, TGF β, PCT or S100b in a CTB binding microparticle of an individual compared to the level of expression, activity or amount of the pre-eclampsia biomarker polypeptide in a CTB binding microparticle of a normal individual. An elevated level of expression, activity or amount of the pre-eclampsia biomarker polypeptide indicates that the individual from whom the sample is taken is suffering from or is likely to suffer from pre-eclampsia.

Elevated Levels of PlGF, FLT1, BNP, PAI-1, TGF β, PCT or S100b in Annexin V Binding Microparticles A pre-eclampsia cell, tissue, organ or organism may also be one with higher levels of PlGF, FLT1, BNP, PAI-1, TGF β, PCT or S100b polypeptide expression, activity or amount in an Annexin V binding microparticle, compared to a normal cell, tissue, organ or organism.

We therefore provide a method comprising establishing the level of expression, activity or amount of a pre-eclampsia biomarker polypeptide selected from the group consisting of: PlGF, FLT1, BNP, PAI-1, TGF β, PCT or S100b in an Annexin V binding microparticle of an individual. This level of expression, activity or amount is then compared to the expression, activity or amount of the pre-eclampsia biomarker polypeptide in a normal individual or an individual known not to be suffering from pre-eclampsia.

We provide a method of detecting pre-eclampsia in a cell, tissue, organ or organism, the method comprising detecting an elevated level of expression, activity or amount of a pre-eclampsia biomarker polypeptide selected from the group consisting of: PlGF, FLT1, BNP, PAI-1, TGF β, PCT or S100b in an Annexin V binding microparticle of an individual compared to the level of expression, activity or amount of the pre-eclampsia biomarker polypeptide in a normal individual. An elevated level of expression, activity or amount of the pre-eclampsia biomarker polypeptide indicates that the individual from whom the sample is taken is suffering from or is likely to suffer from pre-eclampsia.

Elevated Levels of CD9 in Annexin V Binding Microparticles

A pre-eclampsia cell, tissue, organ or organism may also be one with higher levels of CD9 polypeptide expression, activity or amount in an Annexin V binding microparticle, compared to a normal cell, tissue, organ or organism.

We therefore provide a method comprising establishing the level of expression, activity or amount of a pre-eclampsia biomarker polypeptide consisting of CD9 in an Annexin V binding microparticle of an individual. This level of expression, activity or amount is then compared to the expression, activity or amount of the pre-eclampsia biomarker polypeptide in a normal individual or an individual known not to be suffering from pre-eclampsia.

We provide a method of detecting pre-eclampsia in a cell, tissue, organ or organism, the method comprising detecting an elevated level of expression, activity or amount of a pre-eclampsia biomarker polypeptide consisting of CD9 in an Annexin V binding microparticle of an individual compared to the level of expression, activity or amount of the pre-eclampsia biomarker polypeptide in a normal individual. An elevated level of expression, activity or amount of the pre-eclampsia biomarker polypeptide indicates that the individual from whom the sample is taken is suffering from or is likely to suffer from pre-eclampsia.

Lowered Levels of CD9 in CTB Binding Microparticles

A pre-eclampsia cell, tissue, organ or organism may also be one with lower levels of CD9 polypeptide expression, activity or amount in an CTB binding microparticle, compared to a normal cell, tissue, organ or organism.

We therefore provide a method comprising establishing the level of expression, activity or amount of a pre-eclampsia biomarker polypeptide consisting of CD9 in a CTB binding microparticle of an individual. This level of expression, activity or amount is then compared to the expression, activity or amount of the pre-eclampsia biomarker polypeptide in a CTB binding microparticle of a normal individual or an individual known not to be suffering from pre-eclampsia.

We provide a method of detecting pre-eclampsia in a cell, tissue, organ or organism, the method comprising detecting a lowered level of expression, activity or amount of a pre-eclampsia biomarker polypeptide consisting of CD9 in a CTB binding microparticle of an individual compared to the level of expression, activity or amount of the pre-eclampsia biomarker polypeptide in a CTB binding microparticle of a normal individual. A lowered level of expression, activity or amount of the pre-eclampsia biomarker polypeptide indicates that the individual from whom the sample is taken is suffering from or is likely to suffer from pre-eclampsia.

Such detection may also be used to determine whether a cell, tissue, organ or organism will become or is likely to become a pre-eclampsia cell, tissue, organ or organism.

Thus, detection of any of: an elevated level of ANP, CD105, IL6, TIMP1, PlGF, FLT1, BNP, PAI-1, TGF β, PCT or S100b in a CTB binding microparticle; an elevated level of a PlGF, FLT1, BNP, PAI-1, TGF β, PCT or S100b protein in an Annexin V binding microparticle; an elevated level of CD9 in an Annexin V binding microparticle; or a lowered level of CD9 in a CTB binding microparticle may indicate that the cell, tissue, organ or organism is likely to be or become a pre-eclampsia cell, tissue, organ or organism.

We provide methods of detecting a pre-eclampsia state of a cell, tissue, organ or organism. The methods make use of pre-eclampsia biomarker polypeptides, described below.

The method may be such that the state of the cell, tissue, organ or organism comprises a state of suffering from pre-eclampsia, a state of poor prognosis of pre-eclampsia, a state of recovery from pre-eclampsia, a state of good prognosis of pre-eclampsia or a healthy state.

In addition to detection of pre-eclampsia state, we also disclose methods of establishment of pre-eclampsia state, methods of monitoring of changes of pre-eclampsia state, methods of detection and treatment of pre-eclampsia in an individual and methods of monitoring of recovery from pre-eclampsia.

As described above, our methods may generally comprise establishing, for a sample of microparticles from the cell, tissue, organ or organism, an amount or level of a selected pre-eclampsia biomarker polypeptide in a particular type of microparticles. The amount or level of the pre-eclampsia biomarker polypeptide in the type of microparticle is then compared with the amount or level of the pre-eclampsia biomarker polypeptide in the same of microparticle in an individual known not to be suffering from pre-eclampsia. Such a method is described in further detail below.

Alternatively, or in addition, our methods may comprise establishing, for a sample of microparticles from the cell, tissue, organ or organism, a ratio of the amount of a selected pre-eclampsia biomarker polypeptide in a first type of microparticles to the amount of the selected pre-eclampsia biomarker polypeptide in a second type of microparticles. This method is described in further detail below.

We also disclose a combination of these methods for the detection of a pre-eclampsia state.

The microparticle type may comprise CTB binding microparticles, described below. The microparticle type may comprise Annexin V binding microparticles, also described below.

Pre-Eclampsia Biomarkers

We describe a pre-eclampsia biomarker. The pre-eclampsia biomarker may comprise a nucleic acid or a polypeptide.

In some embodiments, the methods and compositions described here make use of pre-eclampsia biomarker polypeptides.

The pre-eclampsia biomarker polypeptide may comprise PlGF, FLT1, BNP, ANP, CD9, PAI-1, TGF β, PCT, S100b, TIMP1, CD105 or IL6.

Group I Pre-Eclampsia Biomarker Polypeptides

Group I comprises polypeptides whose levels are elevated in CTB binding microparticles of pre-eclampsia patients compared to normal individuals, and for whose levels there is no change in Annexin V binding microparticle levels between pre-eclampsia patients and normal individuals.

The pre-eclampsia biomarker polypeptide may be selected from a polypeptide set out in Group. I, i.e.: ANP, CD105, IL6 and TIMP1.

Group II Pre-Eclampsia Biomarker Polypeptides

Group II comprises polypeptides whose levels are elevated in CTB binding microparticles of pre-eclampsia patients compared to normal individuals, and whose levels are elevated in Annexin V binding microparticles of pre-eclampsia patients compared to normal individuals.

The pre-eclampsia biomarker polypeptide may be selected from a polypeptide set out in Group II, i.e. PlGF, FLT1, BNP, PAI-1, TGF β, PCT and S100b.

Group III Pre-Eclampsia Biomarker Polypeptide

Group III comprises a polypeptide whose level is lowered in CTB binding microparticles of pre-eclampsia patients compared to normal individuals, and whose level is elevated in Annexin V binding microparticles of pre-eclampsia patients compared to normal individuals.

The pre-eclampsia biomarker polypeptide may be selected from a polypeptide set out in Group III, i.e.: CD9.

PlGF

PlGF may comprise a polypeptide with GenBank Accession Number NP_002623.2.

A representative sequence of PlGF is:

```
                                               (SEQ ID NO: 1)
LPAVPPQQWALSAGNGSSEVEVVPFQEVWGRSYCRALERLVDVVS

EYPSEVEHMFSPSCVSLLRCTGCCGDENLHCVPVETANVTMQLLK

IRSGDRPSYVELTFSQHVRCECRHSPGRQSPDMPGDFRADAPSFL

PPRRSLPMLFRMEWGCALTGSQSAVWPSSPVPEEIPRMHPGRNGK

KQQRKPLREKMKPERCGDAVPRR
```

Assays for PlGF are known in the art, and include for example Human PlGF Quantikine ELISA Kit (Product Code: DPG00, Vendor: Rndsystems, found on the worldwide web at rndsystems.com/Products/DPG00).

FLT1

FLT1 is also known as VEGFR and may comprise a polypeptide with GenBank Accession Number NP_002010.2.

A representative sequence of FLT1 is:

```
                                               (SEQ ID NO: 2)
SSSGSKLKDPELSLKGTQHIMQAGQTLHLQCRGEAAHKWSLPEMV

SKESERLSITKSACGRNGKQFCSTLTLNTAQANHTGFYSCKYLAV

PTSKKKETESAIYIFISDTGRPFVEMYSEIPEIIHMTEGREINIP

CRVTSPNITVTLKKFPLDTLIPDGKRIIWDSRKGFIISNATYKEI

GLLTCEATVNGHLYKTNYLTHRQTNTIIDVQISTPRPVKLLRGHT
```

Assays for FLT1 are known in the art, and include for example Human sVEGF R1/Flt-1 Quantikine ELISA Kit (Product Code: DVR100B, Vendor: Rndsystems, found on the worldwide web at mdsystems.com/Products/DVR100B)

BNP

BNP may comprise a polypeptide with GenBank Accession Number NP_002512.1.

A representative sequence of BNP is:

```
                                               (SEQ ID NO: 3)
      SPKMVQGSGCFGRKMDRISSSSGLGCKVLRRH
```

Assays for BNP are known in the art, and include for example Human BNP EIA (Product Code: EIA-BNP, Vendor: RayBiotech, found on the worldwide web at raybiotech.com/human-bnp-eia-kit.html)

ANP

ANP may comprise a polypeptide with GenBank Accession Number NP_006163.1.

A representative sequence of ANP is:

(SEQ ID NO: 4)
MSSFSTTTVSFLLLLAFQLLGQTRANPMYNAVSNADLMDFKNLLD

HLEEKMPLEDEVVPPQVLSEPNEEAGAALSPLPEVPPWTGEVSPA

QRDGGALGRGPWDSSDRSALLKSKLRALLTAPRSLRRSSCFGGRM

DRIGAQSGLGCNSFRYRS

Assays for ANP are known in the art, and include for example Human ANP EIA (Product Code: EIA-ANP, Vendor: RayBiotech, found on the worldwide web at raybiotech.com/human-anp-eia-kit.html)

CD9

CD9 may comprise a polypeptide with GenBank Accession Number NP_001760.1.

A representative sequence of CD9 is:

(SEQ ID NO: 5)
AIETAAAIWGYSHKDEVIKEVQEFYKDTYNKLKTKDEPQRETLKA

IHYALNCCGLAGGVEQFISDICPKKDVLETFTVKSCPDAIKEVFD

NKFHIIGAVGIGIAVVMIFG

Assays for CD9 are known in the art, and include for example CD9 ELISA Kit (Product Code: ABIN812211, Vendor: antibodies-online, found on the worldwide web at antibodies-online.com/kit/812211/CD9+CD9+ELISA/?utm_source=partner&utm_medium=antibodyresource&utm_campaign=listing&utm_content=105)

PAI-1

PAI-1 may comprise a polypeptide with GenBank Accession Number NP_000593.1.

A representative sequence of PAI-1 is:

(SEQ ID NO: 6)
VHHPPSYVAHLASDFGVRVFQQVAQASKDRNVVFSPYGVASVLAM

LQLTTGGETQQQIQAAMGFKIDDKGMAPALRHLYKELMGPWNKDE

ISTTDAIFVQRDLKLVQGFMPHFFRLFRSTVKQVDFSEVERARFI

Assays for PAI-I are known in the art, and include for example Human Serpin El/PAI-1 Quantikine ELISA Kit (Product Code: D6050, Vendor: Rndsystems, found on the worldwide web at rndsystems.com/Products/DSE100).

TGFβ

TGFβ may comprise a polypeptide with GenBank Accession Number NP_000651.3.

A representative sequence of TGFβ is:

(SEQ ID NO: 7)
LSTCKTIDMELVKRKRIEAIRGQILSKLRLASPPSQGEVPPGPLP

EAVLALYNSTRDRVAESAEPEPEPEADYYAKEVTRVLMVETHNEI

YDKFKQSTHSIYMFFNTSELREAVPEPVLLSRAELRLLRLKLKVE

QHVELYQKYSNNSWRYLSNRLLAPSDSPEWLSFDVTGVVRQWLSR

GGEIEGFRLSAHCSCDSRDNTLQVDINGFTTGRRGDLATIHGMNR

PFLLLMATPLERAQHLQSSRHRR

Assays for TGFβ are known in the art, and include for example Human TGF-beta 1 ELISA (Product Code: ELH-TGFb1, Vendor: RayBiotech, found on the worldwide web at raybiotech.com/human-tgf-beta-1-elisa-kit-for-serum-plasma-cell-culture-supernatants-and-urine.html)

PCT

PCT may comprise a polypeptide with GenBank Accession Number NP_001029124.1.

A representative sequence of PCT is:

(SEQ ID NO: 8)
APFRSALESSPADPATLSEDEARLLLAALVQNYVQMKASELEQEQ

EREGSRIIAQ

Assays for PCT are known in the art, and include for example Human Procalcitonin ELISA (Product Code: ELH-PROCALC, Vendor: RayBiotech, found on the worldwide web at raybiotech.com/human-procalcitonin-elisa-kit-for-serum-plasma-cell-culture-supernatant-and-urine.html)

S100b

S100b may comprise a polypeptide with GenBank Accession Number NP_006263.1.

A representative sequence of S100b is:

(SEQ ID NO: 9)
SELEKAMVALIDVFHQYSGREGDKHKLKKSELKELINNELSHFLE

EIKEQEVVDKVMETLDNDGDGECDFQEFMAFVAMVTTACHEFFEH

E

Assays for S100b are known in the art, and include for example Human S100B ELISA (Product Code: EZHS100B-33K, Vendor: Merck Millipore, found on the worldwide web at millipore.com/catalogue/item/ezhs100b-33k)

TIMP1

TIMP1 may comprise a polypeptide with GenBank Accession Number NP_003245.1.

A representative sequence of TIMP1 is:

(SEQ ID NO: 10)
TDQLLQGSEKGFQSRHLACLPREPGLCTWQSLRSQIA

Assays for TIMP1 are known in the art, and include for example Human TIMP-1 Quantikine ELISA Kit (Product Code: DTM100, Vendor: Rndsystems, found on the worldwide web at rndsystems.com/Products/DTM100)

CD105

CD105 may comprise a polypeptide with GenBank Accession Number NP_001108225.1.

A representative sequence of CD105 is:

(SEQ ID NO: 11)
TVHCDLQPVGPERGEVTYTTSQVSKGCVAQAPNAILEVHVLFLEF

PTGPSQLELTLQASKQNGTWPREVLLVLSVNSSVELHLQALGIPL

HLAYNSSLVTFQEPPGVNTTELPSFPKTQILEWAAERGPITSAAE

LNDPQSILLRLGQAQGSLSFCMLEASQDMGRTLEWRPRTPALVRG

CHLEGVAGHKEAHILRVLPGHSAGPRTVTVKVELSCAPGDLDAVL

ILQGPPYVSWLIDANHNMQIWTTGEYSFKIFPEKNIRGFKLPDTP

QGLLGEARMLNASIVASFVELPLASIVSLH

Assays for CD105 are known in the art, and include for example Human Endoglin/CD105 Quantikine ELISA Kit (Product Code: DNDG00, Vendor: Rndsystems, found on the worldwide web at rndsystems.com/Products/DNDG00)

IL6

IL6 may comprise a polypeptide with GenBank Accession Number NP_000591.1.

A representative sequence of IL6 is:

(SEQ ID NO: 12)
VPPGEDSKDVAAPHRQPLTSSERIDKQTRYILDGISALRKETCNK

SNMCESSKEALAENNLNLPKMAEKDGCFQSGFNEETCLVKIITGL

LEFEVYLEYLQNRFESSEEQARAVQMSTKVLIQFLQKKAKNLDAI

TTPDPTTNASLLTKLQAQNQWLQDMTTHLILRSFKEFLQSSLRAL

RQM

Assays for IL6 are known in the art, and include for example Human IL-6 Quantikine ELISA Kit (Product Code: D6050, Vendor: Rndsystems, found on the worldwide web at rndsystems.com/Products/D6050)

Other Pre-Eclampsia Biomarker Polypeptides

The pre-eclampsia biomarker polypeptide may be selected from the group consisting of the polypeptides set out in Table 1, Table 2, Table 3 and Table 4.

The pre-eclampsia biomarker polypeptide may be selected from a polypeptide set out in Table 1A, Table 1B and Table 1C.

The pre-eclampsia biomarker polypeptide may be selected from a polypeptide set out in Table 2A, Table 2B and Table 2C.

The pre-eclampsia biomarker polypeptide may be selected from a polypeptide set out in Table 3A and Table 3B.

The pre-eclampsia biomarker polypeptide may be selected from a polypeptide set out in Table 4A and Table 4B.

Microparticle Types

The methods and compositions described here make use of microparticle types, such as a first microparticle type and/or a second microparticle type. These methods are described in more detail elsewhere in this document.

Such microparticle types may generally comprise one or more subfractions of the microparticles present in a sample.

CTB Binding Microparticles

The first type of microparticles may comprise GM1 gangliosides. They may therefore be known as "GM1 ganglioside microparticles".

The first type of microparticles may be capable of binding to Cholera Toxin B (CTB), referred to as "CTB binding microparticles" for convenience.

For convenience, we refer to the presence, amount, mass or number etc of the pre-eclampsia biomarker polypeptide in the first type of microparticle, where these are CTB binding microparticles, as "CTB binding microparticle polypeptide".

Methods of fractionating samples to produce CTB binding microparticles are described in detail elsewhere in this document. CTB binding microparticles may be prepared from plasma (or other fluids) using the following sample protocol:

Step 1. 10 µL plasma are incubated with 0.1 µg biotinylated Cholera Toxin subunit B (CTB) (SBL Vaccin AB) in 100 µL PBS pH 7.4 for 1 hour at 37° C. with shaking at 800 rpm.

Step 2. In the meantime, 100 µL of Dynabeads® M-280 Streptavidin (Invitrogen) are washed three times with 100 µL PBS.

Step 4. After the last wash, the plasma-CTB reaction mix is added to the washed beads and incubated with shaking at 800 rpm for 30 minutes.

Step 4. The beads are immobilised with a magnet and the supernatant is removed.

Step 5. The beads are then washed thrice with 200 µL PBS and the washes are removed each time after immobilizing the beads with a magnet.

Annexin V Binding Microparticles

The second type of microparticles may be microparticles which comprise exposed phosphotidylserine. The second type of microparticles may be capable of binding to Annexin V (referred to as "Annexin V binding microparticles" or "AV-binding microvesicles" for convenience).

Similarly, for convenience, we refer to the presence, amount, mass or number etc of the pre-eclampsia biomarker polypeptide in the second type of microparticle, where these are Annexin V binding microparticles, as "Annexin V binding microparticle polypeptide".

Methods of fractionating samples to produce Annexin V binding microparticles are described in detail elsewhere in this document. Annexin V binding microparticles may be prepared from plasma (or other fluids) using the following sample protocol:

Step 1. 10 µL plasma are incubated with 0.1 µg biotinylated Annexin V (AV) (BioVision) in 100 µL, PBS pH 7.4 for 1 hour at 37° C. with shaking at 800 rpm.

Step 2. In the meantime, 100 µL of Dynabeads® M-280 Streptavidin (Invitrogen) are washed three times with 100 µL PBS.

Step 4. After the last wash, the plasma-AV reaction mix is added to the washed beads and incubated with shaking at 800 rpm for 30 minutes.

Step 4. The beads are immobilised with a magnet and the supernatant is removed.

Step 5. The beads are then washed thrice with 200 µl PBS and the washes are removed each time after immobilizing the beads with a magnet.

Size Selection

The methods described above for preparing CTB and Annexin V binding microparticles may further comprise a step of selecting microparticles by size.

The size selection step may comprise size exclusion chromatography. Where this is done, the size selection step may be conducted prior to the first step above.

Detection of Pre-Eclampsia State by Polypeptide Levels

We provide for the use of PlGF, FLT1, BNP, ANP, CD9, PAI-1, TGF β, PCT, S100b, TIMP1, CD105 and IL6, particularly a level of expression, activity or amount of PlGF, FLT1, BNP, ANP, CD9, PAI-1, TGF β, PCT, S100b, TIMP1, CD105 and IL6 in a microparticle type, as a biomarker for pre-eclampsia.

We describe a method of detecting pre-eclampsia in a cell, tissue, organ or organism, the method comprising detecting modulation of expression, activity or amount of PlGF, FLT1, BNP, ANP, CD9, PAI-1, TGF β, PCT, S100b, TIMP1, CD105 and IL6 in a CTB binding microparticle or an Annexin V binding microparticle of the cell, tissue, organ or organism.

Elevated Group I Polypeptide in CTB Binding Microparticles

A method of detecting a pre-eclampsia state of a cell, tissue, organ or organism may comprise establishing, for a sample of microparticles from the cell, tissue, organ or organism, an amount or level of a pre-eclampsia biomarker polypeptide selected from a Group I protein in CTB binding microparticles of that sample.

Detection of an elevated level of a Group I polypeptide in CTB binding microparticles indicates that the cell, tissue, organ or organism has a pre-eclampsia state.

Elevated Group II Polypeptide in CTB Binding Microparticles

A method of detecting a pre-eclampsia state of a cell, tissue, organ or organism may comprise establishing, for a sample of microparticles from the cell, tissue, organ or organism, an amount or level of a pre-eclampsia biomarker polypeptide selected from a Group II protein in CTB binding microparticles of that sample.

Detection of an elevated level of a Group II polypeptide in CTB binding microparticles indicates that the cell, tissue, organ or organism has a pre-eclampsia state.

Elevated Group II Polypeptide in Annexin V Binding Microparticles

A method of detecting a pre-eclampsia state of a cell, tissue, organ or organism may comprise establishing, for a sample of microparticles from the cell, tissue, organ or organism, an amount or level of a pre-eclampsia biomarker polypeptide selected from a Group II protein in Annexin V binding microparticles of that sample.

Detection of an elevated level of a Group II polypeptide in Annexin V binding microparticles indicates that the cell, tissue, organ or organism has a pre-eclampsia state.

Elevated Group III Polypeptide in Annexin V Binding Microparticles

A method of detecting a pre-eclampsia state of a cell, tissue, organ or organism may comprise establishing, for a sample of microparticles from the cell, tissue, organ or organism, an amount or level of a pre-eclampsia biomarker polypeptide selected from a Group III protein in Annexin V binding microparticles of that sample.

Detection of an elevated level of a Group III polypeptide in Annexin V binding microparticles indicates that the cell, tissue, organ or organism has a pre-eclampsia state.

Lowered Group III Polypeptide in CTB Binding Microparticles

A method of detecting a pre-eclampsia state of a cell, tissue, organ or organism may comprise establishing, for a sample of microparticles from the cell, tissue, organ or organism, an amount or level of a pre-eclampsia-biomarker polypeptide selected from a Group III protein in CTB binding microparticles of that sample.

Detection of an lowered level of a Group III polypeptide in CTB binding microparticles indicates that the cell, tissue, organ or organism has a pre-eclampsia state.

Sample Protocol

The following sample protocol may be used to detect a pre-eclampsia state using the amount or level of a pre-eclampsia biomarker polypeptide:

- Blood is drawn from a patient and collected in a tube with anti-coagulant e.g. EDTA, heparin or citrate.
- Plasma is prepared using standard clinical laboratory protocols.
- The plasma is incubated with either biotinylated CTB or biotinylated AV.
- CTB- or AV-binding vesicles are extracted using strepavidin-conjugated magnetic beads.
- The magnetic beads are treated with a 0.1% TritonX-100 phosphate buffer solution (PBS) to solubilise the vesicles.
- The solubilised vesicles are assayed for each of the following proteins: PlGF, FLT1, BNP, ANP, CD9, PAI-1, TGF β, PCT, S100b, TIMP1 using commercially available sandwich ELISA kits (see section "Pre-Eclampsia Biomakers" elsewhere in this document).

These kits can determine the amount (protein mass) of each protein in either CTB- or AV-binding vesicles extracted from plasma. For each patient, the mass of protein X in CTB- or AV binding vesicles in an unit (ml) plasma is thereby determined.

This level is then compared to a previously determined normal range. This normal range can be established as per the establishment of a normal range for any biomarker by measuring the level in a population of undiseased persons. This population mirrors the demographic, gender, age, race and gestation of the diseased population.

The normal distribution range of each protein is the range that covers 99.5% of the undiseased cohort.

Detection by Annexin V to CTB Ratio

We describe a method of detecting a pre-eclampsia state of a cell, tissue, organ or organism. The method may comprise establishing, for a sample of microparticles from the cell, tissue, organ or organism, a ratio.

The ratio may be of (a) a pre-eclampsia biomarker polypeptide in microparticles which bind to Cholera Toxin B (CTB) ("CTB microparticle polypeptide") to (b) the pre-eclampsia biomarker polypeptide in microparticles which bind to Annexin V ("Annexin V microparticle polypeptide").

The ratio, which may be termed the CTB microparticle polypeptide to Annexin V microparticle polypeptide ratio, may be indicative of the pre-eclampsia state of the cell, tissue, organ or organism.

The method may therefore comprise establishing, for a sample of microparticles from the cell, tissue, organ or organism, a ratio of the amount of a selected pre-eclampsia biomarker polypeptide in CTB binding microparticles to the amount of the selected pre-eclampsia biomarker polypeptide in Annexin V binding microparticles.

The ratio may be a ratio of the amount of the pre-eclampsia biomarker polypeptide in the CTB binding microparticles as compared to the amount of the pre-eclampsia biomarker polypeptide in Annexin V binding microparticles, i.e., between the two types of microparticles.

For convenience, we refer to the ratio of the above as a "CTB binding microparticle polypeptide to Annexin V binding microparticle polypeptide ratio".

The microparticles which bind to Cholera Toxin B (CTB) may comprise GM1 gangliosides.

In particular, we provide for a method of monitoring the pre-eclampsia state of a cell, tissue, organ or organism, the method comprising establishing, for a sample of microparticles from the cell, tissue, organ or organism, a ratio of: (a) a selected pre-eclampsia biomarker polypeptide in microparticles which bind to Cholera Toxin B (CTB) ("CTB binding microparticle polypeptide"); to (b) the selected pre-eclampsia biomarker polypeptide in microparticles which comprise exposed phosphotidylserine, preferably which bind to Annexin V ("Annexin V binding microparticle polypeptide"); in which the (a) to (b) ratio ("CTB binding microparticle polypeptide to Annexin V binding microparticle polypeptide ratio") so established is indicative of the pre-eclampsia state of the cell, tissue, organ or organism.

The pre-eclampsia biomarker polypeptide may be selected from the polypeptides disclosed in the section "Pre-eclampsia Biomarker Polypeptide" above.

The pre-eclampsia biomarker polypeptide may comprise a Group I polypeptide. The pre-eclampsia biomarker polypeptide may be selected from the group consisting of: ANP, CD105, IL6 and TIMP1.

The pre-eclampsia biomarker polypeptide may comprise a Group II polypeptide. The pre-eclampsia biomarker polypeptide may be selected from the group consisting of: PlGF, FLT1, BNP, PAI-1, TGF β, PCT and S100b.

The pre-eclampsia biomarker polypeptide may comprise a Group III polypeptide. The pre-eclampsia biomarker polypeptide may comprise CD9.

We describe a method of monitoring a pre-eclampsia state of a cell, tissue, organ or organism, comprising the method set out above.

We further provide a method for establishing that a cell, tissue, organ or organism is in a pre-eclampsia state. The method may comprise comparing a CTB binding microparticle polypeptide to Annexin V binding microparticle polypeptide ratio of the cell, tissue, organ or organism (or a profile comprising such a ratio) with a CTB binding microparticle polypeptide to Annexin V binding microparticle polypeptide ratio (or a profile comprising such a ratio) of a cell, tissue, organ or organism known to be in a pre-eclampsia state.

The method may comprise selecting microparticles in the sample which bind to Cholera Toxin subunit B (CTB). The method may comprise selecting microparticles in the sample which comprise GM1 gangliosides.

The method may comprise selecting microparticles in the sample which bind to Annexin V. The method may comprise selecting microparticles in the sample which comprise exposed phosphatidylserine.

The method may further comprise a step of selecting microparticles by size. The size selection step may comprise size exclusion chromatography. The size selection step may take place prior to the ratio-determining step.

In addition to, or instead of, using a single pre-eclampsia biomarker polypeptide, combinations of selected pre-eclampsia biomarker polypeptides may also be used. Accordingly, where we refer to a pre-eclampsia biomarker polypeptide (e.g., by comparison of amount to establish ratios), such reference should be taken to include reference to combinations of pre-eclampsia biomarker polypeptides, for example by establishing or comparing amounts of combinations of pre-eclampsia biomarker polypeptides.

It will therefore be appreciated that when we describe our method as using "a selected pre-eclampsia biomarker polypeptide", more than one pre-eclampsia biomarker polypeptide may be used as well.

The method may comprise establishing a profile comprising a plurality of CTB microparticle polypeptide to Annexin V microparticle polypeptide ratios for a plurality of selected polypeptide species, each indicative of the state of the cell, tissue, organ or organism. The plurality of selected polypeptide species may comprise any one or more polypeptides from Groups I, II and III. The plurality of polypeptide species may comprise any one or more polypeptides set out in Tables 1 to 4. The plurality of polypeptide species may comprise one or more polypeptides from Groups I, II and III and the polypeptides set out in Tables 1 to 4.

The pre-eclampsia biomarker polypeptide may comprise a Group I polypeptide selected from ANP, CD105, IL6 or TIMP1.

The CTB microparticle polypeptide to Annexin V microparticle polypeptide ratio of the Group I polypeptide may be higher in a pre-eclampsia state compared to a healthy state.

The pre-eclampsia biomarker polypeptide may comprise a Group II polypeptide selected from PlGF, FLT1, BNP, PAI-1, TGF β, PCT and S100b.

The CTB microparticle polypeptide to Annexin V microparticle polypeptide ratio of the Group II polypeptide may be modulated in a pre-eclampsia state compared to a healthy state.

The pre-eclampsia biomarker polypeptide may comprise a Group III polypeptide, i.e., CD9.

The CTB microparticle polypeptide to Annexin V microparticle polypeptide ratio of the Group II polypeptide may be lower in a pre-eclampsia state compared to a healthy state.

Where determination of an "amount" of a polypeptide is referred, it should be understood to extend to the determination or establishment of the mass, number concentration etc of the polypeptide.

Where reference is made to an amount or ratio of a polypeptide (or an amount or ratio of combination), being "higher" or "elevated" in a first state than a second state, this may be taken to mean that the amount or ratio is of a larger value in the first state compared to the second state to a statistically significant degree, i.e., with a p value <0.01.

For example, an elevated level with reference to either absolute protein mass or ratio may be taken to mean that the level is higher than the level in 99.5% of patients without pre-eclampsia.

Where reference is made to an amount or a ratio of a polypeptide (or an amount or ratio of combination), being "lower" or "lowered" in a first state than a second state, this may be taken to mean that the amount or ratio is of a smaller value in the first state compared to the second state to a statistically significant degree, i.e., with a p value <0.01.

For example, a lowered level with reference to either absolute protein mass or ratio may be taken to mean that the level is lower than the level in 99.5% of patients without pre-eclampsia.

The ratio so established may be indicative of the pre-eclampsia state of the cell, tissue, organ or organism.

The method may be such that the microparticles comprise CD9+ microparticles. The method may be such that the microparticles comprise microvesicles, exosomes, ectosomes or apoptotic bodies.

The method may be such that the pre-eclampsia state of the cell, tissue, organ or organism comprises a state of suffering from pre-eclampsia, a state of poor prognosis of pre-eclampsia, a state of recovery from pre-eclampsia, a state of good prognosis of pre-eclampsia or a healthy state.

The method may be such that the sample is selected from the group consisting of: urine, blood, tears, saliva, bronchoaveolar fluid, tumoral effusions, epididymal fluid, amniotic fluid and milk.

The method may further comprise a step of normalising the level, concentration or amount of the selected polypeptide between two or more samples. The normalisation may be conducted with reference to BNP, CD9 and/or TIMP-1 polypeptide.

We describe a method for detecting a change in pre-eclampsia state of a cell, tissue, organ or organism, the method comprising detecting a change in a CTB microparticle polypeptide to Annexin V microparticle polypeptide ratio of a pre-eclampsia biomarker polypeptide in or of the cell, tissue, organ or organism (or a profile comprising such a ratio), in which such a change indicates a change in pre-eclampsia state of the cell, tissue, organ or organism.

We describe a method for establishing that a cell, tissue, organ or organism is in a pre-eclampsia state, the method comprising comparing a CTB microparticle polypeptide to Annexin V microparticle polypeptide ratio of a pre-eclampsia biomarker polypeptide in or of the cell, tissue, organ or organism (or a profile comprising such a ratio) with a CTB microparticle polypeptide to Annexin V microparticle polypeptide ratio (or a profile comprising such a ratio) of a cell, tissue, organ or organism known to be in a pre-eclampsia state.

We describe a method of detecting pre-eclampsia in a cell, tissue, organ or organism, the method comprising obtaining a sample from or of that cell, tissue, organ or organism, performing a method as described above on the sample, and comparing the CTB microparticle polypeptide to Annexin V microparticle polypeptide ratio of a pre-eclampsia biomarker polypeptide thereby obtained with a CTB microparticle polypeptide to Annexin V microparticle polypeptide ratio of the pre-eclampsia biomarker polypeptide from a sample known to be of or from a diseased cell, tissue, organ or organism suffering from pre-eclampsia.

We describe a method of treatment or prevention of pre-eclampsia in a cell, tissue, organ or organism, the method comprising detecting pre-eclampsia in a cell, tissue, organ or organism as described above, and administering a treatment for pre-eclampsia to the cell, tissue, organ or organism.

We describe a method for establishing that a cell, tissue, organ or organism is in a pre-eclampsia state, the method comprising comparing a level of expression, activity or amount of a pre-eclampsia biomarker polypeptide in or of the cell, tissue, organ or organism established by a method according to any preceding claim to that of a cell, tissue, organ or organism known to be in that particular state.

We describe a method for detecting a change in a pre-eclampsia state of a cell, tissue, organ or organism, the method comprising detecting modulation of expression, activity or amount of a pre-eclampsia biomarker polypeptide by a method according to any preceding claim, in which such a change indicates a change in state of the cell, tissue, organ or organism.

CTB Binding Microparticle Polypeptide to Annexin V Binding Microparticle Polypeptide Ratio The CTB binding microparticle polypeptide to Annexin V binding microparticle polypeptide ratio may be simply calculated as a ratio of the quantity of polypeptide in CTB binding microparticles to the quantity of polypeptide in Annexin V binding microparticles.

Alternatively, or in addition, the quantity of another polypeptide in CTB binding microparticles to the quantity of that polypeptide in Annexin V binding microparticles known not to be changed as a result of the change in pre-eclampsia state may be used as an internal control.

Thus, instead of, or in addition to, monitoring the change in the CTB binding microparticle polypeptide to Annexin V binding microparticle polypeptide ratio, the ratio of a first ratio against a second ratio may be used for monitoring purposes. Here, the first ratio is the ratio of CTB binding microparticle polypeptide to Annexin V binding microparticle polypeptide known to be changed as a result of the change in pre-eclampsia state and the second ratio being the ratio CTB binding microparticle polypeptide to Annexin V binding microparticle polypeptide ratio known not to be changed as a result of the change in pre-eclampsia state.

CTB Binding Microparticle Polypeptide to Annexin V Binding Microparticle Polypeptide Ratio Profile Alternatively or in addition to determining the ratio of CTB binding microparticle polypeptide to Annexin V binding microparticle polypeptide, a profile comprising a plurality of CTB binding microparticle polypeptide to Annexin V binding microparticle polypeptide ratios for a plurality of selected polypeptide species, each indicative of the pre-eclampsia state of the individual, etc may also be established. Changes to such a profile may be monitored as a means to monitor the pre-eclampsia state of an individual etc. The profile may be established by any means known in the art, such as by hybridisation to an array comprising a plurality of binding agents capable of binding to and distinguishing between each of the plurality of the selected polypeptide species.

Polypeptides

The polypeptide may be any suitable polypeptide whose presence, amount, mass or number etc may be determined.

Such determination may be conducted by any suitable means as known in the art, depending on the protein or polypeptide. Examples of such determination methods include mass spectrometry, spectrophotometry, UV absorption, etc.

Cholera Toxin B (CTB) may have a GenBank Accession Number ABG56900.1.

Annexin V may have a GenBank Accession Number AAB40047.1 or AAB60648.1.

The pre-eclampsia biomarker polypeptide may be selected from the group consisting of PlGF, FLT1, BNP, ANP, CD9, PAI-1, TGF β, PCT, S100b, TIMP1, CD105 and IL6.

These polypeptides are described in detail elsewhere in this document under the section "Pre-Eclampsia Biomarkers".

Accordingly, we describe a method comprising selecting a polypeptide and establishing a ratio of the mass, number, amount, etc of the selected polypeptide in CTB binding microparticle s compared to the selected polypeptide in Annexin V binding microparticles, in a sample of microparticles. The sample of microparticles may be in or of or from etc a cell, tissue, organ or organism.

Combinations of Polypeptides

As noted above, instead of, or in addition to, detection of a single polypeptide, any combination of two or more polypeptides may be used.

Thus, we describe a method in which a combination of two or more polypeptides is selected and their mass, number, amount, etc detected in a first type of microparticle, as compared to their mass, number, amount, etc detected in a second type of microparticle, in a sample from or of a cell, tissue, organ or organism. The ratio so established is indicative of the state of a cell, tissue, organ or organism.

We also describe a method in which a combination of two or more polypeptides is selected and their mass, number, amount, etc detected in a type of microparticle from an individual, as compared to their mass, number, amount, etc detected in a that type of microparticle, in a sample from an individual known not to be suffering from pre-eclampsia;

Combinations of any two or more of PlGF, FLT1, BNP, ANP, CD9, PAI-1, TGF β, PCT, S100b, TIMP1, CD105 and IL6 may be employed.

We describe for example use of any one or more of, such as a combination of: PlGF and FLT1, PlGF and BNP, PlGF and ANP, PlGF and CD9, PlGF and PAI-1, PlGF and TGFβ, PlGF and PCT, PlGF and S100b, PlGF and TIMP1, PlGF and CD105, PlGF and IL6, FLT1 and BNP, FLT1 and ANP, FLT1 and CD9, FLT1 and PAI-1, FLT1 and TGFβ, FLT1 and PCT, FLT1 and S100b, FLT1 and TIMP1, FLT1 and CD105, FLT1 and IL6, BNP and ANP, BNP and CD9, BNP and PAI-1, BNP and TGFβ, BNP and PCT, BNP and S100b, BNP and TIMP1, BNP and CD105, BNP and IL6, ANP and CD9, ANP and PAI-1, ANP and TGFβ, ANP and PCT, ANP and S100b, ANP and TIMP1, ANP and CD105, ANP and IL6, CD9 and PAI-1, CD9 and TGFβ, CD9 and PCT, CD9 and S100b, CD9 and TIMP1, CD9 and CD105, CD9 and IL6, PAI-1 and TGFβ, PAI-1 and PCT, PAI-1 and S100b, PAI-1 and TIMP1, PAI-1 and CD105, PAI-1 and IL6, TGFβ and PCT, TGFβ and S100b, TGFβ and TIMP1, TGFβ and CD105, TGFβ and IL6, PCT and S100b, PCT and TIMP1, PCT and CD105, PCT and IL6, S100b and TIMP1, S100b and CD105, S100b and IL6, TIMP1 and CD105, TIMP1 and IL6 and CD105 and IL6 in the detection of a state comprising for example pre-eclampsia.

Combinations of any three or more of PlGF, FLT1, BNP, ANP, CD9, PAI-1, TGF β, PCT, S100b, TIMP1, CD105 and IL6 may also be employed.

We describe for example use of any one or more of, such as a combination of: PlGF, FLT1 and BNP; PlGF, FLT1 and ANP; PlGF, FLT1 and CD9; PlGF, FLT1 and PAI-1; PlGF, FLT1 and TGFβ; PlGF, FLT1 and PCT; PlGF, FLT1 and S100b; PlGF, FLT1 and TIMP1; PlGF, FLT1 and CD105; PlGF, FLT1 and IL6; PlGF, BNP and ANP; PlGF, BNP and CD9; PlGF, BNP and PAI-1; PlGF, BNP and TGFβ; PlGF, BNP and PCT; PlGF, BNP and S100b; PlGF, BNP and TIMP1; PlGF, BNP and CD105; PlGF, BNP and IL6; PlGF, ANP and CD9; PlGF, ANP and PAI-1; PlGF, ANP and TGFβ; PlGF, ANP and PCT; PlGF, ANP and S100b; PlGF, ANP and TIMP1; PlGF, ANP and CD105; PlGF, ANP and IL6; PlGF, CD9 and PAI-1; PlGF, CD9 and TGFβ; PlGF, CD9 and PCT; PlGF, CD9 and S100b; PlGF, CD9 and TIMP1; PlGF, CD9 and CD105; PlGF, CD9 and IL6; PlGF, PAI-1 and TGFβ; PlGF, PAI-1 and PCT; PlGF, PAI-1 and S100b; PlGF, PAI-1 and TIMP1; PlGF, PAI-1 and CD105; PlGF, PAI-1 and IL6; PlGF, TGFβ and PCT; PlGF, TGFβ and S100b; PlGF, TGFβ and TIMP1; PlGF, TGFβ and CD105; PlGF, TGFβ and IL6; PlGF, PCT and S100b; PlGF, PCT and TIMP1; PlGF, PCT and CD105; PlGF, PCT and IL6; PlGF, S100b and TIMP1; PlGF, S100b and CD105; PlGF, S100b and IL6; PlGF, TIMP1 and CD105; PlGF, TIMP1 and IL6; PlGF, CD105 and IL6; FLT1, BNP and ANP; FLT1, BNP and CD9; FLT1, BNP and PAI-1; FLT1, BNP and TGFβ; FLT1, BNP and PCT; FLT1, BNP and S100b; FLT1, BNP and TIMP1; FLT1, BNP and CD105; FLT1, BNP and IL6; FLT1, ANP and CD9; FLT1, ANP and PAI-1; FLT1, ANP and TGFβ; FLT1, ANP and PCT; FLT1, ANP and S100b; FLT1, ANP and TIMP1; FLT1, ANP and CD105; FLT1, ANP and IL6; FLT1, CD9 and PAI-1; FLT1, CD9 and TGFβ; FLT1, CD9 and PCT; FLT1, CD9 and S100b; FLT1, CD9 and TIMP1; FLT1, CD9 and CD105; FLT1, CD9 and IL6; FLT1, PAI-1 and TGFβ; FLT1, PAI-1 and PCT; FLT1, PAI-1 and S100b; FLT1, PAI-1 and TIMP1; FLT1, PAI-1 and CD105; FLT1, PAI-1 and IL6; FLT1, TGFβ and PCT; FLT1, TGFβ and S100b; FLT1, TGFβ and TIMP1; FLT1, TGFβ and CD105; FLT1, TGFβ and IL6; FLT1, PCT and S100b; FLT1, PCT and TIMP1; FLT1, PCT and CD105; FLT1, PCT and IL6; FLT1, S100b and TIMP1; FLT1, S100b and CD105; FLT1, S100b and IL6; FLT1, TIMP1 and CD105; FLT1, TIMP1 and IL6; FLT1, CD105 and IL6; BNP, ANP and CD9; BNP, ANP and PAI-1; BNP, ANP and TGFβ; BNP, ANP and PCT; BNP, ANP and S100b; BNP, ANP and TIMP1; BNP, ANP and CD105; BNP, ANP and IL6; BNP, CD9 and PAI-1; BNP, CD9 and TGFβ; BNP, CD9 and PCT; BNP, CD9 and S100b; BNP, CD9 and TIMP1; BNP, CD9 and CD105; BNP, CD9 and IL6; BNP, PAI-1 and TGFβ; BNP, PAI-1 and PCT; BNP, PAI-1 and S100b; BNP, PAI-1 and TIMP1; BNP, PAI-1 and CD105; BNP, PAI-1 and IL6; BNP, TGFβ and PCT; BNP, TGFβ and S100b; BNP, TGFβ and TIMP1; BNP, TGFβ and CD105; BNP, TGFβ and IL6; BNP, PCT and S100b; BNP, PCT and TIMP1; BNP, PCT and CD105; BNP, PCT and IL6; BNP, S100b and TIMP1; BNP, S100b and CD105; BNP, S100b and IL6; BNP, TIMP1 and CD105; BNP, TIMP1 and IL6; BNP, CD105 and IL6; ANP, CD9 and PAI-1; ANP, CD9 and TGFβ; ANP, CD9 and PCT; ANP, CD9 and S100b; ANP, CD9 and TIMP1; ANP, CD9 and CD105; ANP, CD9 and IL6; ANP, PAI-1 and TGFβ; ANP, PAI-1 and PCT; ANP, PAI-1 and S100b; ANP, PAI-1 and TIMP1; ANP, PAI-1 and CD105; ANP, PAI-1 and IL6; ANP, TGFβ and PCT; ANP, TGFβ and S100b; ANP, TGFβ and TIMP1; ANP, TGFβ and CD105; ANP, TGFβ and IL6; ANP, PCT and S100b; ANP, PCT and TIMP1; ANP, PCT and CD105; ANP, PCT and IL6; ANP, S100b and TIMP1; ANP, S100b and CD105; ANP, S100b and IL6; ANP, TIMP1 and CD105; ANP, TIMP1 and IL6; ANP, CD105 and IL6; CD9; PAI-1 and TGFβ; CD9, PAI-1 and PCT; CD9, PAI-1 and S100b; CD9, PAI-1 and TIMP1; CD9, PAI-1 and CD105; CD9, PAI-1 and IL6; CD9, TGFβ and PCT; CD9, TGFβ and S100b; CD9, TGFβ and TIMP1; CD9, TGFβ and CD105; CD9, TGFβ and IL6; CD9, PCT and S100b; CD9, PCT and TIMP1; CD9, PCT and CD105; CD9, PCT and IL6; CD9, S100b and TIMP1; CD9, S100b and CD105; CD9, S100b and IL6; CD9, TIMP1 and CD105; CD9, TIMP1 and IL6; CD9, CD105 and IL6; PAI-1, TGFβ and PCT; PAI-1, TGFβ and S100b; PAI-1, TGFβ and TIMP1; PAI-1, TGFβ and CD105; PAI-1, TGFβ and IL6; PAI-1, PCT and S100b; PAI-1, PCT and TIMP1; PAI-1, PCT and CD105; PAI-1, PCT and IL6; PAI-1, S100b and TIMP1; PAI-1, S100b and CD105; PAI-1, S100b and IL6; TIMP1 and CD105; PAI-1, TIMP1 and IL6; PAI-1, CD105 and IL6; TGFβ, PCT and S100b; TGFβ, PCT and TIMP1; TGFβ, PCT and CD105; TGFβ, PCT and IL6; TGFβ, S100b and TIMP1; S100b and CD105; TGFβ, S100b and IL6; TGFβ, TIMP1 and CD105; TGFβ, TIMP1 and IL6; TGFβ, CD105 and IL6; PCT, S100b and TIMP1; PCT, S100b and CD105; PCT, S100b and IL6; PCT, TIMP1 and CD105; PCT, TIMP1 and IL6; PCT, CD105 and IL6; S100b, TIMP1 and CD105; S100b, TIMP1 and IL6; S100b, CD105 and IL6; TIMP1, CD105 and IL6.

Combinations of any four or more of PlGF, FLT1, BNP, ANP, CD9, PAI-1, TGF β, PCT, S100b, TIMP1, CD105 and IL6 may also be employed.

We describe for example use of any one or more of, such as a combination of: PlGF, FLT1, BNP, ANP; PlGF, FLT1, BNP, CD9; PlGF, FLT1, BNP, PAI-1; PlGF, FLT1, BNP, TGFβ; PlGF, FLT1, BNP, PCT; PlGF, FLT1, BNP, S100b; PlGF, FLT1, BNP, TIMP1; PlGF, FLT1, BNP, CD105; PlGF, FLT1, BNP, IL6; PlGF, FLT1, ANP, CD9; PlGF, FLT1, ANP, PAI-1; PlGF, FLT1, ANP, TGFβ; PlGF, FLT1, ANP, PCT; PlGF, FLT1, ANP, S100b; PlGF, FLT1, ANP, TIMP1; PlGF, FLT1, ANP, CD105; PlGF, FLT1, ANP, IL6; PlGF, FLT1, CD9, PAI-1; PlGF, FLT1, CD9, TGFβ; PlGF, FLT1, CD9, PCT; PlGF, FLT1, CD9, S100b; PlGF, FLT1, CD9, TIMP1; PlGF, FLT1, CD9, CD105; PlGF, FLT1, CD9, IL6; PlGF, FLT1, PAI-1, TGFβ; PlGF, FLT1, PAI-1, PCT; PlGF, FLT1, PAI-1, S100b; PlGF, FLT1, PAI-1, TIMP1; PlGF, FLT1, PAI-1, CD105; PlGF, FLT1, PAI-1, IL6; PlGF, FLT1, TGFβ, PCT; PlGF, FLT1, TGFβ, S100b; PlGF, FLT1, TGFβ, TIMP1; PlGF, FLT1, TGFβ, CD105; PlGF, FLT1, TGFβ, IL6; PlGF, FLT1, PCT, S100b; PlGF, FLT1, PCT, TIMP1; PlGF, FLT1, PCT, CD105; PlGF, FLT1, PCT, IL6; PlGF, FLT1, S100b, TIMP1; PlGF, FLT1, S100b, CD105; PlGF, FLT1, S100b, IL6; PlGF, FLT1, TIMP1, CD105; PlGF, FLT1, TIMP1, IL6; PlGF, FLT1, CD105, IL6; PlGF, BNP, ANP, CD9; PlGF, BNP, ANP, PAI-1; PlGF, BNP, ANP, TGFβ; PlGF, BNP, ANP, PCT; PlGF, BNP, ANP, S100b; PlGF, BNP, ANP, TIMP1; PlGF, BNP, ANP, CD105; PlGF, BNP, ANP, IL6; PlGF, BNP, CD9, PAI-1; PlGF, BNP, CD9, TGFβ; PlGF, BNP, CD9, PCT; PlGF, BNP, CD9, S100b; PlGF, BNP, CD9, TIMP1; PlGF, BNP, CD9, CD105; PlGF, BNP, CD9, IL6; PlGF, BNP, PAI-1, TGFβ; PlGF, BNP, PAI-1, PCT; PlGF, BNP, PAI-1, S100b; PlGF, BNP, PAI-1, TIMP1; PlGF, BNP, PAI-1, CD105; PlGF, BNP, PAI-1, IL6; PlGF, BNP, TGFβ, PCT; PlGF, BNP, TGFβ, S100b; PlGF, BNP, TGFβ, TIMP1; PlGF, BNP, TGFβ, CD105; PlGF, BNP, TGFβ, IL6; PlGF, BNP, PCT, S100b; PlGF, BNP, PCT, TIMP1; PlGF, BNP, PCT, CD105; PlGF, BNP, PCT, IL6; PlGF, BNP, S100b, TIMP1; PlGF, BNP, S100b, CD105; PlGF, BNP, S100b, IL6; PlGF, BNP, TIMP1, CD105; PlGF, BNP, TIMP1, IL6; PlGF, BNP, CD105, IL6; PlGF, ANP, CD9, PAI-1; PlGF, ANP, CD9, TGFβ; PlGF, ANP, CD9, PCT; PlGF, ANP, CD9, S100b; PlGF, ANP, CD9, TIMP1; PlGF, ANP, CD9, CD105; PlGF, ANP, CD9, IL6; PlGF, ANP, PAI-1, TGFβ; PlGF, ANP, PAI-1, PCT; PlGF, ANP, PAI-1, S100b; PlGF, ANP, PAI-1, TIMP1; PlGF, ANP, PAI-1, CD105; PlGF, ANP, PAI-1, IL6; PlGF, ANP, TGFβ, PCT; PlGF, ANP, TGFβ, S100b; PlGF, ANP, TGFβ, TIMP1; PlGF, ANP, TGFβ, CD105; PlGF, ANP, TGFβ, IL6; PlGF, ANP, PCT, S100b; PlGF, ANP, PCT, TIMP1; PlGF, ANP, PCT, CD105; PlGF, ANP, PCT, IL6; PlGF, ANP, S100b, TIMP1; PlGF, ANP, S100b, CD105; PlGF, ANP, S100b, IL6; PlGF, ANP, TIMP1, CD105; PlGF, ANP, TIMP1, IL6; PlGF, ANP, CD105, IL6; PlGF, CD9, PAI-1, TGFβ; PlGF, CD9, PAI-1, PCT; PlGF, CD9, PAI-1, S100b; PlGF, CD9, PAI-1, TIMP1; PlGF, CD9, PAI-1, CD105; PlGF, CD9, PAI-1, IL6; PlGF, CD9, TGFβ, PCT; PlGF, CD9, TGFβ, S100b; PlGF, CD9, TGFβ, TIMP1; PlGF, CD9, TGFβ, CD105; PlGF, CD9, TGFβ, IL6; PlGF, CD9, PCT, S100b; PlGF, CD9, PCT, TIMP1; PlGF, CD9, PCT, CD105; PlGF, CD9, PCT, IL6; PlGF, CD9, S100b, TIMP1; PlGF, CD9, S100b, CD105; PlGF, CD9, S100b, IL6; PlGF, CD9, TIMP1, CD105; PlGF, CD9, TIMP1, IL6; PlGF, CD9, CD105, IL6; PlGF, PAI-1, TGFβ, PCT; PlGF, PAI-1, TGFβ, S100b; PlGF, PAI-1, TGFβ, TIMP1; PlGF, PAI-1, TGFβ, CD105; PlGF, PAI-1, TGFβ, IL6; PlGF, PAI-1, PCT, S100b; PlGF, PAI-1, PCT, TIMP1; PlGF, PAI-1, PCT, CD105; PlGF, PAI-1, PCT, IL6; PlGF, PAI-1, S100b, TIMP1; PlGF, PAI-1, S100b, CD105; PlGF, PAI-1, S100b, IL6; PlGF, PAI-1, TIMP1, CD105; PlGF, PAI-1, TIMP1, IL6; PlGF, PAI-1, CD105, IL6; PlGF, TGFβ, PCT, S100b; PlGF, TGFβ, PCT, TIMP1; PlGF, TGFβ, PCT, CD105; PlGF, TGFβ, PCT, IL6; PlGF, TGFβ, S100b, TIMP1; PlGF, TGFβ, S100b, CD105; PlGF, TGFβ, S100b, IL6; PlGF, TGFβ, TIMP1, CD105; PlGF, TGFβ, TIMP1, IL6; PlGF, TGFβ, CD105, IL6; PlGF, PCT, S100b, TIMP1; PlGF, PCT, S100b, CD105; PlGF, PCT, S100b, IL6; PlGF, PCT, TIMP1 CD105; PlGF, PCT, TIMP1, IL6; PlGF, PCT, CD105, IL6; PlGF, S100b, TIMP1, CD105; PlGF, S100b, TIMP1, IL6; PlGF, S100b, CD105, IL6; PlGF, TIMP1 CD105, IL6; FLT1, BNP, ANP, CD9; FLT1, BNP, ANP, PAI-1; FLT1, BNP, ANP, TGFβ; FLT1, BNP, ANP, PCT; FLT1, BNP, ANP, S100b; FLT1, BNP, ANP, TIMP1; FLT1, BNP, ANP, CD105; FLT1, BNP, ANP, IL6; FLT1, BNP, CD9, PAI-1; FLT1, BNP, CD9, TGFβ; FLT1, BNP, CD9, PCT; FLT1, BNP, CD9, S100b; FLT1, BNP, CD9, TIMP1; FLT1, BNP, CD9, CD105; FLT1, BNP, CD9, IL6; FLT1, BNP, PAI-1, TGFβ; FLT1, BNP, PAI-1, PCT; FLT1, BNP, PAI-1, S100b; FLT1, BNP, PAI-1, TIMP1; FLT1, BNP, PAI-1, CD105; FLT1, BNP, PAI-1, IL6; FLT1, BNP, TGFβ, PCT; FLT1, BNP, TGFβ, S100b; FLT1, BNP, TGFβ, TIMP1; FLT1, BNP, TGFβ, CD105; FLT1, BNP, TGFβ, IL6; FLT1, BNP, PCT, S100b; FLT1, BNP, PCT, TIMP1; FLT1, BNP, PCT, CD105; FLT1, BNP, PCT, IL6; FLT1, BNP, S100b, TIMP1; FLT1, BNP, S100b, CD105; FLT1, BNP, S100b, IL6; FLT1, BNP, TIMP1, CD105; FLT1, BNP, TIMP1, IL6; FLT1, BNP, CD105, IL6; FLT1, ANP, CD9, PAI-1; FLT1, ANP, CD9, TGFβ; FLT1, ANP, CD9, PCT; FLT1, ANP, CD9, S100b; FLT1, ANP, CD9, TIMP1; FLT1, ANP, CD9, CD105; FLT1, ANP, CD9, IL6; FLT1, ANP, PAI-1, TGFβ; FLT1, ANP, PAI-1, PCT; FLT1, ANP, PAI-1, S100b; FLT1, ANP, PAI-1, TIMP1; FLT1, ANP, PAI-1, CD105; FLT1, ANP, PAI-1, IL6; FLT1, ANP, TGFβ, PCT; FLT1, ANP, TGFβ, S100b; FLT1, ANP, TGFβ, TIMP1; FLT1, ANP, TGFβ, CD105; FLT1, ANP, TGFβ, IL6; FLT1, ANP, PCT, S100b; FLT1, ANP, PCT, TIMP1; FLT1, ANP, PCT, CD105; FLT1, ANP, PCT, IL6; FLT1, ANP, S100b, TIMP1; FLT1, ANP, S100b, CD105; FLT1, ANP, S100b, IL6; FLT1, ANP, TIMP1, CD105; FLT1, ANP, TIMP1, IL6; FLT1, ANP, CD105, IL6; FLT1, CD9, PAI-1, TGFβ; FLT1, CD9, PAI-1, PCT; FLT1, CD9, PAI-1, S100b; FLT1, CD9, PAI-1, TIMP1; FLT1, CD9, PAI-1, CD105; FLT1, CD9, PAI-1, IL6; FLT1, CD9, TGFβ, PCT; FLT1, CD9, TGFβ, S100b; FLT1, CD9, TGFβ, TIMP1; FLT1, CD9, TGFβ, CD105; FLT1, CD9, TGFβ, IL6; FLT1, CD9, PCT, S100b; FLT1, CD9, PCT, TIMP1; FLT1, CD9, PCT, CD105; FLT1, CD9, PCT, IL6; FLT1, CD9, S100b, TIMP1; FLT1, CD9, S100b, CD105; FLT1, CD9, S100b, IL6; FLT1, CD9, TIMP1, CD105; FLT1, CD9, TIMP1, IL6; FLT1, CD9, CD105, IL6; FLT1, PAI-1, TGFβ, PCT; FLT1, PAI-1, TGFβ, S100b; FLT1, PAI-1, TGFβ, TIMP1; FLT1, PAI-1, TGFβ, CD105; FLT1, PAI-1, TGFβ, IL6; FLT1, PAI-1, PCT, S100b; FLT1, PAI-1, PCT, TIMP1; FLT1, PAI-1, PCT, CD105; FLT1, PAI-1, PCT, IL6; FLT1, PAI-1, S100b, TIMP1; FLT1, PAI-1, S100b, CD105; FLT1, PAI-1, S100b, IL6; FLT1, PAI-1, TIMP1, CD105; FLT1, PAI-1, TIMP1, IL6; FLT1, PAI-1, CD105, IL6; FLT1, TGFβ, PCT, S100b; FLT1, TGFβ, PCT, TIMP1; FLT1, TGFβ, PCT, CD105; FLT1, TGFβ, PCT, IL6; FLT1, TGFβ, S100b, TIMP1; FLT1, TGFβ, S100b, CD105; FLT1, TGFβ, S100b, IL6; FLT1, TGFβ, TIMP1, CD105; FLT1, TGFβ, TIMP1, IL6; FLT1, TGFβ, CD105, IL6; FLT1, PCT, S100b, TIMP1; FLT1, PCT, S100b, CD105; FLT1, PCT, S100b, IL6; FLT1, PCT, TIMP1, CD105; FLT1, PCT, TIMP1, IL6; FLT1, PCT, CD105, IL6; FLT1, S100b, TIMP1, CD105; FLT1, S100b, TIMP1, IL6; FLT1, S100b, CD105, IL6; FLT1, TIMP1, CD105, IL6; BNP, ANP, CD9, PAI-1; BNP, ANP, CD9, TGFβ; BNP, ANP, CD9, PCT; BNP, ANP, CD9, S100b; BNP, ANP, CD9, TIMP1; BNP, ANP, CD9, CD105; BNP, ANP, CD9, IL6; BNP, ANP, PAI-1, TGFβ; BNP, ANP, PAI-1, PCT; BNP, ANP, PAI-1, S100b; BNP, ANP, PAI-1, TIMP1; BNP, ANP, PAI-1, CD105; BNP, ANP, PAI-1, IL6; BNP, ANP, TGFβ, PCT; BNP, ANP, TGFβ, S100b; BNP, ANP, TGFβ, TIMP1; BNP, ANP, TGFβ, CD105; BNP, ANP, TGFβ, IL6; BNP, ANP, PCT, S100b; BNP, ANP, PCT, TIMP1; BNP, ANP, PCT, CD105; BNP, ANP, PCT, IL6; BNP, ANP, S100b, TIMP1; BNP, ANP, S100b, CD105; BNP, ANP, S100b, IL6; BNP, ANP, TIMP1, CD105; BNP, ANP, TIMP1, IL6; BNP, ANP, CD105, IL6; BNP, CD9, PAI-1, TGFβ; BNP, CD9, PAI-1, PCT; BNP, CD9, PAI-1, S100b; BNP, CD9, PAI-1, TIMP1; BNP, CD9, PAI-1, CD105; BNP, CD9, PAI-1, IL6; BNP, CD9, TGFβ, PCT; BNP, CD9, TGFβ, S100b; BNP, CD9, TGFβ, TIMP1; BNP, CD9, TGFβ, CD105; BNP, CD9, TGFβ, IL6; BNP, CD9, PCT, S100b; BNP, CD9, PCT, TIMP1; BNP, CD9, PCT, CD105; BNP, CD9, PCT, IL6; BNP, CD9, S100b, TIMP1; BNP, CD9, S100b, CD105; BNP, CD9, S100b, IL6; BNP, CD9, TIMP1, CD105; BNP, CD9, TIMP1, IL6; BNP, CD9, CD105, IL6; BNP, PAI-1, TGFβ, PCT; BNP, PAI-1, TGFβ, S100b; BNP, PAI-1, TGFβ, TIMP1; BNP, PAI-1, TGFβ, CD105; BNP, PAI-1, TGFβ, IL6; BNP, PAI-1, PCT, S100b; BNP, PAI-1, PCT, TIMP1; BNP, PAI-1, PCT, CD105; BNP, PAI-1, PCT, IL6; BNP, PAI-1, S100b, TIMP1; BNP, PAI-1, S100b, CD105; BNP, PAI-1, S100b, IL6; BNP, PAI-1, TIMP1, CD105; BNP, PAI-1, TIMP1, IL6; BNP, PAI-1, CD105, IL6; BNP, TGFβ, PCT, S100b; BNP, TGFβ, PCT, TIMP1; BNP, TGFβ, PCT, CD105; BNP, TGFβ, PCT, IL6; BNP, TGFβ, S100b, TIMP1; BNP, TGFβ, S100b, CD105; BNP, TGFβ, S100b, IL6; BNP, TGFβ, TIMP1, CD105; BNP, TGFβ, TIMP1, IL6; BNP, TGFβ, CD105, IL6; BNP, PCT, S100b, TIMP1; BNP, PCT, S100b, CD105; BNP, PCT, S100b, IL6; BNP, PCT, TIMP1, CD105; BNP, PCT, TIMP1, IL6; BNP, PCT, CD105, IL6; BNP, S100b, TIMP1, CD105; BNP, S100b, TIMP1, IL6; BNP, S100b, CD105, IL6; BNP, TIMP1, CD105, IL6; ANP, CD9, PAI-1, TGFβ; ANP, CD9, PAI-1, PCT; ANP, CD9, PAI-1, S100b; ANP, CD9, PAI-1, TIMP1; ANP, CD9, PAI-1, CD105; ANP, CD9, PAI-1, IL6; ANP, CD9, TGFβ, PCT; ANP, CD9, TGFβ, S100b; ANP, CD9, TGFβ, TIMP1; ANP, CD9, TGFβ, CD105; ANP, CD9, TGFβ, IL6; ANP, CD9, PCT, S100b; ANP, CD9, PCT, TIMP1; ANP, CD9, PCT, CD105; ANP, CD9, PCT, IL6; ANP, CD9, S100b, TIMP1; ANP, CD9, S100b, CD105; ANP, CD9, S100b, IL6; ANP, CD9, TIMP1, CD105; ANP, CD9, TIMP1, IL6; ANP, CD9, CD105, IL6; ANP, PAI-1, TGFβ, PCT; ANP, PAI-1, TGFβ, S100b; ANP, PAI-1, TGFβ, TIMP1; ANP, PAI-1, TGFβ, CD105; ANP, PAI-1, TGFβ, IL6; ANP, PAI-1, PCT, S100b; ANP, PAI-1, PCT, TIMP1; ANP, PAI-1, PCT, CD105; ANP, PAI-1, PCT, IL6; ANP, PAI-1, S100b, TIMP1; ANP, PAI-1, S100b, CD105; ANP, PAI-1, S100b, IL6; ANP, PAI-1, TIMP1, CD105; ANP, PAI-1, TIMP1, IL6; ANP, PAI-1, CD105, IL6; ANP, TGFβ, PCT, S100b; ANP, TGFβ, PCT, TIMP1; ANP, TGFβ, PCT, CD105; ANP, TGFβ, PCT, IL6; ANP, TGFβ, S100b, TIMP1; ANP, TGFβ, S100b, CD105; ANP, TGFβ, S100b, IL6; ANP, TGFβ, TIMP1, CD105; ANP, TGFβ, TIMP1, IL6; ANP, TGFβ, CD105, IL6; ANP, PCT, S100b, TIMP1; ANP, PCT, S100b, CD105; ANP, PCT, S100b, IL6; ANP, PCT, TIMP1, CD105; ANP, PCT, TIMP1, IL6; ANP, PCT, CD105, IL6; ANP, S100b, TIMP1, CD105; ANP, S100b, TIMP1, IL6; ANP, S100b, CD105, IL6; ANP, TIMP1, CD105, IL6; CD9, PAI-1, TGFβ, PCT; CD9, PAI-1, TGFβ, S100b; CD9, PAI-1, TGFβ, TIMP1; CD9, PAI-1, TGFβ, CD105; CD9, PAI-1, TGFβ, IL6; CD9, PAI-1, PCT, S100b; CD9, PAI-1, PCT, TIMP1; CD9, PAI-1, PCT, CD105; CD9, PAI-1, PCT, IL6; CD9, PAI-1, S100b, TIMP1; CD9, PAI-1, S100b, CD105; CD9, PAI-1, S100b, IL6; CD9, PAI-1, TIMP1, CD105; CD9, PAI-1, TIMP1, IL6; CD9, PAI-1, CD105, IL6; CD9, TGFβ, PCT, S100b; CD9, TGFβ, PCT, TIMP1; CD9, TGFβ, PCT, CD105; CD9, TGFβ, PCT, IL6; CD9, TGFβ, S100b, TIMP1; CD9, TGFβ, S100b, CD105; CD9, TGFβ, S100b, IL6; CD9, TGFβ, TIMP1, CD105; CD9, TGFβ, TIMP1, IL6; CD9, TGFβ, CD105, IL6; CD9, PCT, S100b, TIMP1; CD9, PCT, S100b, CD105; CD9, PCT, S100b, IL6; CD9, PCT, TIMP1, CD105; CD9, PCT, TIMP1, IL6; CD9, PCT, CD105, IL6; CD9, S100b, TIMP1, CD105; CD9, S100b, TIMP1, IL6; CD9, S100b, CD105, IL6; CD9, TIMP1, CD105, IL6; PAI-1, TGFβ, PCT, S100b; PAI-1, TGFβ, PCT, TIMP1; PAI-1, TGFβ, PCT, CD105; PAI-1, TGFβ, PCT, IL6; PAI-1, TGFβ, S100b, TIMP1; PAI-1, TGFβ, S100b, CD105; PAI-1, TGFβ, S100b, IL6; PAI-1, TGFβ, TIMP1, CD105; PAI-1, TGFβ, TIMP1, IL6; PAI-1, TGFβ, CD105, IL6; PAI-1, PCT, S100b, TIMP1; PAI-1, PCT, S100b, CD105; PAI-1, PCT, S100b, IL6; PAI-1, PCT, TIMP1, CD105; PAI-1, PCT, TIMP1, IL6; PAI-1, PCT, CD105, IL6; PAI-1, S100b, TIMP1, CD105; PAI-1, S100b, TIMP1, IL6; PAI-1, S100b, CD105, IL6; PAI-1, TIMP1, CD105, IL6; TGFβ, PCT, S100b, TIMP1; TGFβ, PCT, S100b, CD105; TGFβ, PCT, S100b, IL6; TGFβ, PCT, TIMP1, CD105; TGFβ, PCT, TIMP1, IL6; TGFβ, PCT, CD105, IL6; TGFβ, S100b, TIMP1, CD105; TGFβ, S100b, TIMP1, IL6; TGFβ, S100b, CD105, IL6; TGFβ, TIMP1, CD105, IL6; PCT, S100b, TIMP1, CD105; PCT, S100b, TIMP1, IL6; PCT, S100b, CD105, IL6; PCT, TIMP1, CD105, IL6; S100b, TIMP1, CD105, IL6.

Polypeptide Profiles

The method may comprise establishing a profile comprising a plurality of CTB binding microparticle polypeptide to Annexin V binding microparticle polypeptide ratios for a plurality of selected polypeptide species. Each of the profiles may be indicative of the state of the cell, tissue, organ or organism. In other words, more than one polypeptide species may be used (i.e., ratios obtained for more than one polypeptide species).

The same meanings of "higher" and "lower" as described above apply where amounts of combinations of polypeptides are determined.

Normalisation

The method may further comprise a step of normalisation. Such a step may comprise determining or ensuring that the quantity or concentration of any one or more proteins or polypeptides is the same across different samples.

Normalisation of levels may be performed in a conventional manner as known in the art, such as by converting the measured amounts or levels into protein mass of CTB- or AV-associated marker per ml plasma.

A normalisation step, as applied to the methods and compositions described here, may make use of a polypeptide whose concentration is known to be the same across any two samples.

Accordingly, the methods described here may comprise a normalisation step. The normalisation step may comprise adjusting the level, concentration or amount of a particular polypeptide in one or more samples. The normalisation step may be conducted on two or more samples in which the level, concentration or amount of a particular polypeptide (prior to normalisation) are substantially different from each other. The normalisation step may be such that, following normalisation, the level, concentration or amount of a particular polypeptide in two or more samples are substantially the same.

The normalisation step may comprise diluting or concentrating one or other of the two samples, to increase or decrease the level, concentration or amount of a particular polypeptide in one or both samples.

Alternatively, or in addition, the normalisation step may comprise determining, for a selected two or more samples, the ratio of the levels concentration or amount of a particular polypeptide between the samples. This may be achieved by reference to a reference polypeptide which is known to have the same level, concentration or amount in each of a group of samples of interest. The reference polypeptide may comprise one or more of ACE2 and CRP.

It will be appreciated that, where the method comprises determination of ratios, a normalisation step may not be needed.

Detection and Diagnostic Methods

Detection of Expression of Pre-Eclampsia Biomarker Polypeptide

It will be appreciated that as the level of pre-eclampsia biomarker polypeptide may with the progression of pre-eclampsia, that detection of pre-eclampsia biomarker polypeptide expression, amount or activity may also be used to predict the severity or progression of pre-eclampsia in an individual.

That is to say, an elevated level of ANP, CD105, IL6, TIMP1, PlGF, FLT1, BNP, PAI-1, TGF β, PCT or S100b in a CTB binding microparticle, an elevated level of a PlGF, FLT1, BNP, PAI-1, TGF β, PCT or S100b protein in an Annexin V binding microparticle, an elevated level of CD9 in an Annexin V binding microparticle or a lowered level of CD9 in a CTB binding microparticle may indicate severe pre-eclampsia compared to individuals or cognate populations with normal levels of pre-eclampsia biomarker polypeptide.

Detection of expression, amount or activity of pre-eclampsia biomarker polypeptide may therefore be used as a method of prognosis of an individual with pre-eclampsia.

Detection of pre-eclampsia biomarker polypeptide expression, amount or level may be used to determine the likelihood of success of a particular therapy in an individual with a pre-eclampsia.

The diagnostic methods described in this document may be combined with the therapeutic methods described. Thus, we provide for a method of treatment, prophylaxis or alleviation of pre-eclampsia in an individual, the method comprising detecting modulation of expression, amount or activity of pre-eclampsia biomarker polypeptide in a cell (such as a CTB binding microparticle or an Annexin V binding microparticle, or both) of the individual and administering an appropriate therapy to the individual based on the severity of the pre-eclampsia.

The presence and quantity of pre-eclampsia biomarker polypeptide polypeptides and nucleic acids may be detected in a sample as described in further detail below. Thus, the pre-eclampsia biomarker polypeptide associated diseases, including pre-eclampsia, can be diagnosed by methods comprising determining from a sample derived from a subject an abnormally decreased or increased expression, amount or activity, such as a increased expression, amount or activity, of the pre-eclampsia biomarker polypeptide polypeptide or pre-eclampsia biomarker polypeptide mRNA.

The sample may comprise a cell or tissue sample from an organism or individual suffering or suspected to be suffering from a disease associated with increased, reduced or otherwise abnormal pre-eclampsia biomarker polypeptide expression, amount or activity, including spatial or temporal changes in level or pattern of expression, amount or activity. The level or pattern of expression, amount or activity of pre-eclampsia biomarker polypeptide in an organism suffering from or suspected to be suffering from such a disease may be usefully compared with the level or pattern of expression, amount or activity in a normal organism as a means of diagnosis of disease.

The sample may comprise a cell or tissue sample from an individual suffering or suspected to be suffering from pre-eclampsia.

In some embodiments, an increased level of expression, amount or activity of pre-eclampsia biomarker polypeptide is detected in the sample. The level of pre-eclampsia biomarker polypeptide may be increased to a significant extent when compared to normal cells, or cells known not to be pre-eclampsia ous. Such cells may be obtained from the individual being tested, or another individual, such as those matched to the tested individual by age, weight, lifestyle, etc.

In some embodiments, the level of expression, amount or activity of pre-eclampsia biomarker polypeptide is increased by 10%, 20%, 30% or 40% or more. In some embodiments, the level of expression, amount or activity of pre-eclampsia biomarker polypeptide is increased by 45% or more, such as 50% or more.

The expression, amount or activity of pre-eclampsia biomarker polypeptide may be detected in a number of ways, as known in the art, and as described in further detail below.

Typically, the amount of pre-eclampsia biomarker polypeptide in a sample of tissue from an individual is measured, and compared with a sample from an unaffected individual. Both pre-eclampsia biomarker polypeptide nucleic acid, as well as pre-eclampsia biomarker polypeptide polypeptide levels may be measured.

Detection of the amount, activity or expression of pre-eclampsia biomarker polypeptide may be used to grade pre-eclampsia.

Levels of pre-eclampsia biomarker polypeptide gene expression may be determined using a number of different techniques.

Measuring Expression of Pre-Eclampsia Biomarker Polypeptide at the Polypeptide Level Pre-eclampsia biomarker polypeptide expression can be detected at the polypeptide level.

In a further embodiment, therefore, pre-eclampsia biomarker polypeptide expression, amount or activity may be detected by detecting the presence or amount of pre-eclampsia biomarker polypeptide in a sample. This may be achieved by using molecules which bind to pre-eclampsia biomarker polypeptides. Suitable molecules/agents which bind either directly or indirectly to pre-eclampsia biomarker polypeptides in order to detect their presence include naturally occurring molecules such as peptides and proteins, for example antibodies, or they may be synthetic molecules.

Thus, we disclose a method of detecting the presence of a pre-eclampsia biomarker polypeptide by contacting a cell sample with an antibody capable of binding the polypeptide and monitoring said sample for the presence of the polypeptide.

For example, the pre-eclampsia biomarker polypeptide may be detected using an anti-pre-eclampsia biomarker polypeptide antibody. Such antibodies may be made by means known in the art (as described elsewhere in this document).

This may conveniently be achieved by monitoring the presence of a complex formed between the antibody and the polypeptide, or monitoring the binding between the polypeptide and the antibody. Methods of detecting binding between two entities are known in the art, and include FRET (fluorescence resonance energy transfer), surface plasmon resonance, etc.

Standard laboratory techniques such as immunoblotting as described above can be used to detect altered levels of pre-eclampsia biomarker protein, as compared with untreated cells in the same cell population.

Gene expression may also be determined by detecting changes in post-translational processing of pre-eclampsia biomarker polypeptides or post-transcriptional modification of pre-eclampsia biomarker nucleic acids. For example, differential phosphorylation of pre-eclampsia biomarker polypeptide polypeptides, the cleavage of pre-eclampsia biomarker polypeptides or alternative splicing of pre-eclampsia biomarker polypeptide RNA, and the like may be measured. Levels of expression of gene products such as pre-eclampsia biomarker polypeptides, as well as their post-translational modification, may be detected using proprietary protein assays or techniques such as 2D polyacrylamide gel electrophoresis.

Assay techniques that can be used to determine levels of pre-eclampsia biomarker protein in a sample derived from a host are well-known to those of skill in the art. Antibodies can be assayed for immunospecific binding by any method known in the art.

The immunoassays which can be used include but are not limited to competitive and non-competitive assay systems using techniques such as western blots, radioimmunoassays, ELISA, sandwich immunoassays, immunoprecipitation assays, precipitin reactions, gel diffusion precipitin reactions, immunodiffusion assays, agglutination assays, complement-fixation assays, immunoradiometric assays, fluorescent immunoassays and protein A immunoassays. Such assays are routine in the art (see, for example, Ausubel et al., eds, 1994, *Current Protocols in Molecular Biology*, Vol. 1, John Wiley & Sons, Inc., New York, which is incorporated by reference herein in its entirety).

The specimen may be assayed for polypeptides/proteins by immunohistochemical and immunocytochemical staining (see generally Stites and Ten, Basic and Clinical Immunology, Appleton and Lange, 1994), ELISA, RIA, immunoblots, Western blotting, immunoprecipitation, functional assays and protein truncation test. Other assay methods include radioimmunoassays, competitive-binding assays, Western Blot analysis and ELISA assays.

ELISA assays are well known to those skilled in the art. Both polyclonal and monoclonal antibodies may be used in the assays. Where appropriate other immunoassays, such as radioimmunoassays (RIA) may be used as are known to those in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521 as well as Sambrook et al, 1992.

Diagnostic Kits

We also provide diagnostic kits for detecting pre-eclampsia in an individual, or susceptibility to pre-eclampsia in an individual.

The diagnostic kit may comprise means for detecting expression, amount or activity of pre-eclampsia biomarker in the individual, by any means as described in this document. The diagnostic kit may therefore comprise any one or more of the following: a pre-eclampsia biomarker polynucleotide or a fragment thereof; a complementary nucleotide sequence to pre-eclampsia biomarker nucleic acid or a fragment thereof; a pre-eclampsia biomarker polypeptide or a fragment thereof, or an antibody to a pre-eclampsia biomarker, such as comprising an anti-pre-eclampsia biomarker antibody or an anti-peptide antibody human pre-eclampsia biomarker antibody.

The diagnostic kit may comprise instructions for use, or other indicia. The diagnostic kit may further comprise means for treatment or prophylaxis of pre-eclampsia, such as any of the compositions described in this document, or any means known in the art for treating pre-eclampsia. In particular, the diagnostic kit may comprise an anti-pre-eclampsia biomarker agent as described, for example obtained by screening. The diagnostic kit may comprise a therapeutic drug. The therapeutic drug may also comprise an anti-pre-eclampsia biomarker antibody. The therapeutic drug may comprise an antihypertensive, isradipine, Labetolol, Hydralazine, Nifedipine or magnesium sulphate.

Isradipine

Isradipine (tradenames DynaCirc, Prescal) is a calcium channel blocker of the dihydropyridine class. It is usually prescribed for the treatment of high blood pressure in order to reduce the risk of stroke and heart attack.

The IUPAC name of Isradipine is 3-methyl 5-propan-2-yl 4-(2,1,3-benzoxadiazol-4-yl)-2,6-dimethyl-1,4-dihydropyridine-3,5-dicarboxylate Labetolol Labetalol (Normodyne, Trandate) is a mixed alpha/beta adrenergic antagonist, which is used to treat high blood pressure.

The IUPAC name of Labetolol is (RS)-2-hydroxy-5-{1-hydroxy-2-[(1-methyl-3-phenylpropyl)amino]ethyl}benzamide Hydralazine Hydralazine (apresoline) is a direct-acting smooth muscle relaxant used to treat hypertension by acting as a vasodilator primarily in arteries and arterioles. By relaxing vascular smooth muscle, vasodilators act to decrease peripheral resistance, thereby lowering blood pressure and decreasing afterload.

It belongs to the hydrazinophthalazine class of drugs.

The IUPAC name for Hydralazine is 1-hydrazinylphthalazine

Nifedipine

Nifedipine (brand names Adalat CC and Procardia, according to FDA Orange Book) is a dihydropyridine calcium channel blocker that primarily blocks L-type calcium channels. Its main uses are as an antianginal (especially in Prinzmetal's angina) and antihypertensive, although a large number of other indications have recently been found for this agent, such as Raynaud's phenomenon, premature labor, and painful spasms of the esophagus such as in cancer and tetanus patients. It is also commonly used for the small subset of pulmonary hypertension patients whose symptoms respond to calcium channel blockers.

The IUPAC name of Nifedipine is 3,5-dimethyl 2,6-dimethyl-4-(2-nitrophenyl)-1,4-dihydropyridine-3,5-dicarboxylate Prophylactic and Therapeutic Methods We disclose methods of treating an abnormal conditions, such as pre-eclampsia, related to modulated amounts of pre-eclampsia biomarker expression or activity. Methods of preventing pre-eclampsia (i.e., prophylaxis) also suitably employ the same or similar approaches.

In general terms, our methods involve manipulation of pre-eclampsia cells, by modulating (such as down-regulating or up-regulating) the expression, amount or activity of pre-eclampsia biomarker in the cell. A step of detecting modulated pre-eclampsia biomarker expression, amount or activity in a cell may be conducted before or after the manipulation step. The detection step may detect up-regulated or down-regulated pre-eclampsia biomarker expression, amount or activity. Any of the methods of modulating or down-regulating pre-eclampsia biomarker, as described in detail elsewhere in this document, may be used.

Pre-eclampsia is defined as being "treated" if a condition associated with the disease is significantly inhibited (i.e., by 50% or more) relative to controls. The inhibition may be by at least 75% relative to controls, such as by 90%, by 95% or 100% relative to controls. The condition may comprise any of the known symptoms for pre-eclampsia. By the term "treatment" we mean to also include prophylaxis or alleviation of pre-eclampsia.

One possible approach for therapy of such disorders is to express anti-sense constructs directed against pre-eclampsia biomarker polynucleotides as described here, and administering them to cells, to inhibit gene function.

Anti-sense constructs may be used to inhibit gene function. Antisense constructs, i.e., nucleic acid, such as RNA, constructs complementary to the sense nucleic acid or mRNA, are described in detail in U.S. Pat. No. 6,100,090 (Monia et al.), and Neckers et al., 1992, *Crit Rev Oncog*

3(1-2):175-231, the teachings of which document are specifically incorporated by reference.

In a particular example, pre-eclampsia may be treated or prevented by reducing the amount, expression or activity of pre-eclampsia biomarker in whole or in part, for example by siRNAs capable of binding to and destroying pre-eclampsia biomarker mRNA. We specifically provide for an anti-pre-eclampsia biomarker agent which downregulates pre-eclampsia biomarker by RNA interference. The anti-pre-eclampsia biomarker agent may comprise a Small Interfering RNA (siRNA) or Short Hairpin RNA (shRNA).

RNA interference (RNAi) is a method of post transcriptional gene silencing (PTGS) induced by the direct introduction of double-stranded RNA (dsRNA) and has emerged as a useful tool to knock out expression of specific genes in a variety of organisms. RNAi is described by Fire et al., Nature 391:806-811 (1998). Other methods of PTGS are known and include, for example, introduction of a transgene or virus. Generally, in PTGS, the transcript of the silenced gene is synthesised but does not accumulate because it is rapidly degraded. Methods for PTGS, including RNAi are described, for example, in the Ambion.com world wide web site, in the directory "/hottopics/", in the "rnai"

Suitable methods for RNAi in vitro are described herein. One such method involves the introduction of siRNA (small interfering RNA). Current models indicate that these 21-23 nucleotide dsRNAs can induce PTGS. Methods for designing effective siRNAs are described, for example, in the Ambion web site described above. RNA precursors such as Short Hairpin RNAs (shRNAs) can also be encoded by all or a part of the pre-eclampsia biomarker nucleic acid sequence.

Alternatively, double-stranded (ds) RNA is a powerful way of interfering with gene expression in a range of organisms that has recently been shown to be successful in mammals (Wianny and Zernicka-Goetz, 2000, *Nat Cell Biol* 2:70-75). Double stranded RNA corresponding to the sequence of a pre-eclampsia biomarker polynucleotide can be introduced into or expressed in oocytes and cells of a candidate organism to interfere with pre-eclampsia biomarker activity.

Other methods of modulating pre-eclampsia biomarker gene expression are known to those skilled in the art and include dominant negative approaches. Thus, another approach is to use non-functional variants of pre-eclampsia biomarker polypeptide in this document that compete with the endogenous gene product resulting in inhibition of function.

Pre-eclampsia biomarker expression may also be modulated by as introducing peptides or small molecules which inhibit gene expression or functional activity. Thus, compounds identified by the assays described here as binding to or modulating, such as down-regulating, the amount, activity or expression of pre-eclampsia biomarker polypeptide may be administered to cells to prevent the function of pre-eclampsia biomarker polypeptide. Such a compound may be administered along with a pharmaceutically acceptable carrier in an amount effective to down-regulate expression or activity of pre-eclampsia biomarker, or by activating or down-regulating a second signal which controls pre-eclampsia biomarker expression, activity or amount, and thereby alleviating the abnormal condition.

Suitable antibodies against pre-eclampsia biomarker polypeptide may also be used as therapeutic agents.

Alternatively, gene therapy may be employed to control the endogenous production of pre-eclampsia biomarker by the relevant cells in the subject. For example, a polynucleotide encoding a pre-eclampsia biomarker siRNA or a portion of this may be engineered for expression in a replication defective retroviral vector, as discussed below. The retroviral expression construct may then be isolated and introduced into a packaging cell transduced with a retroviral plasmid vector containing RNA encoding an anti-pre-eclampsia biomarker siRNA such that the packaging cell now produces infectious viral particles containing the sequence of interest. These producer cells may be administered to a subject for engineering cells in vivo and regulating expression of the pre-eclampsia biomarker polypeptide in vivo. For overview of gene therapy, see Chapter 20, Gene Therapy and other Molecular Genetic-based Therapeutic Approaches, (and references cited therein) in Human Molecular Genetics, T Strachan and A P Read, BIOS Scientific Publishers Ltd (1996).

Pre-Eclampsia

Pre-eclampsia or preeclampsia is a medical condition characterized by high blood pressure and significant amounts of protein in the urine of a pregnant woman. If left untreated, it can develop into eclampsia, the life-threatening occurrence of seizures during pregnancy.

There are many different causes for the condition. It appears likely that there are substances from the placenta that can cause endothelial dysfunction in the maternal blood vessels of susceptible women. While blood pressure elevation is the most visible sign of the disease, it involves generalised damage to the maternal endothelium, kidneys, and liver, with the release of vasoconstrictive factors being a consequence of the original damage.

An outdated medical term for pre-eclampsia is toxemia of pregnancy, since it was thought that the condition was caused by toxins.

Pre-eclampsia may develop at any time after 20 weeks of gestation. Pre-eclampsia before 32 weeks is considered early onset, and is associated with increased morbidity. Its progress differs among patients; most cases are diagnosed before labor typically would begin. Pre-eclampsia may also occur up to six weeks after delivery. Apart from Caesarean section and induction of labor (and therefore delivery of the placenta), there is no known cure. It is the most common of the dangerous pregnancy complications; it may affect both the mother and foetus.

Causes

The pre-eclampsia syndrome is thought in many cases to be caused by a shallowly implanted placenta which becomes hypoxic, leading to an immune reaction characterized by secretion of upregulated inflammatory mediators from the placenta, and acting on the vascular endothelium. The shallow implantation is thought to stem from the maternal immune system's response to the placenta and refers to evidence suggesting a lack of established immunological tolerance in pregnancy. This results in an immune response against paternal antigens from the foetus and its placenta. In some cases of pre-eclampsia it is thought that the mother lacks the receptors for the proteins the placenta is using to downregulate the maternal immune system's response to it. This view is also consistent with evidence showing many miscarriages to be an immunological disorder where the mother's immune system "unleashes a destructive attack on the tissues of the developing child".

In many cases of the pre-eclampsia syndrome, however, the maternal response to the placenta appears to have allowed for normal implantation. It is possible that women with higher baseline levels of inflammation stemming from underlying conditions such as chronic hypertension or autoimmune disease may have less tolerance for the inflammatory burden of pregnancy.

If severe, pre-eclampsia progresses to fulminant pre-eclampsia, with headaches, visual disturbances, and epigastric pain, and further to the HELLP syndrome and eclampsia. HELLP syndrome itself is considered subtype of preeclampsia. Placental abruption is associated with hypertensive pregnancies. These are life-threatening conditions for both the developing baby and the mother.

Many theories have attempted to explain why pre-eclampsia arises, and have linked the syndrome to the presence of the following:
  endothelial cell injury
  immune rejection of the placenta
  compromised placental perfusion
  altered vascular reactivity
  imbalance between prostacyclin and thromboxane
  decreased glomerular filtration rate with retention of salt and water
  decreased intravascular volume
  increased central nervous system irritability
  disseminated intravascular coagulation
  uterine muscle stretch (ischemia)
  dietary factors, including vitamin deficiency
  Hughes syndrome
  genetic factors—There is an association between pre-eclampsia and certain variants of the genes coding for angiotensin-converting enzyme, CTLA-4, thrombin, factor V, lipoprotein lipase and plasminogen activator inhibitor-1. These genetic risk factors are generally shared with those of cardiovascular diseases in general.
  air pollution
  obesity
  Thyroid dysfunction: Subclinical hypothyroidism in early pregnancy, compared with normal thyroid function, has been estimated to increase the risk of pre-eclampsia with an odds ratio of 1.7.

The current understanding of the syndrome is as a two-stage process, with a highly variable first stage which predisposes the placenta to hypoxia, followed by the release of soluble factors which result in many of the other events in pathogenesis.

Risk Factors

Known risk factors for preeclampsia include:
  Nulliparity
  Diabetes mellitus
  Renal disease
  Chronic hypertension
  Prior history of preeclampsia
  Age (>35 or <15)
  Obesity
  Antiphospholipid antibody syndrome
  Multiple gestation
  Pathogenesis Although much research into the cause and mechanism of pre-eclampsia has taken place, its exact pathogenesis remains uncertain. Some studies support notions of inadequate blood supply to the placenta making it release particular hormones or chemical agents that, in mothers predisposed to the condition, leads to damage of the endothelium (lining of blood vessels), alterations in metabolism, inflammation, and other possible reactions.

Abnormalities in the maternal immune system and insufficiency of gestational immune tolerance seem to play major roles in pre-eclampsia. One of the main differences found in pre-eclampsia is a shift toward Th1 responses and the production of IFN-γ. The origin of IFN-γ is not clearly identified and could be the natural killer cells of the uterus, the placental dendritic cells modulating responses of T helper cells, alterations in synthesis of or response to regulatory molecules, or changes in the function of regulatory T cells in pregnancy. Aberrant immune responses promoting pre-eclampsia may also be due to an altered foetal allorecognition or to inflammatory triggers. It has been documented that foetal cells such as foetal erythroblasts as well as cell-free foetal DNA are increased in the maternal circulation in women who develop pre-eclampsia. These findings have given rise to the hypothesis that pre-eclampsia is a disease process by which a placental lesion such as hypoxia allows increased foetal material into maternal circulation that leads to an immune response and endothelial damage ultimately resulting in pre-eclampsia and eclampsia.

Some studies suggest that hypoxia resulting from inadequate perfusion upregulates sFlt-1, a VEGF and PlGF antagonist, leading to a damaged maternal endothelium and restriction of placental growth. In addition, endoglin, a TGF-beta antagonist, is elevated in pregnant women who develop pre-eclampsia. Soluble endoglin is likely upregulated by the placenta in response to an upregulation of cell-surface endoglin produced by the maternal immune system, although there is also the potential that sEng is produced by the maternal endothelium. Levels of both sFlt-1 and sEng increase as severity of disease increases, with levels of sEng surpassing levels of sFlt-1 in HELLP syndrome cases. Recent data indicate that Gadd45a stress signaling regulates elevated sFlt-1 expression in pre-eclampsia. Another VEGF antagonist implicated in pathogenesis of preeclampsia is soluble fms-like tyrosine kinase-1.

Both sFlt-1 and sEng are upregulated in all pregnant women to some extent, supporting the idea that hypertensive disease in pregnancy is a normal pregnancy adaptation gone awry. As natural killer cells are intimately involved in placentation and as placentation involves a degree of maternal immune tolerance for a foreign placenta which requires maternal resources for its support, it is not surprising that the maternal immune system might respond more negatively to the arrival of some placentae under certain circumstances, such as a placenta which is more invasive than normal. Initial maternal rejection of the placental cytotrophoblasts may be the cause of the inadequately remodeled spiral arteries in those cases of pre-eclampsia associated with shallow implantation, leading to downstream hypoxia and the appearance of maternal symptoms in response to upregulated sFlt-1 and sEng.

One hypothesis for vulnerability to preeclampsia is the maternal-foetal conflict between the maternal organism and foetus. After the first trimester trophoblasts enter the spiral arteries of the mother to alter the spiral arteries and thereby gain more access to maternal nutrients. However, occasionally there is impaired trophoblast invasion that results in inadequate alterations to the uterine spiral arteries. It is hypothesized that the developing embryo releases biochemical signals that result in the woman developing hypertension and preeclampsia so that the foetus can benefit from a greater amount of maternal circulation of nutrients due to increased blood flow to the impaired placenta. This results in a conflict between the maternal organism's Darwinian fitness and survival and the developing foetus because the foetus is invested in only its survival and fitness while the mother is invested in this pregnancy and subsequent potential pregnancies.

Another evolutionary hypothesis for vulnerability to preeclampsia is the idea of ensuring pair-bonding between the mother and father and paternal investment in the foetus. Researchers posit the idea that preeclampsia serves as an adaptation for the mother to terminate investment in a foetus that might have an unavailable paternal donor, as determined by repeated semen exposure of the paternal donor to the mother. Various studies have shown that women who frequently had exposure to partners' semen before conception had a reduced risk of preeclampsia. Also, subsequent pregnancies by the same paternal donor had a reduced risk of preeclampsia while subsequent pregnancies by a different paternal donor had a higher risk of developing preeclampsia.

Diagnosis

Criteria

Pre-eclampsia is well diagnosed when a pregnant woman develops both:
  blood pressure >140 systolic and/or >90 diastolic (two separate readings taken at least six hours apart)
  0.3 grams or more of protein in a 24-hour urine sample (proteinuria).

A rise in baseline blood pressure (BP) of 30 mmHg systolic or 15 mmHg diastolic, while not meeting the absolute criteria of 140/90, is still considered important to note, but is not considered diagnostic.

"Severe pre-eclampsia" involves a BP over 160/110, proteinuria more than 1 g/24 h and signs of end organ damage (CNS) dysfunction with symptoms like headache; pulmonary edema; renal dysfunction with oliguria or creatinine over 1.5 mg/dL; hepatocellular injury with ALT more than two-fold upper normal limit; hematologic dysfunction with platelet count less than 100,000/µL or DIC; placental dysfunction with IUGR or oligohydramnios etc.)

Other Symptoms

Swelling or edema (especially in the hands and face) was originally considered an important sign for a diagnosis of pre-eclampsia, but in current medical practice only hypertension and proteinuria are necessary for a diagnosis. Pitting edema (unusual swelling, particularly of the hands, feet, or face, notable by leaving an indentation when pressed on) can be significant, and should be reported to a health care provider.

Although eclampsia is potentially fatal (2% of cases), pre-eclampsia is often asymptomatic, and so its detection depends on signs or investigations. Nonetheless, one symptom is crucially important because it is often misinterpreted: epigastric pain may be confused with heartburn, a common problem of pregnancy. In general, none of the signs of pre-eclampsia are specific, and even convulsions in pregnancy are more likely to have causes other than eclampsia in modern practice. Diagnosis, therefore, depends on finding a coincidence of several pre-eclamptic features, the final proof being their regression after delivery.

Some women develop high blood pressure without proteinuria (protein in urine), which is called pregnancy-induced hypertension (PIH) or gestational hypertension. Both pre-eclampsia and PIH are regarded as very serious conditions and require careful monitoring of mother and baby.

[The above text is adapted from Pre-eclampsia. (2014, March 6). In Wikipedia, The Free Encyclopedia. Retrieved 07:24, Mar. 11, 2014, from the worldwide web at en.wikipedia.org/w/index.php?title=Pre-eclampsia&oldid=598400889]

Establishment of Pre-Eclampsia State

We demonstrate that ratio of the amount of polypeptides or amounts of combinations of polypeptides in CTB binding microparticle s to Annexin V binding microparticles of a cell, tissue, organ or organism that is suffering (or is at risk of suffering) from pre-eclampsia is higher than the cognate polypeptide/combination ratio (i.e., the ratio of the amount of polypeptides or amounts of combinations of polypeptides in CTB binding microparticle s to the amount of polypeptides or amounts of combinations of polypeptides in Annexin V binding microparticles) in normal or healthy cell, tissue, organ or organisms, i.e., those not suffering from pre-eclampsia.

We therefore describe a method of establishing the pre-eclampsia state of cell, tissue, organ or organism of interest, preferably an organism.

Accordingly, the method described above may be such that the states of the cell, tissue, organ or organism comprise a pre-eclampsia state and a healthy state. The polypeptide may be selected from the group consisting of: PlGF, FLT1, BNP, ANP, CD9, PAI-1, TGF β, PCT, S100b, TIMP1, CD105 or IL6.

Any combination of two or more of the above polypeptides may be used, as described above The organism may comprise a pregnant organism such as a pregnant mammal, e.g., a pregnant human.

The pregnant organism may be in the first trimester of pregnancy, the second trimester of pregnancy or the third trimester of pregnancy. A sample may be taken of a pregnant woman in the third trimester of pregnancy, for example, and subjected for analysis as described in this document to establish whether she is, or is at risk of, suffering from pre-eclampsia.

The CTB binding microparticle polypeptide/combination to Annexin V CD9 microparticle polypeptide/combination ratio may be higher in a pre-eclampsia state compared to a healthy state.

The method may comprise providing a sample of microparticles of or from the cell, tissue, organ or organism of interest. The amount of PlGF, FLT1, BNP, ANP, CD9, PAI-1, TGF β, PCT, S100b, TIMP1, CD105 or IL6 or a combination of any two or more of PlGF, FLT1, BNP, ANP, CD9, PAI-1, TGF β, PCT, S100b, TIMP1, CD105 or IL6 in CTB binding microparticle s, i.e., microparticles which comprise GM1 gangliosides, preferably which bind to Cholera Toxin B (CTB) is established.

The amount of the selected polypeptide or combination of polypeptides in Annexin V binding microparticles, i.e., microparticles which comprise exposed phosphotidylserine, preferably which bind to Annexin V is also established. The ratio between the polypeptide or combination amounts in CTB binding microparticle s compared to the polypeptide or combination amount of CD9 in Annexin V binding microparticles is then established. This ratio is compared to the CTB binding microparticle polypeptide or combination amount to Annexin V binding microparticle polypeptide or combination amount ratio of a normal or healthy cell, tissue, organ or organism (i.e., not suffering from pre-eclampsia).

Where the ratio is higher for the cell, tissue, organ or organism of interest than the ratio from the "normal" cell, tissue, organ or organism of interest, then the cell, tissue, organ or organism of interest is determined to be suffering, or at risk of suffering from, pre-eclampsia.

Monitoring of Changes of Pre-Eclampsia State

According to the methods and compositions described here, the CTB binding microparticle polypeptide to Annexin V binding microparticle polypeptide ratio may be used to monitor various changes of a pre-eclampsia state of a cell, tissue, organ or organism.

Accordingly, we describe a method for detecting a change in pre-eclampsia state of a cell, tissue, organ or organism. The method may comprise detecting a change in a CTB binding microparticle polypeptide to Annexin V binding microparticle polypeptide ratio of the cell, tissue, organ or organism (or a profile comprising such a ratio). Such a change may indicate a change in pre-eclampsia state of the cell, tissue, organ or organism.

The CTB binding microparticle polypeptide to Annexin V binding microparticle polypeptide ratio of a cell, tissue, organ or organism may be monitored or tracked over time intervals to establish or monitor or detect changes of pre-eclampsia state.

It will be understood that, where reference is made to establishing or determining the pre-eclampsia state of a cell, tissue, organ or organism, this will be understood to encompass establishing or determining the pre-eclampsia state, per se, as well as establishing or determining whether or not (and the extent of) cell, tissue, organ or organism being at risk of transitioning or going into that pre-eclampsia state. In other words, establishment of pre-eclampsia state includes establishment of risk of entering or suffering from that pre-eclampsia state.

The CTB binding microparticle polypeptide to Annexin V binding microparticle polypeptide ratio may be used to detect whether the cell, tissue, organ or organism is in a normal (undiseased) state or a pre-eclampsia state. It may be used to monitor the progression of a cell, tissue, organ or organism from a normal, undiseased state to a pre-eclampsia state. It may be used to monitor the stage of pre-eclampsia of the cell, tissue, organ or organism.

Detecting and Treating Pre-Eclampsia

We describe a method of detecting pre-eclampsia in a cell, tissue, organ or organism, the method comprising obtaining a sample from or of that cell, tissue, organ or organism, performing a method as set out above on the sample, and comparing the CTB binding microparticle polypeptide to Annexin V binding microparticle polypeptide ratio thereby obtained with a CTB binding microparticle polypeptide to Annexin V binding microparticle polypeptide ratio of a sample known to be of or from a pre-eclampsia cell, tissue, organ or organism.

We further describe a method of treatment or prevention of a pre-eclampsia in a cell, tissue, organ or organism, the method comprising detecting pre-eclampsia in a cell, tissue, organ or organism as set out above, and administering a treatment for pre-eclampsia to the cell, tissue, organ or organism.

Monitoring of Recovery from Pre-Eclampsia

Protein levels of any one or more pre-eclampsia biomarker polypeptide may be monitored in the two different microparticle populations (viz, annexin V- and CTB-binding subfractions) in a single individual—e.g., during an episode of pre-eclampsia—to monitor the injury, recovery and baseline in a patient.

The level of one or more pre-eclampsia biomarker polypeptide in one population may indicate pre-eclampsia, while the level of that one or more pre-eclampsia biomarker polypeptide in the other may indicate recovery from pre-eclampsia. By measuring the relative levels of these two populations, it can be determined if a patient is still suffering from pre-eclampsia (i.e. sick, poor prognosis), has initiated recovery from pre-eclampsia (i.e. recovering, good prognosis) or is in good health.

The ratio of CTB binding microparticle polypeptide to Annexin V binding microparticle polypeptide may also be used to indicate prognosis of the patient.

Biological Sample

The methods and compositions described here involve the ratio of CTB binding microparticle polypeptide to Annexin V binding microparticle polypeptide secreted by a cell in order to monitor its state. Conveniently, the ratio may be determined by taking a biological sample comprising secretions of the cell.

Where the cell is comprised in an organism, the sample may comprise any number of things, including, but not limited to, bodily fluids (including, but not limited to, blood, nasopharyngeal secretions, urine, serum, lymph, saliva, anal and vaginal secretions, perspiration and semen, of virtually any organism.

The sample is selected from the group consisting of: sweat, urine, blood, tears, saliva, bronchoaveolar fluid, tumoral effusions, epididymal fluid, amniotic fluid and milk.

Where the sample is of an organism, the organism may comprise any animal or plant. The organism may comprise a mammal, such as a human. The human may be a pregnant human.

Microparticles

The microparticle may in particular comprise a vesicle such as a microvesicle. The microparticle may comprise a CD9+ microparticle.

The microparticle may compris a microvesicle, an exosome, an ectosome or an apoptotic body.

The microparticle may comprise a vesicle or a flattened sphere limited by a lipid bilayer. The microparticle may comprise a diameter of 40-100 nm. The microparticle may be formed by inward budding of the endosomal membrane. The microparticle may have a density of ~1.13-1.19 g/ml and may float on sucrose gradients. The microparticle may be enriched in cholesterol and sphingomyelin, and lipid raft markers such as GM1, GM3, flotillin and the src protein kinase Lyn.

Methods of isolating microparticles are known in the art and are described in detail in the Examples below, as well as in documents such as International Patent Publication WO 2009/105044.

We describe in particular a technology to rapidly isolate different lipid microparticles found in plasma that could be used to identify and/or stratify biomarkers in different microparticle sub-populations to enhance their diagnostic, prognostic or theranostic value.

We therefore provide a method of treating a sample containing microparticles, the method comprising: (a) selecting microparticles in the sample which comprise GM1 gangliosides; and/or (b) selecting microparticles in the sample which comprise exposed phosphotidylserine.

The method may be such that step (a) comprises selecting microparticles in the sample which bind to Cholera Toxin subunit B (CTB); or in which step (b) comprises selecting microparticles in the sample which bind to Annexin V, or both.

The method may be such that it further comprises a step of selecting microparticles by size, for example, by size exclusion chromatography.

The method may be such that the microparticles comprise CD9+ microparticles.

Specifically, we provide a method to rapidly isolate annexin V- and CTB-binding subfractions of lipid microparticles from plasma for the detection of microparticle-associated proteins. Rapid isolation of annexin V- and CTB-binding subfractions lipid microparticle subpopulations could provide a means to stratify known disease biomarkers further into more defined plasma subfractions and improve their diagnostic, prognostic or theranostic values.

We provide a method for fractionating a sample containing microparticles. The method may comprise selecting an Annexin V-subfraction of microparticles or a CTB-binding sub-fraction of microparticles, or both. The method may comprise performing a method as set out above.

The method may further comprise the step of detecting and/or quantitating a membrane protein or a luminal protein, or both, in a fractionated sample of microparticles.

We provide a purified sample of microparticles, in which: (a) substantially all microparticles in the sample are capable of binding to cholera toxin B (CTB) but not to Annexin V; or (b) substantially all microparticles in the sample are capable of binding to Annexin V but not to cholera toxin B (CTB).

EXAMPLES

Example 1

Rationale

To circumvent this conundrum and develop alternative techniques for isolating membrane vesicles, we focus on membrane lipid as the target for isolation. A defining feature of circulating membrane vesicles is the derivation of their bi-lipid membrane from the plasma membrane. The plasma membrane is a highly compartmentalized cellular structure with an ordered distribution of proteins and lipids that are highly restricted in their rotational and lateral diffusion within the plane of the membrane. This ordered distribution generates structurally and functionally unique microdomains, and such microdomains have been shown to be critical for membrane activities such as cell signalling, cell adhesion and membrane trafficking[11]. The best characterised microdomain to date is the lipid raft which is enriched in cholesterol and saturated lipids such as sphingolipids. Another microdomain is the caveolae which are specialized uncoated cell surface invaginations. Caveolae are generally viewed as a specialized subtype of lipid rafts. These lipid raft microdomains are organized by the lipid constituents, namely cholesterol and sphingolipids. Non-lipid raft microdomains have been reported and these appeared to be organized by proteins e.g. the actin cytoskeleton, galectin-1, K- and H-ras.

The compartmentalization of the plasma membrane into microdomains with specialized structures and functions suggest that the biogenesis of each class of membrane vesicles from the plasma membrane is microdomain-specific. Therefore, the membrane lipids of circulating vesicles could reflect the microdomain from which they were derived and may determine their composition and functions. Indeed, membrane of exosomes which originated from endosomes is reportedly enriched in cholesterol and GM1 gangliosides, and this enrichment appears to distinguish exosomes from other membrane vesicles[12]. Cholesterol- and GM1 ganglioside-rich membranes are reflective of lipid rafts which represent the major sites of endocytosis. Exposed phosphatidylserine has been reported to be present on membrane of several extracellular vesicles including exosomes[12]. Although monocytes and macrophages endothelial cells are known to secrete vesicles with exposed phosphatidylserines during inflammation, circulating vesicles with exposed phosphatidylserine in healthy individual is thought to originate primarily from platelets[13]. Together, the studies on membrane lipids of circulating vesicles suggest that circulating vesicles could be differentiated by their membrane phospholipid composition, specifically GM1 gangliosides and phosphatidylserines. As these two phospholipids are known to bind cholera toxin B chain (CTB) and annexin V (AV) respectively, CTB and AV are potentially ligands for extracting different populations of circulating vesicles.

In this study, we tested here if circulating plasma membrane vesicles could be fractionated according to their affinity for CTB and AV, and if these fractionated vesicles could be used for discovery of PE biomarkers.

Example 2

Materials and Methods—Plasma Collection

The recruitment and enrolment of third trimester PE and matched healthy pregnant women by KKH were approved by the Singhealth Centralised Institution Review Board (CIRB Ref No: CIRB 2011/476/D). PE was defined as maternal systolic blood pressure of >140 mmHg and/or diastolic blood pressure of >90 mmHg on two occasions separated by 6 h and proteinuria of 300 mg in a 24-h period after 20 weeks of gestation as per guidelines of the American College of Obstetricians and Gynecologists. Peripheral blood was collected into EDTA vacutainer tubes, centrifuged and the plasma samples were stored at −80° C. until analysis. The plasma samples were analysed within 3 months and were not freeze-thaw more than twice.

There was a total of 11 PE patients and 11 healthy pregnant patients (controls) enrolled. The mean gestation age of PE presentation for the 11 PE patients was 30.5 weeks (range 24.0 to 35.0 weeks). The mean systolic and diastolic blood pressure of the 11 PE patients were 166 mmHg (range 148-182 mmHg) and 97 mmHg (range 71-114 mmHg) respectively.

The mean gestation of the 11 control and 11 PE patients at the time of collection were 31.9 weeks (range 27.9 to 36.0 weeks) and 32.4 weeks (range 28.4 to 38.0 weeks) respectively. The mean age of the control and PE patients were 27.7 years (range 20 to 38 years) and 32.2 years (range 21 to 38 years) respectively. The mean gravidity of the control and PE patients were 2.0 (range 1 to 5) and 1.9 (range 1 to 3) respectively. The mean parity of the control and PE patients were 0.7 (range 0 to 3) and 0.2 (range 0 to 1) respectively. The mean BMI of the control and PE patients were 24.8 kg/m$^2$ (range 18.3 to 33.2 kg/m$^2$) and 30.8 kg/m$^2$ (range 22.3 to 43.2 kg/m$^2$) respectively.

None of control patients had co-morbidity. Nine of the 11 PE patients had severe pre-eclampsia (>BP 160/110). One PE patient subsequently developed eclampsia. One PE patient was severely obese (BMI 43.2 kg/m$^2$) while another had developed gestational diabetes.

Of the 11 control and 11 PE patients, 6 control and 6 PE patients were processed for analyses using both mass spectrometry and a commercially available array of antibodies. The remainder 5 control and 5 PE patients were processed for analysis using ELISA for candidate biomarkers that were not covered in the standard commercial antibody array.

Example 3

Materials and Methods—Isolation of GM1 Ganglioside- and Phosphatidylserine-Rich Membrane Vesicles CTB (SBL Vaccin AB) and AV (BioVision) was biotinylated using Sulfo-NHS Biotin (Thermo Scientific, #21217) as per manufacturer's instruction. Ten μL plasma from each healthy and pre-eclampsia patients were incubated with 0.5 ηg biotinylated CTB or 0.5 ηg biotinylated AV in 100 μL Binding Buffer (2.5 mM calcium chloride, 0.01 M Hepes and 0.14 M sodium chloride) for 30 minutes at 37° C. in a rotating tube. At the same time, 100 µL of Dynabeads® MyOne Streptavidin T1 (Life Technology) was washed thrice with 100 µL Wash Buffer (0.1% BSA in PBS) by vortex mixing the beads, immobilizing the beads with a magnet and removing the supernatant for each wash. After removing the last wash buffer, the beads were resuspended in 100 µL Binding Buffer. 5 µL of the washed beads were then added to the plasma-CTB or plasma-AV reaction mix and incubated with rotation for 30 minutes. The beads were immobilised with a magnet and the supernatant was removed. The beads were then washed thrice with 200 µL AV Binding Buffer as described above. The bead-captured membrane vesicles were then analysed by SDS-PAGE, ELISA, antibody array and mass spectrometry.

Example 4

Materials and Methods—SDS-PAGE

The beads were boiled in 28 µL of a standard denaturing/reducing SDS-PAGE loading buffer and resolved on 4-12% SDS-polyacrylamide gels.

Example 5

Materials and Methods—ELISA

To assay for membrane proteins such as CD9, the beads were incubated with 1:500 dilution of mouse anti-human CD9 antibody (Santa Cruz) with rotation for 30 minutes. The beads were then immobilized and supernatant was removed, washed thrice with 200 µL Wash Buffer, and then incubated with 1:5000 HRP conjugated donkey anti-mouse IgG antibody (Santa Cruz) for 30 minutes with rotation at room temperature. After washing, the beads were incubated with 100 µL Amplex Red Substrate (Life Technology, A12222) for 30 minutes and fluorescent intensity was measured at 530/590 nm (Ex/Em). To assay for luminal proteins, the bound vesicles are lysed with 100 µL of cell lysis buffer (Biovision, K269-500). The lysed vesicles were then biotinylated by adding 10 µL 1:4000 diluted 10 mM Sulfo-NHS Biotin (Thermo Scientific, #21217). To assay for CD9, sFlt1, BNP, ANP, PLGF, magnetic bead conjugated antibody specific for the protein of interest was then added. The antibody-bound protein was then immobilized by magnet and washed thrice as described above. The target protein was assayed using Amplex Ultra Red Substrate as described earlier.

Example 6

Materials and Methods—Antibody Array

For antibody array, CTB- and AV-vesicles were isolated using from each of 6 PE patients and 6 healthy controls by incubating 30 µL of plasma with 1.5 ng biotinylated CTB or AV, respectively. The isolated vesicles were lysed as described above and analysed for proteins using RayBio® Custom Quantibody Array (Cat# QAH-CUST) according to manufacturer's instructions (RayBio, Norcross, Ga.).

Example 7

Materials and Methods—Mass Spectrometry

For mass spectrometry, 300 µL of pooled plasma from either 6 PE patients or 6 healthy control were incubated with 15 ng CTB or annexin V to isolate CTB- and AV-vesicles. 60 µL of the washed beads prepared as described above were then added to the plasma-CTB or plasma-AV reaction mix and incubated with rotation for 30 minutes. The beads were immobilised with a magnet and the supernatant was removed. The beads were then washed thrice with 200 µL AV Binding Buffer as described above. The isolated vesicles were lysed and resolved on a protein gel. Each gel lane was sliced separately into 8 pieces. The gel pieces were destained; proteins in the gel were reduced by 10 M dithiothreitol (DTT) at 56° C. for 1 h and alkylated by 55 mM iodoacetamide (IAA) for 45 min in the dark at room temperature. Tryptic digestion was performed by using porcine trypsin (Sequencing Grade Modified, Promega, Wis.) overnight. The tryptic peptides were extracted by 5% formic acid in 50% acetonitrile (ACN) and vacuum dried by speedvac (Sze S K, de Kleijn D P, Lai R C, et al. Elucidating the secretion proteome of human embryonic stem cell-derived mesenchymal stem cells. Mol Cell Proteomics 2007; 6(10): 1680-9.). Each dried fraction was reconstituted in 100 µL of 0.1% formic acid and analyzed using an LTQ-FT Ultra mass spectrometer (Thermo Electron, Bremen, Germany) coupled with a Prominence™ HPLC unit (Shimadzu). For each analysis, samples was injected from an autosampler (Shimadzu) and concentrated in a Zorbax peptide trap (Agilent, Palo Alto, Calif.). The peptide separation was performed in a capillary column (75 µm inner diameter×15 cm) packed with C18 AQ (5 µm particles, 300 Å pore size; Michrom Bioresources, Auburn, Calif.). Mobile phase A (0.1% formic acid in H2O) and mobile phase B (0.1% formic acid in acetonitrile) were used to establish the 90 min gradient comprising 3 min of 0-5% B and then 52 min of 5-25% B followed by 19 min of 25-80% B, maintenance at 80% B for 8 min, and finally re-equilibration at 5% B for 8 min. The HPLC system was operated at a constant flow rate of 30 µL min-1, and a splitter was used to create an effective flow rate of ~300 nL min-1 at the electrospray emitter. The sample was injected into an LTQ-FT through an ADVANCE™ CaptiveSpray™ source (Michrom Bioresources) with an electrospray potential of 1.5 kV. The gas flow was set at 2, ion transfer tube temperature was 180° C., and collision gas pressure was 0.85 millitorr. The LTQ-FT was set to perform data acquisition in the positive ion mode as described previously (Sze S K, de Kleijn D P, Lai R C, et al. Elucidating the secretion proteome of human embryonic stem cell-derived mesenchymal stem cells. Mol Cell Proteomics 2007; 6(10): 1680-9.). Briefly, a full MS scan (350-1600 m/z range) was acquired in the FT-ICR cell at a resolution of 100,000. The linear ion trap was used to collect peptides and to measure peptide fragments generated by CID. The 10 most intense ions above a 500-count threshold were selected for fragmentation in CID (MS2). For each experiment, MS/MS (dta) spectra of the eight gel fractions were combined into a single mascot generic file by a home-written program. Protein identification was achieved by searching the combined data against the IPI human protein database (version 3.34; 69, 164 sequences, 29, 064, 825 residues) via an in-house Mascot server (Version 2.3.02, Matrix Science, UK). The search parameters were: a maximum of 2 missed cleavages using 1.5 trypsin; fixed modification was carbaminomethylation of cysteine and variable modifications was oxidation of methionine. The mass tolerances were set to 10 ppm and 0.8 Da for peptide precursor and fragment ions respectively. Protein identification was accepted as true positive if two different peptides were found to have scores greater than the homology or identity scores.

Example 8

Materials and Methods—Statistical Analysis

Statistical analysis was performed using Mann-Whitney U test. Differences were considered to be statistically significant when the P values were less than 0.05.

Example 9

Results—CTB and AV Extracted Protein Containing Vesicles from Plasma

Figure 1:
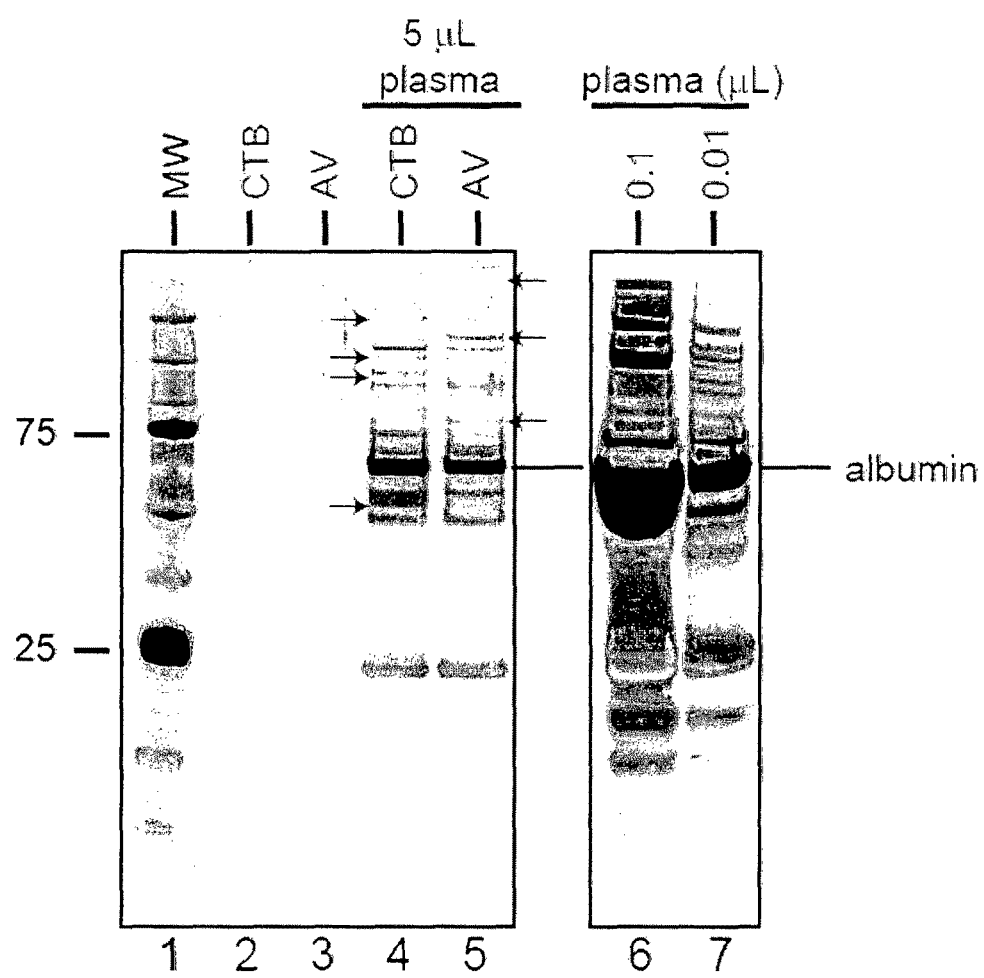
FIG. 1. Protein profile of CTB- or AV-vesicles in human plasma. 5 μL plasma from a healthy donor was incubated with biotinylated Cholera Toxin subunit B (CTB) or with biotinylated Annexin V (AV).

Plasma was incubated with biotinylated CTB or AV followed by streptavidin-conjugated magnetic beads. After extensive washing, the beads were boiled in a protein reducing and denaturing buffer, and analyzed by SDS-PAGE for protein (FIG. 1). The amount of protein extracted from 5 µL plasma by CTB or AV was less than that in 0.01 µL plasma or less than 0.1% of the starting protein concentration. Despite the relatively low resolution of a 2D-gel, there were distinct differences in the protein profile in the CTB- and AV-lipid vesicles (FIG. 1).

Example 10

Results—Presence of Distinct CTB- and AV-Vesicle Populations in the Plasma

Plasma was first extracted for either CTB- or AV-vesicles followed by extraction for AV- and CTB-vesicles, respectively. The extracted vesicles were then assayed for CD9, an ubiquitous membrane protein which was used here as a surrogate marker for plasma membrane. The level of CD9 in CTB-vesicles was similar before and after depletion with AV (FIG. 2). Likewise, the level of CD9 in AV-vesicles was similar before and after depletion with CTB. Since neither of the vesicles was depleted by extraction of the other vesicle, the two vesicles did not share an affinity for either ligands and were distinct populations.

Example 11

Results—Candidate Biomarkers for PE Segregated Differently in Circulating CTB- and AV-Vesicles of Pre-Eclampsia and Healthy Pregnant Women Vesicles were isolated from plasma of pre-eclampsia and matched healthy pregnant women. They were then assayed for the presence of previously reported pre-eclampsia biomarkers using either ELISA or a commercially available antibody array. Plasma from two different sets of pre-eclampsia patients and matched healthy controls were used; one for each assay.

Using a commercially available array of antibodies, CTB- and AV-vesicles from 6 PE patients and 6 matched healthy controls were assayed for Angiotensin-converting enzyme 2 (ACE2), Angiopoietin 1 (ANGPT1), C Reactive Protein (CRP), E-selectin (SELE), Endoglin (CD105), Growth hormone (GH), Interleukin-6 (IL-6), P-selectin (SELP), Plasminogen activator inhibitor-1 (PAI-1), Placenta growth factor (PlGF), Pro-calcitonin (PCT), S100b, Tumor growth factor β (TGF β), TIMP metallopeptidase inhibitor 1 (TIMP1) and Tumor necrosis factor α (TNF α) (FIG. 3 and FIG. 4). Four proteins, namely CD105, IL6, PlGF, and TIMP1 were significantly elevated in only CTB- but not AV-vesicles of pre-eclampsia patients. Another four PAI-1, PCT, S100b, TGF β were elevated in both CTB- and AV-vesicles of PE patients.

For other candidate biomarkers that were not covered in the antibody array, CTB- and AV-vesicles from five PE patients and five matched controls were assayed by ELISA. The proteins assayed were CD9, Vascular endothelial growth factor receptor 1 (FLT1), Brain natriuretic peptide (BNP), Atrial natriuretic peptide (ANP) and Placenta Growth Factor (PlGF). ANP was significantly increased in the CTB- but not AV-vesicles of PE patients while FLT1, BNP and PlGF were significantly increased in both CTB- and AV-vesicles of PE patients (FIG. 5). The statistically significant increased PlGF level (p=0.047) in AV-vesicles of PE patients contrasted with its insignificant increase (p=0.055) when assayed using antibody arrays. This discrepancy could be a statistical anomaly as the two assays were conducted using small samples of two independent sets of patients and controls (p=0.055). CD9 was significantly decreased in the CTB- but significantly increased in AV-vesicles of PE patients.

Together, these two studies demonstrate that previously reported candidate biomarkers for PE were present and differentially distributed in CTB- and AV-vesicles of PE patients relative to matched healthy controls.

Example 12

Results—Proteomic Analysis of the CTB- and AV-Vesicle Populations in the Plasma of Pre-Eclampsia and Healthy Pregnant Women For a comprehensive proteomic analysis of the CTB- and AV-vesicles from the pooled plasma of 6 pre-eclampsia and 6 healthy pregnant women, proteins in these vesicles were identified by mass spectrometry. A total of 285 and 269 proteins were detected in the CTB- and AV-vesicles of PE patients respectively, while 420 and 322 proteins were detected in those of healthy controls (FIG. 6). Of the 285 and 420 proteins in the CTB-vesicles of PE and healthy pregnant women, 198 proteins were found in the CTB vesicles of both patient groups. Likewise, 165 proteins were found in the AV-vesicles of both patient groups.

Therefore, the remaining proteins which were present only in the vesicles of either PE or healthy pregnant women, i.e. 87 CTB-proteins of PE patients, 104 AV-proteins of PE patients, 222 CTB-proteins of healthy pregnant women and 157 AV-proteins of healthy pregnant women (FIG. 6) represented candidate PE biomarkers (Table 1 and Table 2).

24 of the 87 CTB- and 104 AV-proteins were found in both vesicles while 67 of the 222 CTB- and 157 AV-proteins in the control group were present in both vesicles (Table 3).

11 of the 87 CTB-proteins in PE patients were present in AV-vesicles of healthy pregnant women while 17 of the 104 AV-proteins in PE patients were present in CTB-vesicles of the matched control group (Table 4).

These observations indicated that the candidate biomarkers were distributed in all possible permutations between the two vesicle types of PE patients versus healthy pregnant women. Therefore, a single PE biomarker could be differentially expressed in the two vesicles of a pregnant woman. This differential expression would potentially increase the robustness of the biomarker and facilitate comparison between patients by determining the ratio of the biomarker in the two vesicles.

TABLE 1

Table 1A: 63 proteins only in CTB - vesicles of PE patients (n = 6)

ANTXR1
APC
APOA1
APOC1
APOC2
APOE
ARFIP1
ARL5B
ATPAF1
C7
C9orf4
CD37
CDC2L1
CDC6
CDKL2
CIB2
CSHL1
E2F7
EFEMP1
F13A1
GCA
GGT1
HSPA5
HSPA7
IGFBP3
IGKV2-40
IGLV8-61
INHBC
INHBE
IPI00045460
IPI00385253
IPI00385555
IPI00387025
IPI00479426
IPI00796011
IPI00827643
KIF27
KRT27
KRT28
KSR2
LOC100292046
LOC441687
LONRF3
MMP7
NF1
NID1
NONO
NT5C3L
ORM1
PCF11
PEG3
PRL
PRX
RELN
RPS6
SAA1
SERPINA6
TFAP2E
THBS3
UBA1
UNC13B
VPS4A
WDR60

Table 1B: 198 proteins present in CTB - vesicles of both PE (n = 6) and healthy pregnant women (n = 6)

A1BG
ACTB
ACTBL2
ADAM12
AGT
AHSG
AMBP
APCS
APOA2
APOA4
APOA5
APOB
APOC3
APOC4
APOD
APOF
APOL1
APOM
ASPN
ATP6AP2
B4GALT1
BMP1
C1QC
C1R
C1RL
C1S
C20orf3
C3
C4A
C4B
C4BPA
C5
C8B
C8G
C9
CAMP
CASP12
CD14
CD5L
CDADC1
CDC5L
CDH1
CDH23
CDH5
CETP
CFB
CFH
CLTC
CLU
COL18A1
COL6A3
CP
CPB2
CRP
CSH1
DAK
DEFA1
DNAH6
EBI3
ENO1
F2
F5
F7
FBLN1
FBLN5
FETUB
FGA
FGB
GC
GDF15
GH2
GPLD1
GPX3
GSN
HAUS3
HBB
HBD
HP
HSP90AA1
HSP90B1
IGFALS
IGHA1
IGHG2
IGHG4
IGHM
IGHV3-48
IGJ
IGK@
IGKV3-20
IGLC1

TABLE 1-continued

IGLV7-43
IPI00003469
IPI00003470
IPI00007899
IPI00186448
IPI00382420
IPI00382436
IPI00382440
IPI00382481
IPI00384392
IPI00384401
IPI00384407
IPI00385264
IPI00385985
IPI00387026
IPI00387106
IPI00387116
IPI00387118
IPI00783024
IPI00791534
IPI00807428
IPI00816799
IPI00829827
IPI00830088
IPI00909649
IPI00922295
IPI00940451
IPI00941961
IPI00944652
ITGA2B
ITIH1
ITIH2
ITIH3
ITIH4
KRT1
KRT10
KRT14
KRT2
KRT4
KRT5
KRT6B
KRT77
KRT8
KRT9
LBP
LCP1
LOC100126583
LOC100290320
LOC100291682
LOC401847
LOC55908
LPA
LRRC8B
LYZ
MAGT1
MASP2
MGAT1
MGP
PCMT1
PF4
PGLYRP2
PLTP
PLXND1
PON1
PON3
PPBP
PRDX6
PRG4
PRKDC
PROS1
PRSS3
PSG1
PSG4
PZP
QSOX1
RAB10
RAB15
RAB1B
RAB35
RAB8A

TABLE 1-continued

RAN
RARRES2
SAA4
SCFV
SEPP1
SERPINA10
SERPINA3
SERPINA4
SERPINC1
SERPING1
SHBG
SIGLEC16
SIL1
SPP2
SRI
SVEP1
TF
THBS1
THBS4
THSD1
TLL2
TRAP1
TSKU
TTR
UBE2N
VCL
VTN
VWF

Table 1C: 155 proteins present only in CTB - vesicles of healthy pregnant women (n = 6)

A2ML1
ACTN4
ADH4
AFM
ALB
ANTXR2
ANXA7
ANXA8L1
APOH
ARF1
ARF6
ARHGAP1
C19orf30
C19orf68
C2
C20orf114
C20orf94
C22orf40
C4BPB
CCT6A
CCT8
CD36
CDAN1
CDC10L
CDC42
CDC73
CDK5
CDKN1B
CFL1
CIDEB
CLIC1
CMTM5
CRTAC1
CXCL12
CYB5D2
DNAH3
EEF1A1
ERBB4
ETV7
FAM21A
FBXO7
FCER1G
FGG
FGL1
FMO5
GAPDH
GP1BB
GP9

TABLE 1-continued

GPX1
GSTK1
GSTM4
GTF2H1
HBA2
HBZ
HLA-C
HPR
HSP90AB1
HSPB1
HTRA1
HYOU1
IGHD
IGKC
IGLV306
IGLV3-25
IPI00029863
IPI00259932
IPI00382421
IPI00383016
IPI00387027
IPI00387101
IPI00387105
IPI00736860
IPI00748607
IPI00827500
IPI00827891
IPI00829590
IPI00829803
IPI00855844
IPI00874178
IPI00945820
ITGB3
KIAA1409
KLKB1
KRT13
KRT15
KRT84
LALBA
LECT2
LMAN2
LOC100289960
LOC100292483
LOC440786
LOC652128
LOC653879
LTF
MAP2K2
MASP1
MDFIC
MOBKL1B
MPP1
MTHFD1
MYH14
NAPA
NID2
NSF
NSMAF
OGT
OXSR1
PAFAH1B2
PCBP2
PCYOX1
PDCD6IP
PGK2
PLUNC
PPIA
PRPS1
PRPSAP2
RAB11B
RAB14
RAB28
RAB5C
RAB8B
RAC2
RASSF6
RB1CC1
RBP4
RCTPI1
RHOA

TABLE 1-continued

RNF123
S100A8
SAR1B
SDPR
SEMA3B
SERPIND1
SFRS2IP
SLC25A18
SMARCC2
SMC3
SNORA67
SPTA1
TAGLN2
TIMP2
TRIM28
TRIM33
TTC23L
TUBB1
UBC
UBE2M
UBXN7
WNT16
YKT6
YWHAQ
YWHAZ
ZNF645
ZNHIT1

TABLE 2

Table 2A: 80 proteins present in only AV - vesicles of PE patients (n = 6)

A1BG
BMP1
CDH23
CFH
COL18A1
DLEC1
EBI3
HTR7P
IGHM
IPI00003470
IPI00382420
IPI00384407
IPI00736860
IPI00829956
IPI00830018
IPI00830088
KRT17
KRT8
AFM
ANXA5
APOA2
APOA5
APOC3
ARHGAP1
ASPN
B4GALT1
BNIP2
C1QB
C1QTNF6
C5
CD300LG
CDH18
CP
CRP
DMRTA1
DSP
F5
FAM21A
FGG
GP1BB
H2AFV
HTRA1
HYOU1
IGHA1

TABLE 2-continued

IGHG3
IGLV3-25
IPI00003469
IPI00384392
IPI00385985
IPI00387115
IPI00748607
IPI00783024
IPI00829841
IPI00903033
IPI00909484
IPI00910738
KIAA0586
KLKB1
KRT14
KRT5
KRT6B
KRT6C
KRT77
KRT84
LOC440786
LOC652128
LYZ
MYBL1
PCBP2
PLUNC
PLXND1
RFPL2
RPL32
SPP2
SYNPR
TF
TLL2
TLN2
TRIM33
TSNAXIP1

Table 2B: 165 proteins present in AV - vesicles of both PE (n = 6) and healthy pregnant women (n = 6)

A2ML1
AGT
ALB
AMBP
ANXA7
APCS
APOB
APOC1
APOC2
APOC4
APOD
APOE
APOF
APOL1
ARF1
ATP6AP2
C19orf30
C1QC
C1R
C1RL
C1S
C20orf114
C20orf3
C3
C4A
C4B
C4BPA
C4BPB
C8B
C9
CASP12
CD14
CD5L
CDADC1
CDC42
CDC6
CDH5
CETP
CFB
CHMP4B TABLE 2-continued CLTC
CLU
COL6A3
CPB2
CSH1
DAK
DEFA1
EFEMP1
FBLN1
FBLN5
FGA
FGB
GAPDH
GC
GH2
GPLD1
GPX3
HAUS3
HBA2
HBB
HP
HPR
HSP90AA1
HSP90AB1
HSP90B1
IGFALS
IGHG2
IGHG4
IGK@
IGKC
IGKV3-20
IGKV3D01
IGLC1
INHBC
IPI00007899
IPI00029863
IPI00382436
IPI00382440
IPI00382481
IPI00384401
IPI00385264
IPI00387106
IPI00387116
IPI00387118
IPI00783287
IPI00807428
IPI00816799
IPI00827643
IPI00829803
IPI00829827
IPI00909649
IPI00922295
IPI00944652
ITGA2B
KRT1
KRT10
KRT13
KRT2
KRT27
KRT4
KRT9
LALBA
LBP
LOC100126583
LOC100290320
LOC100291682
LPA
LRRC8B
LTF
MAGT1
MASP1
MASP2
MGP
MYH14
NSMAF
PAFAH1B2
PCYOX1
PDCD6IP
PF4
PGK2

TABLE 2-continued

PGLYRP2
PLTP
PON1
PON3
PPBP
PRDX6
PRG4
PROS1
PRSS3
PSG1
QSOX1
RAB15
RAB28
RAB35
RAB8A
RAC2
RAN
RASSF6
RB1CC1
RBP4
RPS6
S100A8
SAA1
SAA4
SAR1B
SEMA3B
SEPP1
SERPINA3
SERPINA6
SERPINC1
SERPIND1
SERPING1
SHBG
SIGLEC16
SLC8A3
SMO
SVEP1
THBS1
TRAP1
TSKU
TTR
VCL
VTN
VWF
YWHAZ

Table 2C: 90 proteins in only AV - vesicles of healthy pregnant women (n = 6)

ACTB
ACTBL2
ADAM12
AHSG
ALG9
ANGPTL6
ANTXR1
APC
APOA1
APOA4
APOM
ARFIP1
ARHGEF6
BICC1
BPGM
C1orf64
C8A
C8G
CBR1
CDC5L
CDY2B
COPS8
CORO1A
CSHL1
DNAH6
EEF1A2
EIF2AK2
ENO1
F2
F7
F9

TABLE 2-continued

FETUB
GBF1
GSN
HBD
HK3
IGJ
IGKV2-40
IGLV208
INHBE
IPI00011310
IPI00384399
IPI00384409
IPI00387025
IPI00387026
IPI00790470
IPI00827580
IPI00893755
IPI00921459
IPI00940451
IPI00941961
IPI00952561
ITIH1
ITIH2
ITIH3
ITIH4
KIF27
KRT7
LCAT
LCP1
LOC401847
LOC55908
MGC15705
MINPP1
OAF
OLFM3
PALM
PARD3B
PARVB
PCMT1
PDXP
PRKDC
PRL
PRX
PSG4
PZP
RAB10
RAB1B
RSU1
SCGB3A1
SERPINA10
SERPINA4
SIL1
THBS4
THSD1
TPCN1
UBE2D2
UBE2N
UBE2V1
XPNPEP3

TABLE 3

Table 3A: 24 proteins present in both CTB - and AV - vesicles of only PE patients (n = 6)

A2M
C20orf134
COLEC10
COLEC11
CRH
ERC1
FN1
HPX
IPI00382483
IPI00783023
IPI00828156
IPI00830044

TABLE 3-continued

IPI00890754
KRT16
KRT6A
LDHA
LRSAM1
LTBP1
MMP9
MMRN1
POSTN
SERPINA1
SFTPB
TM9SF1

Table 3B: 67 proteins present in both CTB - and AV - vesicles of only healthy pregnant women (n = 6)

CD9
CDH3
IPI00219910
IPI00941428
IPI00941443
IPI00952572
IPI00382476
IPI00387113
IPI00387120
IPI00743194
IPI00827875
IPI00827646
IPI00827695
ACTA1
AK1
APRT
ARF4
ARHGDIA
CA1
CA2
CAND1
CAP1
CAPN1
CAPNS1
CGN
CNDP1
CPN2
CUL3
ENO2
ENO3
FERMT3
FLNA
GCLM
GSTP1
ILK-2
KNG1
KPNB1
LOC100133511
LXN
MYH9
PAFAH1B3
PCSK9
PFN1
PLG
PPP2R1A
PRDX1
PRDX2
PROC
PSG3
PSG8
PSG9
PSME1
PSME2
PSMF1
RAB6B
RAC1
RAP1B
SERPINA11
SERPINA5
SERPINA7
SETD4
STOM
TFRC
TLN1

TABLE 3-continued

TUBA1C
TUBB2C
ZNF878

TABLE 4

Table 4A: 11 proteins present in CTB - vesicles of PE patients (n = 6) and AV - vesicles of healthy pregnant women (n = 6)

ANTXR1
APC
APOA1
ARFIP1
CSHL1
IGKV2-40
INHBE
IPI00387025
KIF27
PRL
PRX

Table 4B: 17 proteins present in AV - vesicles of PE patients (n = 6) and CTB - vesicles of healthy pregnant women (n = 6)

AFM
ARHGAP1
FAM21A
FGG
GP1BB
HTRA1
HYOU1
IGLV3-25
TRIM33
IPI00736860
IPI00748607
KLKB1
KRT84
LOC440786
LOC652128
PCBP2
PLUNC

Example 13

Results—Discussion

This study demonstrates that plasma contained at least two distinct populations of membrane vesicles that could be isolated according to their affinities for CTB and AV, and that their protein cargos distinct from each other and reflective of the disease state of the patients. As CTB and AV bind phospholipids, GM1 ganglioside and phosphatidylserine respectively, and as phospholipids are bipolar, any CTB- or AV-bound phospholipids from aqueous physiological would be a micelle or vesicle (as this is the thermodynamically stable configuration for phospholipids in aqueous solution). Therefore, CTB- or AV-affinity isolation techniques would be highly specific for the isolation of phospholipid membrane vesicles with minimal contamination of large non-vesicle biological complexes or soluble proteins.

This is the first description of plasma vesicles that bind exclusively to either CTB or AV. As such, the origin and physiological functions of these vesicles are unknown, and, their roles in the pathology of diseases have not been elucidated. Nevertheless, the strong association between their protein cargo load and disease manifestation implicates an active role in the pathophysiology, and therefore a sentinel for disease progression and resolution. The exclusiveness of the CTB and AV binding affinities in these vesicles indicate that the lipid compositions of these two vesicles are different and their membrane biogenesis originates from different microdomains in the plasma membranes. As different microdomains are functionally different, a difference in the origins and functions of these vesicles could be inferred. Additionally, we noted that serum is a rich source of platelet microparticles but a relatively poor source of CTB- or AV-binding vesicles, suggesting that the most of CTB- or AV-binding vesicles in the plasma were not platelet microparticles.

Based on our current understanding of membrane vesicles, we speculate that since the CTB-vesicles were rich in GM1 ganglioside, they could be derived from lipid rafts and therefore, were likely to be exosomes[12]. On the other hand, it is difficult to speculate on the identity of AV-vesicles as exosomes, microvesicles, ectosomes and possibly others have been reported to have exposed phosphatidylserines[12]. In healthy cells, phosphatidylserines are mainly localised on the inner leaflet of the membrane and this asymmetry is actively maintained by ATP-dependent aminophospholipid translocase[15]. In dying cells or membrane vesicles where ATP production is not sustainable, phosphotidylserines become exposed by spontaneous diffusion between the two membrane leaflets. We hypothesize that the absence of phosphatidylserines in CTB-vesicles could be due to the characteristic rigidity of the lipid rafts16 from which the CTB-affinity was supposedly derived. This rigidity could restrict the diffusion of lipids and proteins in the plasma membrane and prevent spontaneous distribution of phosphatidylserines between the two lipid membranes.

Analysis of CTB- and AV-vesicles in the plasma of pre-eclampsia patients and matched healthy controls revealed that they carry previously reported biomarker candidates for pre-eclampsia. However, the relative levels of each candidate biomarker in each of these two vesicles from plasma of patients and matched healthy controls were distributed into nearly all possible permutations. For example, CD105 was elevated in CTB- but AV-vesicles of PE patients, PAI-1 was elevated in both CTB- and AV-vesicles of PE patients, and CD9 was reduced in CTB-vesicles but not elevated in AV-vesicles of PE patients. This diverse permutation was further validated by a global proteomic profiling of the vesicles by mass spectrometry. The CTB- and AV-vesicles of PE patients, and that of matched healthy pregnant women not only had proteins that were unique to each of the two pregnant women cohorts, the CTB- and AV-vesicles in each women cohorts also had proteins unique to either the CTB- or AV-vesicles. Therefore, the CTB- or AV-vesicles in the plasma represent independent sources of biomarkers and the use of these vesicles could expand the biomarker discovery potential of plasma by a factor of 2. This together with the inherent removal of high abundance plasma proteins during vesicle isolation enhanced global proteomic analysis as evidenced by the uncovering of many candidate biomarkers with less than one ml of plasma. In addition, the different distribution of a protein in the two vesicles could be exploited as a mean to normalize the relative level of a biomarker and facilitate inter-patient comparison. However, the different distribution of a biomarker in the two vesicles will necessitate the isolation of vesicles not only for biomarker discovery but also the subsequent biomarker assay.

In conclusion, we described a novel technology to isolate two unique classes of membrane vesicles from the plasma and demonstrates the tractability of this technology in interrogating plasma proteome for low abundance plasma proteins as candidate PE biomarkers. This proof of concept for this plasma vesicle extraction methodology and the use of the vesicle for biomarker discovery provide a rationale for the use of CTB- and AV-vesicles for biomarker discovery in obstetrics & gynecology and other medical specialties.

REFERENCES

1. Abalos E, Cuesta C, Grosso A L, Chou D, Say L. Global and regional estimates of preeclampsia and eclampsia: a systematic review. Eur J Obstet Gynecol Reprod Biol 2013.
2. Tan K H, Kwek K, Yeo G S. Epidemiology of pre-eclampsia and eclampsia at the KK Women's and Children's Hospital, Singapore. Singapore Med J. 2006; 47(1):48-53.
3. Sibai B M. Disparity in the rate of eclampsia and adverse pregnancy outcome from eclampsia: a tale of two countries. Obstet Gynecol 2011; 118(5): 976-7.
4. Sibai B, Dekker G, Kupferminc M. Pre-eclampsia. Lancet 2005; 365(9461): 785-99.
5. Espinoza J. Recent biomarkers for the identification of patients at risk for preeclampsia: the role of uteroplacental ischemia. Expert Opin Med Diagn 2012; 6(2): 121-30.
6. Simpson R J, Lim J W, Moritz R L, Mathivanan S. Exosomes: proteomic insights and diagnostic potential. Expert Rev Proteomics 2009; 6(3): 267-83.
7. Taylor D D, Akyol S, Gercel-Taylor C. Pregnancy-associated exosomes and their modulation of T cell signaling. J Immunol 2006; 176(3): 1534-42.
8. Thery C, Ostrowski M, Segura E. Membrane vesicles as conveyors of immune responses. Nat Rev Immunol 2009; 9(8): 581-93.
9. Duijvesz D, Luider T, Bangma C H, Jenster G. Exosomes as Biomarker Treasure Chests for Prostate Cancer. European Urology 2011; 59(5): 823-31.
10. Simpson R J, Mathivanan S. Extracellular microvesicles: The need for internationally recognised nomenclature and stringent purification criteria. Journal of Proteomics and Bioinformatics 2012; 5(2).
11. Laude A J, Prior I A. Plasma membrane microdomains: Organization, function and trafficking (Review). Molecular Membrane Biology 2004; 21(3): 193-205.
12. Thery C, Ostrowski M, Segura E. Membrane vesicles as conveyors of immune responses. Nat Rev Immunol 2009; 9(8): 581-93.
13. Rautou P-E, Mackman N. Del-etion of Microvesicles From the Circulation. Circulation 2012; 125(13): 1601-4.
14. Sze S K, de Kleijn D P, Lai R C, et al. Elucidating the secretion proteome of human embryonic stem cell-derived mesenchymal stem cells. Mol Cell Proteomics 2007; 6(10): 1680-9.
15. Zwaal R F A, Schroit A J. Pathophysiologic Implications of Membrane Phospholipid Asymmetry in Blood Cells. Blood 1997; 89(4): 1121-32.
16. Niemelä P S, Ollila S, Hyvönen M T, Karttunen M, Vattulainen I. Assessing the Nature of Lipid Raft Membranes. PLoS Comput Biol 2007; 3(2): e34.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

Each of the applications and patents mentioned in this document, and each document cited or referenced in each of the above applications and patents, including during the prosecution of each of the applications and patents ("application cited documents") and any manufacturer's instructions or catalogues for any products cited or mentioned in each of the applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments; it should be understood that the invention as claimed should not be unduly limited to such specific embodiments. Indeed, various modifications of the described modes for carrying out the invention which are obvious to those skilled in molecular biology or related fields are intended to be within the scope of the claims.

The invention claimed is:

1. A method of detecting pre-eclampsia in an individual, the method comprising:
   (a) providing a sample from the individual;
   (b) detecting the level of expression or amount of an fms-like tyrosine kinase-1 (FLT1) pre-eclampsia biomarker polypeptide in a cholera toxin B (CTB) binding microparticle type of the sample;
   (C) comparing the level of expression or amount of the FLT1 pre-eclampsia biomarker in a CTB binding microparticle type of a sample from an individual known to be not suffering from pre-eclampsia;
   in which an elevated level of expression or amount of the FLT1 pre-eclampsia biomarker polypeptide indicates that the individual is suffering from, or is likely to be suffering from, pre-eclampsia.

2. A method according to claim 1, which further comprises detecting an elevated level of expression or amount of a BNP pre-eclampsia biomarker polypeptide.

3. A method according to claim 1, which further comprises a step of normalizing the level or amount of the selected polypeptide between two or more samples.

4. The method of claim 3, wherein the normalization is conducted with reference to BNP, CD9 and/or TIMP-1 polypeptide.

5. A method according to claim 1 further comprising a step of selecting microparticles by size.

6. The method of claim 5, wherein the microparticles selected by size comprise CD9+ microparticles.

7. A method of monitoring the progress of an individual suffering from pre-eclampsia, the method comprising monitoring the modulation of expression of an FLT1 pre-eclampsia biomarker polypeptide in a cell, tissue or organ of the individual by the method of claim 1.

8. A method of prognosis of an individual suffering from pre-eclampsia, the method comprising detecting modulation of expression of an FLT1 pre-eclampsia biomarker polypeptide in a cell, tissue or organ of the individual by a method according to claim 1.

9. A method of choosing a therapy for an individual suffering from pre-eclampsia, the method comprising detecting modulation of expression of an FLT1 pre-eclampsia biomarker polypeptide in a cell, tissue or organ of the individual by a method according to claim 1 and choosing an appropriate therapy based on the severity of the pre-eclampsia.

10. A method of determining the likelihood of success of a particular therapy in an individual suffering from pre-eclampsia, the method comprising comparing the therapy with a therapy determined by a method according to claim 9.

11. A method of treatment of pre-eclampsia in a cell, tissue, organ or organism, the method comprising detecting pre-eclampsia in a cell, tissue, organ or organism by a method according to claim 1, and administering a treatment for pre-eclampsia to the cell, tissue, organ or organism.

12. The method of claim 1, wherein the sample is selected from the group consisting of: urine, blood, amniotic fluid, tears, saliva, bronchoalveolar fluid, tumoral effusions and milk.

13. The method of claim 1, wherein the microparticles comprise microvesicles, exosomes, ectosomes or apoptotic bodies.

14. A method of detecting pre-eclampsia in an individual, the method comprising:
   (a) providing a sample from the individual;
   (b) detecting the level of expression or amount of an fms-like tyrosine kinase-1 (FLT1) pre-eclampsia biomarker polypeptide in a cholera toxin B (CTB) binding microparticle type of the sample;
   (c) comparing the level of expression or amount of the FLT1 pre-eclampsia biomarker in a CTB binding microparticle type of a sample from an individual known to be not suffering from pre-eclampsia;
   in which an elevated level of expression or amount of the FLT1 pre-eclampsia biomarker polypeptide indicates that the individual is suffering from, or is likely to be suffering from, pre-eclampsia, and further establishing a profile comprising the expression or amount of a plurality of pre-eclampsia biomarker polypeptides selected from the polypeptides set out in Table 1A, Table 1B and Table 1C; Table 2A, Table 2B and Table 2C; Table 3A and Table 3B and Table 4A and Table 4B of the individual, and comparing the profile against a profile of an individual known to be not suffering from pre-eclampsia.

15. A method of treatment of pre-eclampsia in a cell, tissue or organ of an individual, the method comprising detecting pre-eclampsia in a cell, tissue or organ of an individual by a method according to:
   (a) providing a sample from the individual;
   (b) detecting the level of expression or amount of an fms-like tyrosine kinase-1 (FLT1) pre-eclampsia biomarker polypeptide in a cholera toxin B (CTB) binding microparticle type of the sample;
   (c) comparing the level of expression or amount of the FLT1pre-eclampsia biomarker in a CTB binding microparticle type of a sample from an individual known to be not suffering from pre-eclampsia;
   in which an elevated level of expression or amount of the FLT1 pre-eclampsia biomarker polypeptide indicates that the individual is suffering from, or is likely to be suffering from, pre-eclampsia, and administering an antihypertensive treatment for pre-eclampsia to the cell, tissue or organ of the individual, selected from the group consisting of Isradipine, Labetolol, Hydralazine, Nifedipine or magnesium sulfate.

* * * * *

SEQUENCE LISTING

```
<160> NUMBER OF SEQ ID NOS: 12

<210> SEQ ID NO 1
<211> LENGTH: 203
<212> TYPE: PRT
<213> ORGANISM: Homo sapiens

<400> SEQUENCE: 1

Leu Pro Ala Val Pro Gln Gln Trp Ala Leu Ser Ala Gly Asn Gly
1               5                   10                  15

Ser Ser Glu Val Glu Val Val Pro Phe Gln Glu Val Trp Gly Arg Ser
                20                  25                  30

Tyr Cys Arg Ala Leu Glu Arg Leu Val Asp Val Val Ser Glu Tyr Pro
            35                  40                  45

Ser Glu Val Glu His Met Phe Ser Pro Ser Cys Val Ser Leu Leu Arg
        50                  55                  60

Cys Thr Gly Cys Cys Gly Asp Glu Asn Leu His Cys Val Pro Val Glu
65                  70                  75                  80

Thr Ala Asn Val Thr Met Gln Leu Leu Lys Ile Arg Ser Gly Asp Arg
                85                  90                  95

Pro Ser Tyr Val Glu Leu Thr Phe Ser Gln His Val Arg Cys Glu Cys
            100                 105                 110

Arg His Ser Pro Gly Arg Gln Ser Pro Asp Met Pro Gly Asp Phe Arg
        115                 120                 125

Ala Asp Ala Pro Ser Phe Leu Pro Pro Arg Arg Ser Leu Pro Met Leu
    130                 135                 140

Phe Arg Met Glu Trp Gly Cys Ala Leu Thr Gly Ser Gln Ser Ala Val
145                 150                 155                 160

Trp Pro Ser Ser Pro Val Pro Glu Glu Ile Pro Arg Met His Pro Gly
                165                 170                 175

Arg Asn Gly Lys Lys Gln Gln Arg Lys Pro Leu Arg Glu Lys Met Lys
            180                 185                 190

Pro Glu Arg Cys Gly Asp Ala Val Pro Arg Arg
        195                 200

<210> SEQ ID NO 2
<211> LENGTH: 225
<212> TYPE: PRT
<213> ORGANISM: Homo sapiens

<400> SEQUENCE: 2

Ser Ser Ser Gly Ser Lys Leu Lys Asp Pro Glu Leu Ser Leu Lys Gly
1               5                   10                  15

Thr Gln His Ile Met Gln Ala Gly Gln Thr Leu His Leu Gln Cys Arg
                20                  25                  30
```

Gly Glu Ala Ala His Lys Trp Ser Leu Pro Glu Met Val Ser Lys Glu
            35                  40                  45

Ser Glu Arg Leu Ser Ile Thr Lys Ser Ala Cys Gly Arg Asn Gly Lys
        50                  55                  60

Gln Phe Cys Ser Thr Leu Thr Leu Asn Thr Ala Gln Ala Asn His Thr
65                  70                  75                  80

Gly Phe Tyr Ser Cys Lys Tyr Leu Ala Val Pro Thr Ser Lys Lys Lys
                85                  90                  95

Glu Thr Glu Ser Ala Ile Tyr Ile Phe Ile Ser Asp Thr Gly Arg Pro
            100                 105                 110

Phe Val Glu Met Tyr Ser Glu Ile Pro Glu Ile Ile His Met Thr Glu
        115                 120                 125

Gly Arg Glu Leu Val Ile Pro Cys Arg Val Thr Ser Pro Asn Ile Thr
    130                 135                 140

Val Thr Leu Lys Lys Phe Pro Leu Asp Thr Leu Ile Pro Asp Gly Lys
145                 150                 155                 160

Arg Ile Ile Trp Asp Ser Arg Lys Gly Phe Ile Ile Ser Asn Ala Thr
                165                 170                 175

Tyr Lys Glu Ile Gly Leu Leu Thr Cys Glu Ala Thr Val Asn Gly His
            180                 185                 190

Leu Tyr Lys Thr Asn Tyr Leu Thr His Arg Gln Thr Asn Thr Ile Ile
        195                 200                 205

Asp Val Gln Ile Ser Thr Pro Arg Pro Val Lys Leu Leu Arg Gly His
    210                 215                 220

Thr
225

<210> SEQ ID NO 3
<211> LENGTH: 32
<212> TYPE: PRT
<213> ORGANISM: Homo sapiens

<400> SEQUENCE: 3

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30

<210> SEQ ID NO 4
<211> LENGTH: 153
<212> TYPE: PRT
<213> ORGANISM: Homo sapiens

<400> SEQUENCE: 4

Met Ser Ser Phe Ser Thr Thr Thr Val Ser Phe Leu Leu Leu Leu Ala
1               5                   10                  15

Phe Gln Leu Leu Gly Gln Thr Arg Ala Asn Pro Met Tyr Asn Ala Val
            20                  25                  30

Ser Asn Ala Asp Leu Met Asp Phe Lys Asn Leu Leu Asp His Leu Glu
        35                  40                  45

Glu Lys Met Pro Leu Glu Asp Glu Val Val Pro Gln Val Leu Ser
    50                  55                  60

Glu Pro Asn Glu Glu Ala Gly Ala Ala Leu Ser Pro Leu Pro Glu Val
65                  70                  75                  80

Pro Pro Trp Thr Gly Glu Val Ser Pro Ala Gln Arg Asp Gly Gly Ala
                85                  90                  95

```
Leu Gly Arg Gly Pro Trp Asp Ser Ser Asp Arg Ser Ala Leu Leu Lys
                100                 105                 110

Ser Lys Leu Arg Ala Leu Leu Thr Ala Pro Arg Ser Leu Arg Arg Ser
            115                 120                 125

Ser Cys Phe Gly Arg Met Asp Arg Ile Gly Ala Gln Ser Gly Leu
        130                 135                 140

Gly Cys Asn Ser Phe Arg Tyr Arg Ser
145                 150

<210> SEQ ID NO 5
<211> LENGTH: 110
<212> TYPE: PRT
<213> ORGANISM: Homo sapiens

<400> SEQUENCE: 5

Ala Ile Glu Ile Ala Ala Ala Ile Trp Gly Tyr Ser His Lys Asp Glu
1               5                   10                  15

Val Ile Lys Glu Val Gln Glu Phe Tyr Lys Asp Thr Tyr Asn Lys Leu
            20                  25                  30

Lys Thr Lys Asp Glu Pro Gln Arg Glu Thr Leu Lys Ala Ile His Tyr
        35                  40                  45

Ala Leu Asn Cys Cys Gly Leu Ala Gly Gly Val Glu Gln Phe Ile Ser
    50                  55                  60

Asp Ile Cys Pro Lys Lys Asp Val Leu Glu Thr Phe Thr Val Lys Ser
65                  70                  75                  80

Cys Pro Asp Ala Ile Lys Glu Val Phe Asp Asn Lys Phe His Ile Ile
                85                  90                  95

Gly Ala Val Gly Ile Gly Ile Ala Val Val Met Ile Phe Gly
            100                 105                 110

<210> SEQ ID NO 6
<211> LENGTH: 135
<212> TYPE: PRT
<213> ORGANISM: Homo sapiens

<400> SEQUENCE: 6

Val His His Pro Pro Ser Tyr Val Ala His Leu Ala Ser Asp Phe Gly
1               5                   10                  15

Val Arg Val Phe Gln Gln Val Ala Gln Ala Ser Lys Asp Arg Asn Val
            20                  25                  30

Val Phe Ser Pro Tyr Gly Val Ala Ser Val Leu Ala Met Leu Gln Leu
        35                  40                  45

Thr Thr Gly Gly Glu Thr Gln Gln Gln Ile Gln Ala Ala Met Gly Phe
    50                  55                  60

Lys Ile Asp Asp Lys Gly Met Ala Pro Ala Leu Arg His Leu Tyr Lys
65                  70                  75                  80

Glu Leu Met Gly Pro Trp Asn Lys Asp Glu Ile Ser Thr Thr Asp Ala
                85                  90                  95

Ile Phe Val Gln Arg Asp Leu Lys Leu Val Gln Gly Phe Met Pro His
            100                 105                 110

Phe Phe Arg Leu Phe Arg Ser Thr Val Lys Gln Val Asp Phe Ser Glu
        115                 120                 125

Val Glu Arg Ala Arg Phe Ile
    130                 135

<210> SEQ ID NO 7
```

```
<211> LENGTH: 248
<212> TYPE: PRT
<213> ORGANISM: Homo sapiens

<400> SEQUENCE: 7

Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Glu Ser Ala Glu
50                  55                  60

Pro Glu Pro Glu Pro Glu Ala Asp Tyr Tyr Ala Lys Glu Val Thr Arg
65                  70                  75                  80

Val Leu Met Val Glu Thr His Asn Glu Ile Tyr Asp Lys Phe Lys Gln
                85                  90                  95

Ser Thr His Ser Ile Tyr Met Phe Phe Asn Thr Ser Glu Leu Arg Glu
            100                 105                 110

Ala Val Pro Glu Pro Val Leu Leu Ser Arg Ala Glu Leu Arg Leu Leu
        115                 120                 125

Arg Leu Lys Leu Lys Val Glu Gln His Val Glu Leu Tyr Gln Lys Tyr
130                 135                 140

Ser Asn Asn Ser Trp Arg Tyr Leu Ser Asn Arg Leu Leu Ala Pro Ser
145                 150                 155                 160

Asp Ser Pro Glu Trp Leu Ser Phe Asp Val Thr Gly Val Val Arg Gln
                165                 170                 175

Trp Leu Ser Arg Gly Gly Glu Ile Glu Gly Phe Arg Leu Ser Ala His
            180                 185                 190

Cys Ser Cys Asp Ser Arg Asp Asn Thr Leu Gln Val Asp Ile Asn Gly
        195                 200                 205

Phe Thr Thr Gly Arg Arg Gly Asp Leu Ala Thr Ile His Gly Met Asn
210                 215                 220

Arg Pro Phe Leu Leu Leu Met Ala Thr Pro Leu Glu Arg Ala Gln His
225                 230                 235                 240

Leu Gln Ser Ser Arg His Arg Arg
                245

<210> SEQ ID NO 8
<211> LENGTH: 55
<212> TYPE: PRT
<213> ORGANISM: Homo sapiens

<400> SEQUENCE: 8

Ala Pro Phe Arg Ser Ala Leu Glu Ser Ser Pro Ala Asp Pro Ala Thr
1               5                   10                  15

Leu Ser Glu Asp Glu Ala Arg Leu Leu Leu Ala Ala Leu Val Gln Asn
            20                  25                  30

Tyr Val Gln Met Lys Ala Ser Glu Leu Glu Gln Glu Gln Glu Arg Glu
        35                  40                  45

Gly Ser Arg Ile Ile Ala Gln
    50                  55

<210> SEQ ID NO 9
<211> LENGTH: 91
<212> TYPE: PRT
<213> ORGANISM: Homo sapiens
```

<400> SEQUENCE: 9

Ser Glu Leu Glu Lys Ala Met Val Ala Leu Ile Asp Val Phe His Gln
1               5                   10                  15

Tyr Ser Gly Arg Glu Gly Asp Lys His Lys Leu Lys Lys Ser Glu Leu
            20                  25                  30

Lys Glu Leu Ile Asn Asn Glu Leu Ser His Phe Leu Glu Glu Ile Lys
        35                  40                  45

Glu Gln Glu Val Val Asp Lys Val Met Glu Thr Leu Asp Asn Asp Gly
    50                  55                  60

Asp Gly Glu Cys Asp Phe Gln Glu Phe Met Ala Phe Val Ala Met Val
65                  70                  75                  80

Thr Thr Ala Cys His Glu Phe Phe Glu His Glu
                85                  90

<210> SEQ ID NO 10
<211> LENGTH: 37
<212> TYPE: PRT
<213> ORGANISM: Homo sapiens

<400> SEQUENCE: 10

Thr Asp Gln Leu Leu Gln Gly Ser Glu Lys Gly Phe Gln Ser Arg His
1               5                   10                  15

Leu Ala Cys Leu Pro Arg Glu Pro Gly Leu Cys Thr Trp Gln Ser Leu
            20                  25                  30

Arg Ser Gln Ile Ala
        35

<210> SEQ ID NO 11
<211> LENGTH: 300
<212> TYPE: PRT
<213> ORGANISM: Homo sapiens

<400> SEQUENCE: 11

Thr Val His Cys Asp Leu Gln Pro Val Gly Pro Glu Arg Gly Glu Val
1               5                   10                  15

Thr Tyr Thr Thr Ser Gln Val Ser Lys Gly Cys Val Ala Gln Ala Pro
            20                  25                  30

Asn Ala Ile Leu Glu Val His Val Leu Phe Leu Glu Phe Pro Thr Gly
        35                  40                  45

Pro Ser Gln Leu Glu Leu Thr Leu Gln Ala Ser Lys Gln Asn Gly Thr
    50                  55                  60

Trp Pro Arg Glu Val Leu Leu Val Leu Ser Val Asn Ser Ser Val Phe
65                  70                  75                  80

Leu His Leu Gln Ala Leu Gly Ile Pro Leu His Leu Ala Tyr Asn Ser
                85                  90                  95

Ser Leu Val Thr Phe Gln Glu Pro Pro Gly Val Asn Thr Thr Glu Leu
            100                 105                 110

Pro Ser Phe Pro Lys Thr Gln Ile Leu Glu Trp Ala Ala Glu Arg Gly
        115                 120                 125

Pro Ile Thr Ser Ala Ala Glu Leu Asn Asp Pro Gln Ser Ile Leu Leu
    130                 135                 140

Arg Leu Gly Gln Ala Gln Gly Ser Leu Ser Phe Cys Met Leu Glu Ala
145                 150                 155                 160

Ser Gln Asp Met Gly Arg Thr Leu Glu Trp Arg Pro Arg Thr Pro Ala
                165                 170                 175

```
Leu Val Arg Gly Cys His Leu Glu Gly Val Ala Gly His Lys Glu Ala
            180                 185                 190

His Ile Leu Arg Val Leu Pro Gly His Ser Ala Gly Pro Arg Thr Val
            195                 200                 205

Thr Val Lys Val Glu Leu Ser Cys Ala Pro Gly Asp Leu Asp Ala Val
            210                 215                 220

Leu Ile Leu Gln Gly Pro Pro Tyr Val Ser Trp Leu Ile Asp Ala Asn
225                 230                 235                 240

His Asn Met Gln Ile Trp Thr Thr Gly Glu Tyr Ser Phe Lys Ile Phe
            245                 250                 255

Pro Glu Lys Asn Ile Arg Gly Phe Lys Leu Pro Asp Thr Pro Gln Gly
            260                 265                 270

Leu Leu Gly Glu Ala Arg Met Leu Asn Ala Ser Ile Val Ala Ser Phe
            275                 280                 285

Val Glu Leu Pro Leu Ala Ser Ile Val Ser Leu His
            290                 295                 300

<210> SEQ ID NO 12
<211> LENGTH: 183
<212> TYPE: PRT
<213> ORGANISM: Homo sapiens

<400> SEQUENCE: 12

Val Pro Pro Gly Glu Asp Ser Lys Asp Val Ala Ala Pro His Arg Gln
1               5                   10                  15

Pro Leu Thr Ser Ser Glu Arg Ile Asp Lys Gln Ile Arg Tyr Ile Leu
            20                  25                  30

Asp Gly Ile Ser Ala Leu Arg Lys Glu Thr Cys Asn Lys Ser Asn Met
            35                  40                  45

Cys Glu Ser Ser Lys Glu Ala Leu Ala Glu Asn Asn Leu Asn Leu Pro
        50                  55                  60

Lys Met Ala Glu Lys Asp Gly Cys Phe Gln Ser Gly Phe Asn Glu Glu
65                  70                  75                  80

Thr Cys Leu Val Lys Ile Ile Thr Gly Leu Leu Glu Phe Glu Val Tyr
            85                  90                  95

Leu Glu Tyr Leu Gln Asn Arg Phe Glu Ser Ser Glu Glu Gln Ala Arg
            100                 105                 110

Ala Val Gln Met Ser Thr Lys Val Leu Ile Gln Phe Leu Gln Lys Lys
            115                 120                 125

Ala Lys Asn Leu Asp Ala Ile Thr Thr Pro Asp Pro Thr Thr Asn Ala
            130                 135                 140

Ser Leu Leu Thr Lys Leu Gln Ala Gln Asn Gln Trp Leu Gln Asp Met
145                 150                 155                 160

Thr Thr His Leu Ile Leu Arg Ser Phe Lys Glu Phe Leu Gln Ser Ser
            165                 170                 175

Leu Arg Ala Leu Arg Gln Met
            180
```